US010617309B2

(12) United States Patent
Matsumoto et al.

(10) Patent No.: US 10,617,309 B2
(45) Date of Patent: Apr. 14, 2020

(54) ELECTRONIC DEVICE, METHOD FOR CONTROLLING ELECTRONIC DEVICE, AND RECORDING MEDIUM

(71) Applicant: Panasonic Intellectual Property Management Co., Ltd., Osaka (JP)

(72) Inventors: Akinori Matsumoto, Osaka (JP); Koji Morikawa, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 229 days.

(21) Appl. No.: 15/803,782

(22) Filed: Nov. 5, 2017

(65) Prior Publication Data

US 2018/0140205 A1 May 24, 2018

(30) Foreign Application Priority Data

Nov. 22, 2016 (JP) .................................. 2016-227246
Jul. 11, 2017 (JP) .................................. 2017-135290

(51) Int. Cl.
*A61B 5/0205* (2006.01)
*A61B 5/0404* (2006.01)
(Continued)

(52) U.S. Cl.
CPC .......... *A61B 5/0205* (2013.01); *A61B 5/0404* (2013.01); *A61B 5/04288* (2013.01);
(Continued)

(58) Field of Classification Search
CPC . A61B 5/0205; A61B 5/02108; A61B 5/0404; A61B 5/04288
See application file for complete search history.

(56) References Cited

U.S. PATENT DOCUMENTS 4,318,412 A * 3/1982 Stanly .................. A61B 5/0006
600/508
4,442,315 A 4/1984 Segawa
(Continued)

FOREIGN PATENT DOCUMENTS

JP 57-086326 5/1982
JP 2008-237378 10/2008
(Continued)

*Primary Examiner* — Joseph M Dietrich
(74) *Attorney, Agent, or Firm* — Wenderoth, Lind & Ponack, L.L.P.

(57) ABSTRACT

An information processing system includes first and second electrodes for measuring cardiac potential, a pulse wave sensor that is disposed closer to the first electrode than to the second electrode and that measures a pulse wave, a buffer that amplifies a signal acquired by the first electrode, an interconnect wire that electrically connects the first electrode to a terminal of the buffer, a shield that shields the first electrode and the interconnect wire, and a shield potential generator that includes a first buffer circuit and a second buffer circuit having a larger drive current than the first buffer circuit and that starts applying, to the shield, a first generation signal generated by the first buffer circuit based on the acquired signal before a predetermined time point when the pulse wave is measured and starts applying a second generation signal generated by the second buffer circuit at the predetermined time point.

14 Claims, 42 Drawing Sheets

(51) Int. Cl.
    *A61B 5/0428*     (2006.01)
    *A61B 5/021*     (2006.01)
    *A61B 5/00*     (2006.01)

(52) U.S. Cl.
    CPC .......... *A61B 5/02108* (2013.01); *A61B 5/681* (2013.01); *A61B 5/6897* (2013.01); *A61B 5/6898* (2013.01)

(56) References Cited

U.S. PATENT DOCUMENTS

| | | |
|---|---|---|
| 2008/0238695 A1 | 10/2008 | Yanai et al. |
| 2014/0333332 A1 | 11/2014 | Matsumoto et al. |

FOREIGN PATENT DOCUMENTS

| | | |
|---|---|---|
| JP | 2012-120705 | 6/2012 |
| JP | 2014-158949 | 9/2014 |
| WO | 2007/002991 | 1/2007 |
| WO | 2014/038212 | 3/2014 |

\* cited by examiner

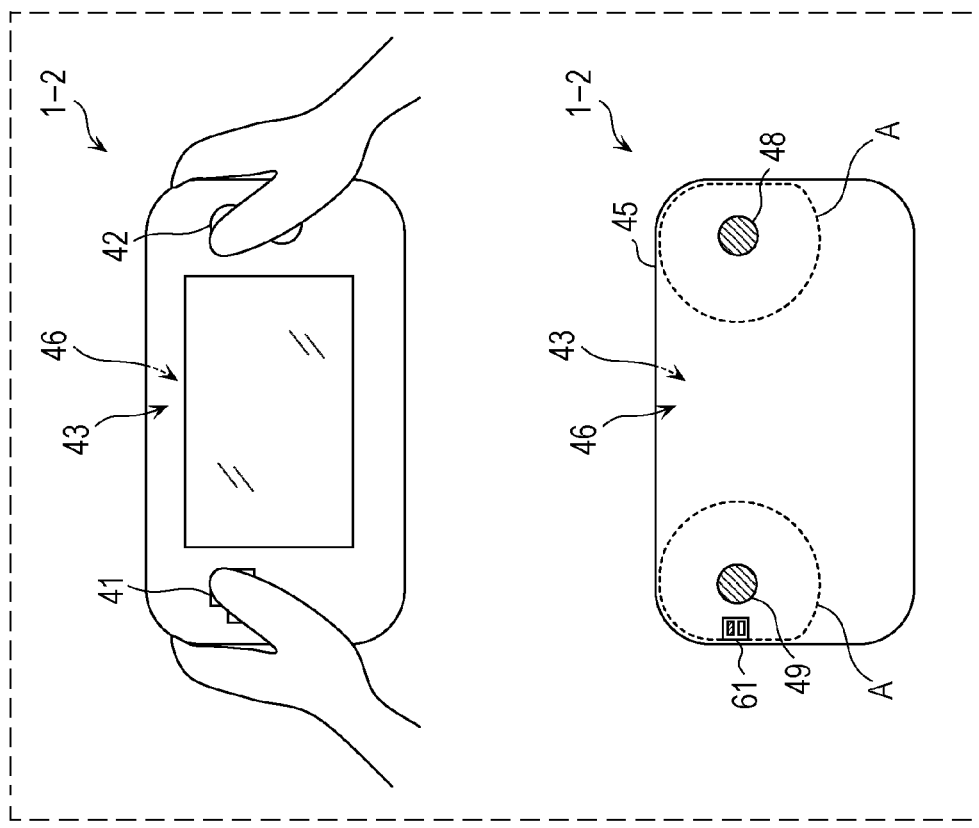
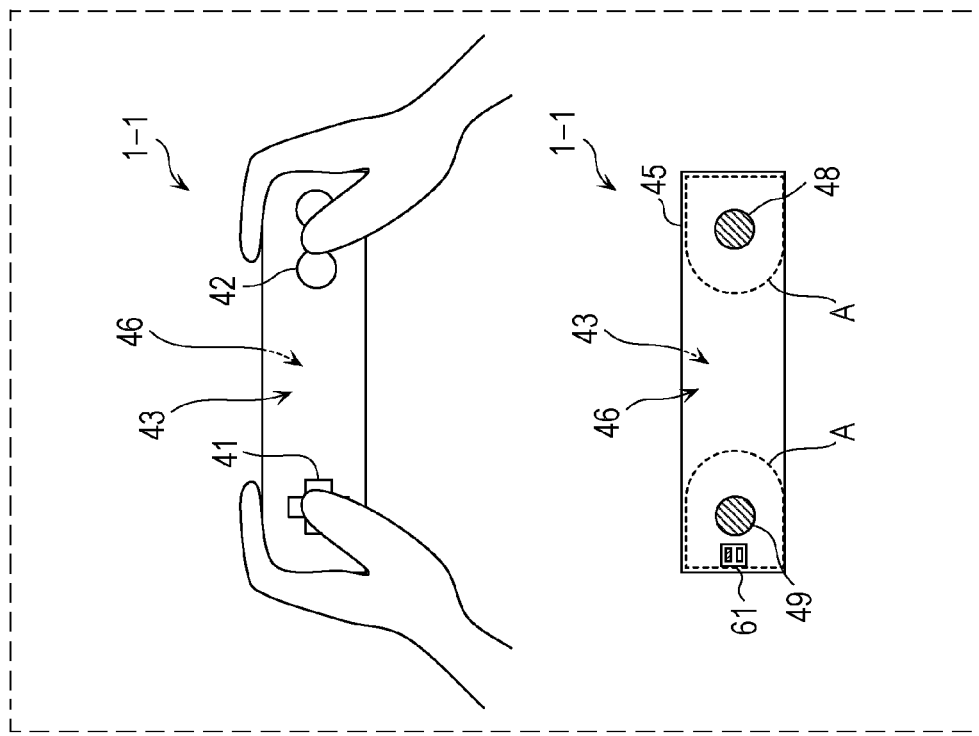

CONTACT AREA OF FINGER:
DIAMETER F = 14 mm

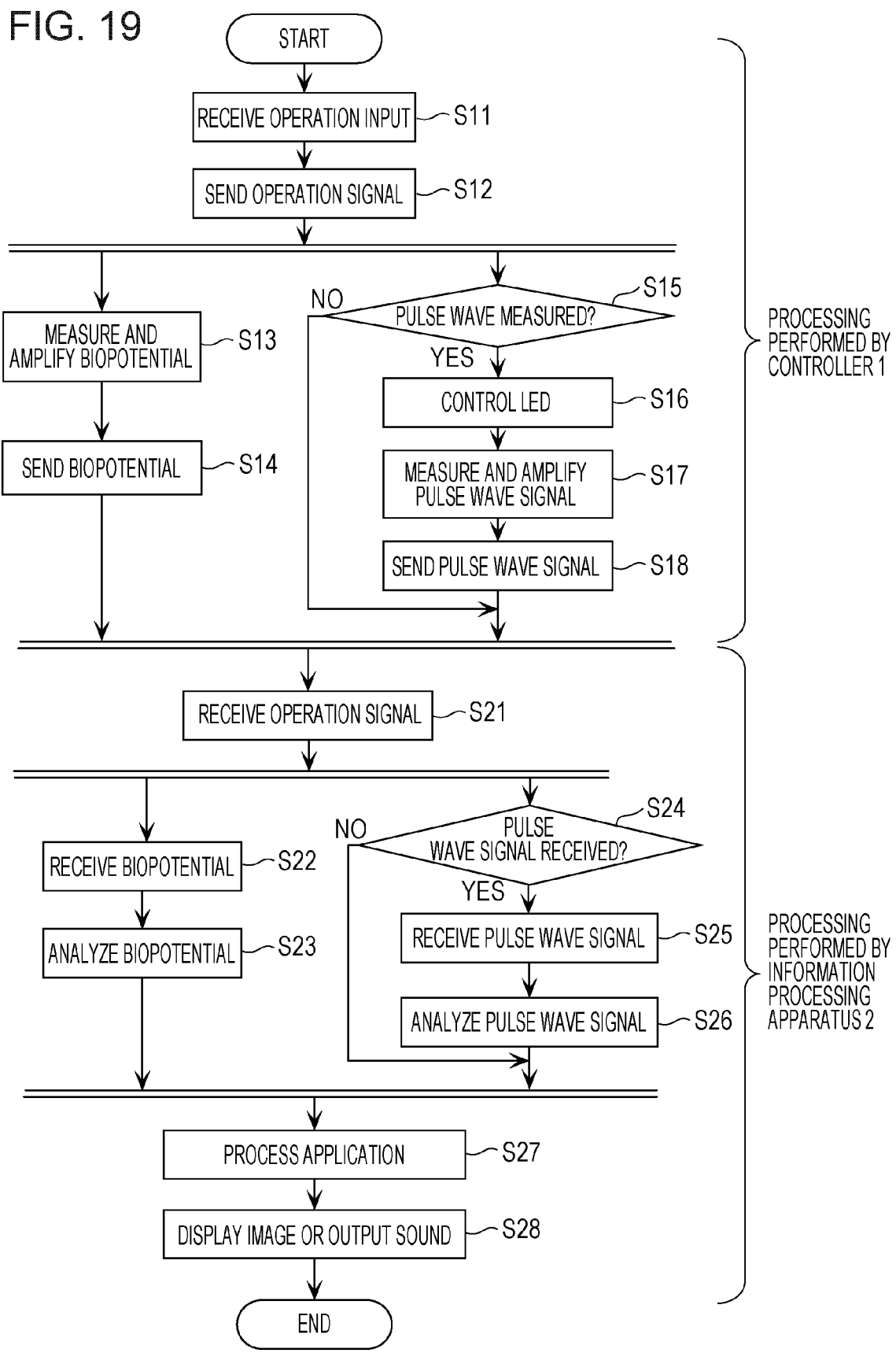

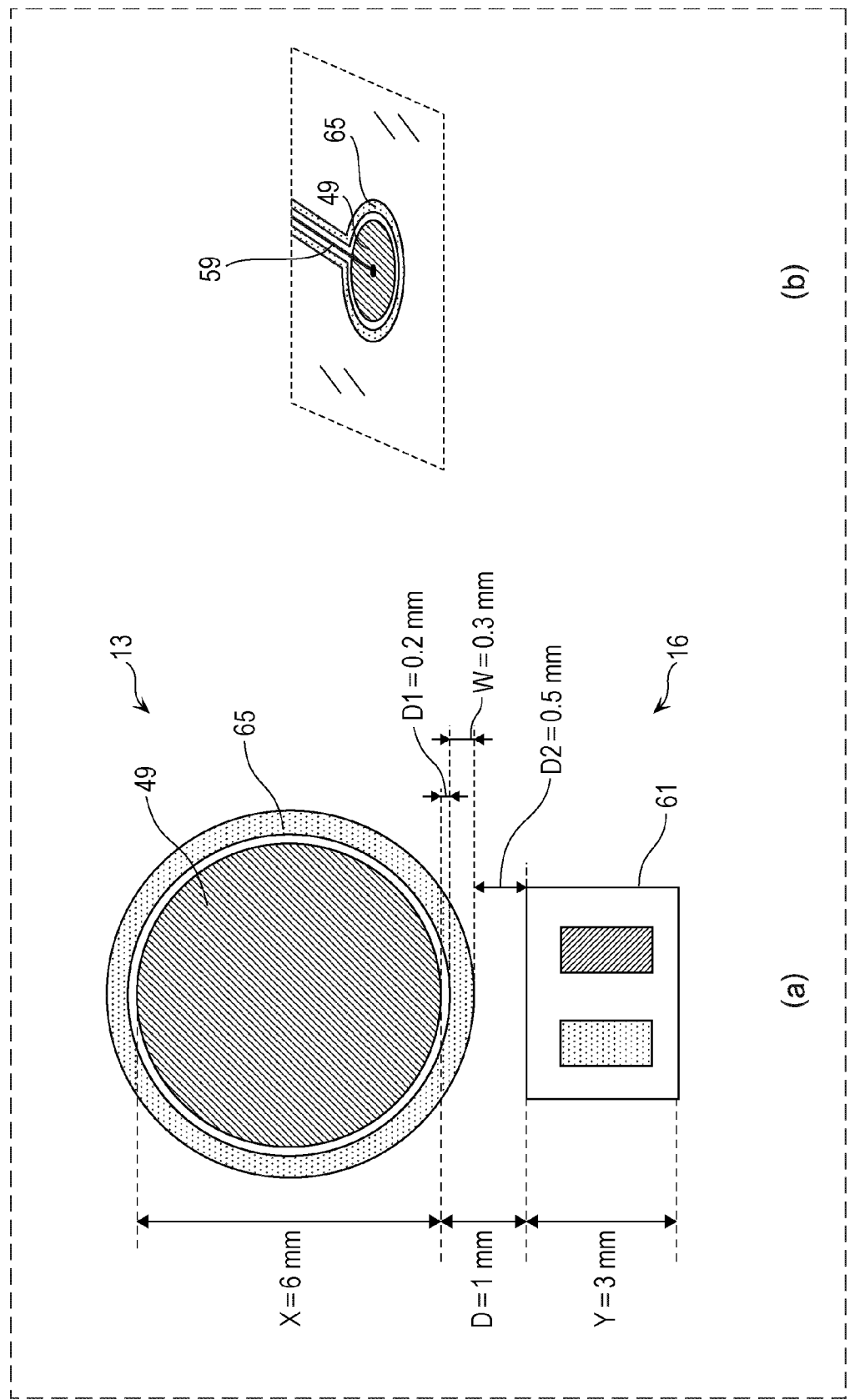

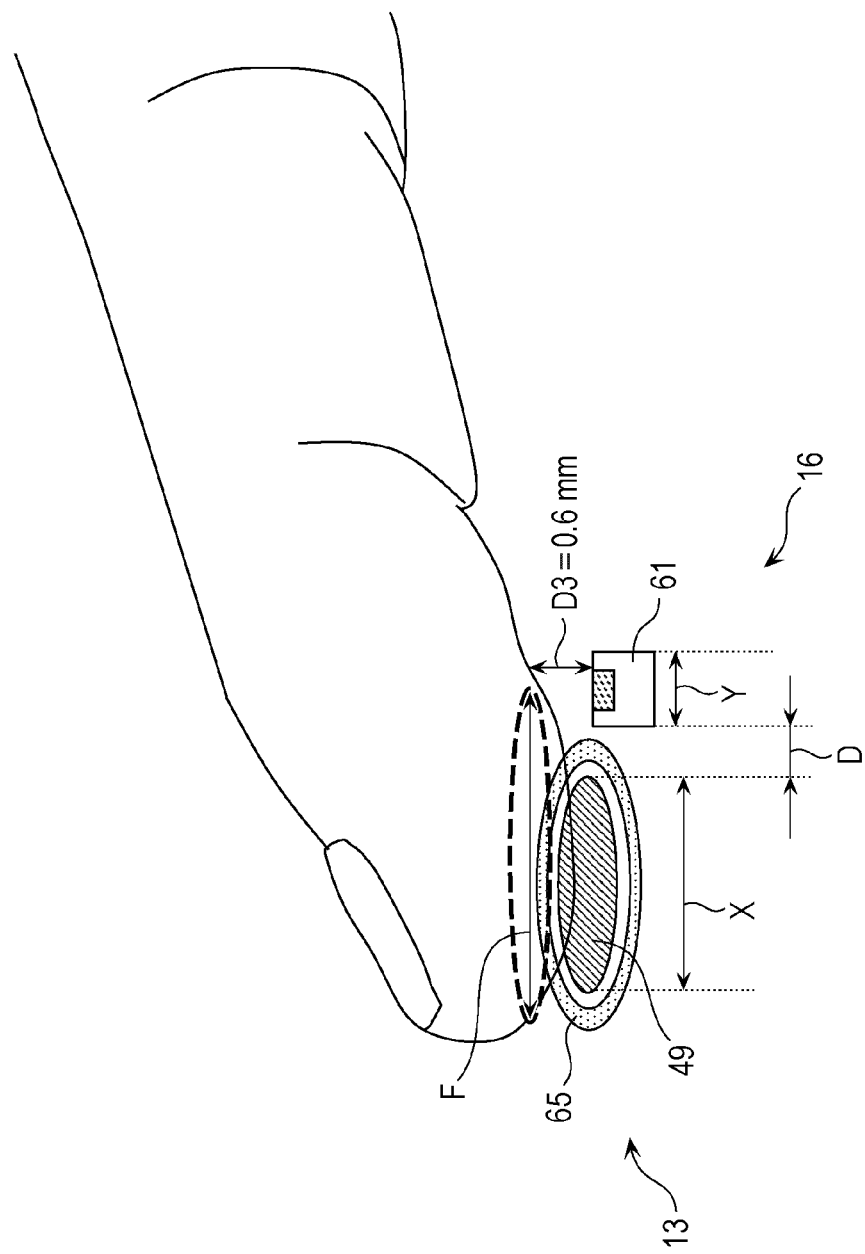

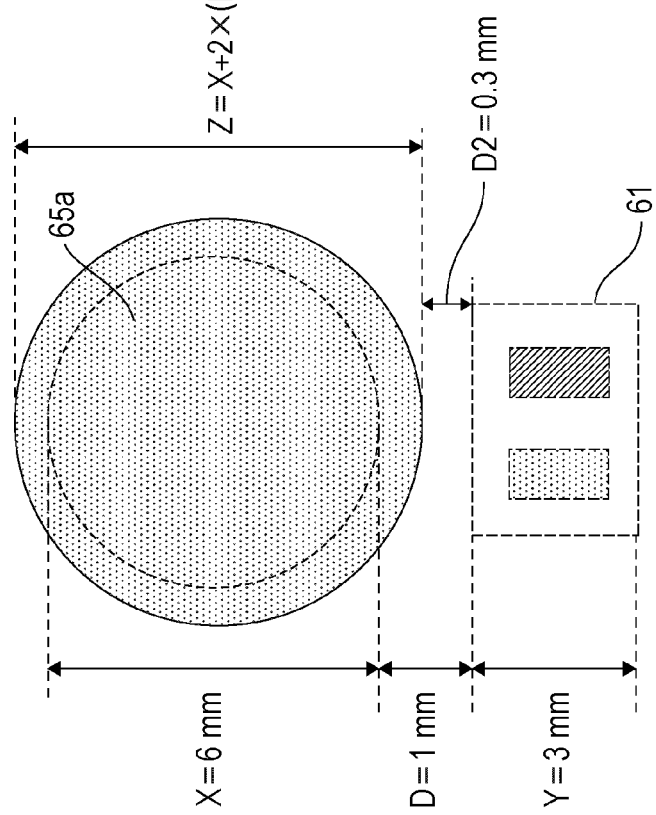

FIG. 31

| MEASUREMENT MODE | | LED CONTROL SIGNAL | SHIELD CONTROL SIGNAL | | | | PRESENCE OF OUTPUT SIGNAL | |
|---|---|---|---|---|---|---|---|---|
| | | | S1 | S2 | S3 | S4 | CARDIAC POTENTIAL | PULSE WAVE |
| FIRST STATE | ONLY CARDIAC POTENTIAL | L | H | L | L | L | YES | NO |
| SECOND STATE | CARDIAC POTENTIAL & PULSE WAVE | H | H | H | H | H | YES | YES |

FIG. 41

| | MEASUREMENT MODE | PULSE WAVEFORM INFORMATION | SHIELD CONTROL SIGNAL | | | | PRESENCE OF OUTPUT SIGNAL | |
| --- | --- | --- | --- | --- | --- | --- | --- | --- |
| | | | S1 | S2 | S3 | S4 | CARDIAC POTENTIAL | PULSE WAVE |
| FIRST STATE | ONLY CARDIAC POTENTIAL | NO | H | L | L | L | YES | NO |
| SECOND STATE | CARDIAC POTENTIAL & PULSE WAVE | YES | L | L | L | L | YES | YES |
| | | | H | L | L | L | | |
| | | | L | H | L | L | | |
| | | | L | H | H | H | | |
| | | | H | H | H | H | | |

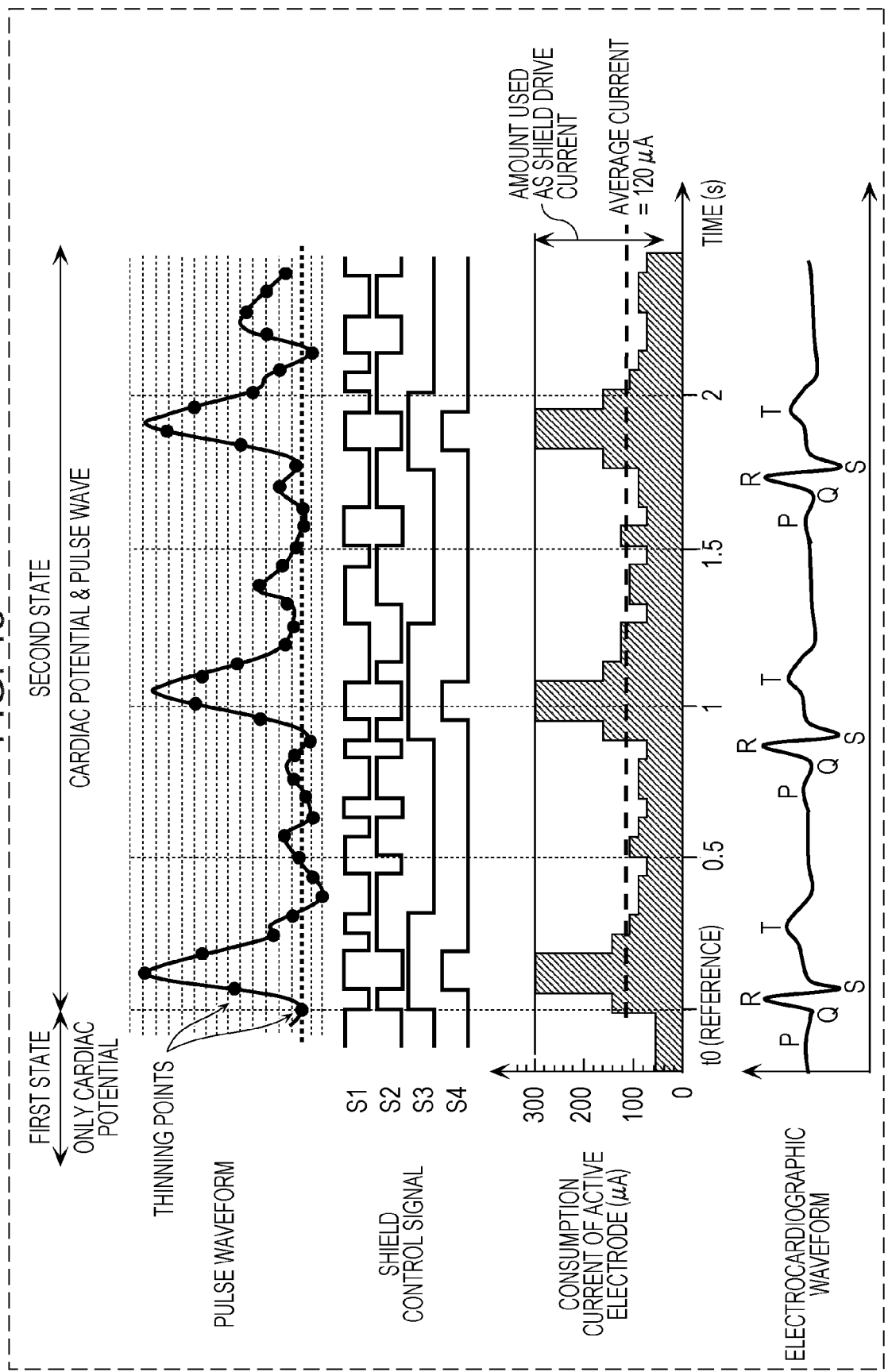

ELECTRONIC DEVICE, METHOD FOR CONTROLLING ELECTRONIC DEVICE, AND RECORDING MEDIUM

BACKGROUND

1. Technical Field

The present disclosure relates to an electronic device, a method for controlling an electronic device, and a recording medium.

2. Description of the Related Art

As an information processing system, a biomedical electrode in which a shield is disposed so as to cover around an interconnect wire extending from an electrode to a buffer (an impedance conversion circuit) has been developed (refer to, for example, Japanese Unexamined Patent Application Publication No. 2012-120705).

SUMMARY

However, according to the configuration described in Japanese Unexamined Patent Application Publication No. 2012-120705, a situation in which the signal quality of the cardiac potential deteriorates in simultaneous measurement of the pulse wave and the cardiac potential may occur. More specifically, in the case of simultaneous measurement of a pulse wave and a cardiac potential with the configuration described in Japanese Unexamined Patent Application Publication No. 2012-120705, a subject continuously touches one electrode with a finger of one hand and the other electrode with a finger of the other hand to measure the cardiac potential and further touches a pulse wave sensor disposed in the vicinity of one of the electrodes with a finger of one hand to measure the pulse wave. In this case, the electrode and the interconnect wire extending from the electrode to the buffer pick up noise resulting from the influence of a pulse wave signal detected by the pulse wave sensor and, thus, the signal quality of the cardiac potential deteriorates.

One non-limiting and exemplary embodiment provides an electronic device, a method for controlling an electronic device, and a recording medium capable of reducing deterioration of the signal quality of a cardiac potential in simultaneous measurement of the pulse wave and the cardiac potential.

In one general aspect, the techniques disclosed here feature electronic device including a first electrode and a second electrode used to measure a cardiac potential, a pulse wave sensor disposed closer to the first electrode than to the second electrode, where the pulse wave sensor measures a pulse wave, a first amplifying unit that amplifies a signal acquired by the first electrode, a first interconnect wire that electrically connects the first electrode to a terminal of the first amplifying unit, where the first interconnect wire transmits the signal, a first shield member that shields the first electrode and the first interconnect wire, a shield potential controller including a first buffer circuit and a second buffer circuit, and a drive current of the second buffer circuit is larger than a drive current of the first buffer circuit. Before a predetermined time point when the pulse wave sensor measures the pulse wave, the shield potential controller starts applying, to the first shield member, a first generation signal generated by the first buffer circuit on the basis of the signal. At the predetermined time point, the shield potential controller starts applying, to the first shield member, a second generation signal generated by the second buffer circuit on the basis of the signal.

According to the present disclosure, deterioration of the signal quality of the cardiac potential in simultaneous measurement of the pulse wave and cardiac potential can be reduced.

These general and specific aspects may be implemented as a system, a method, an integrated circuit, a computer program, or a computer-readable recording medium, or any combination of an apparatus, a system, a method, an integrated circuit, a computer program, and a computer-readable recording medium. Examples of the computer-readable recording medium include a nonvolatile recording medium, such as a Compact Disc-Read Only Memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIGS. 4A and 4B illustrate examples of the positions of electrodes when the electrodes are mounted on the back surface of the controller;

FIG. 19 is a flowchart illustrating the basic processing performed by the information processing system;

FIG. 20A illustrates the positional relationship between the electrode and a shield member disposed around the electrode according to a first exemplary embodiment;

FIG. 20B illustrates the positional relationship among the electrode, a shield member disposed around the electrode, and the finger of a person according to the first exemplary embodiment;

FIGS. 21A and 21B illustrate the position of the shield member disposed in a wiring layer that is one level lower than the mounting surface of the electrode according to the first exemplary embodiment;

FIG. 31 is a control table denoting the details of control performed by a shield control unit according to the first exemplary embodiment;

FIG. 41 is a control table denoting the details of control performed by a shield control unit according to the second exemplary embodiment;

FIG. 43 illustrates an example of a time-series change in the shield driving capability according to the second exemplary embodiment.

DETAILED DESCRIPTION

Figure 1:
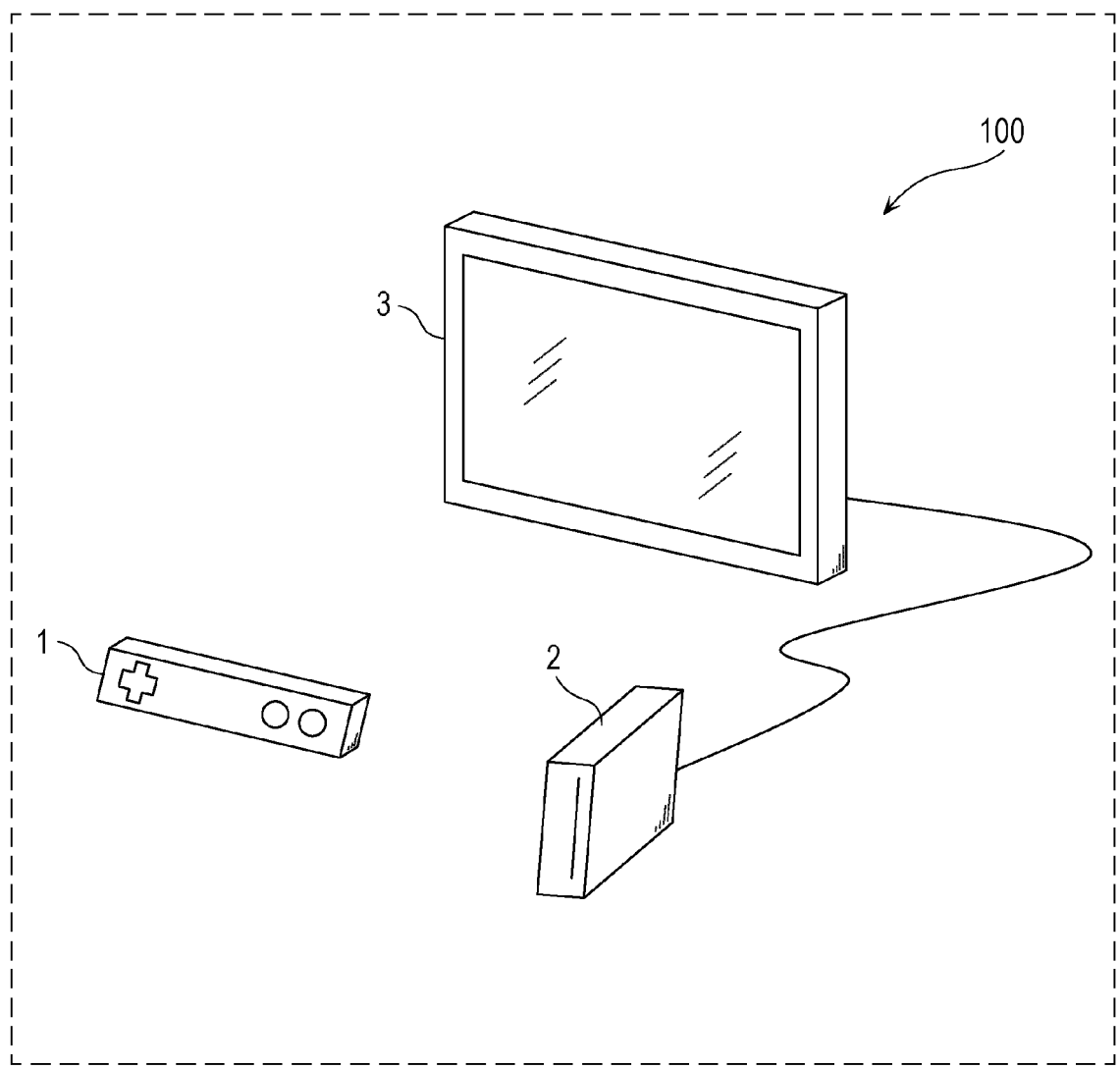
FIG. 1 is an external view illustrating a usage scene of an information processing system.

According to an aspect of the present disclosure, an electronic device includes a first electrode and a second electrode used to measure a cardiac potential, a pulse wave sensor disposed closer to the first electrode than to the second electrode, where the pulse wave sensor measures a pulse wave, a first amplifying unit that amplifies a signal acquired by the first electrode, a first interconnect wire that electrically connects the first electrode to a terminal of the first amplifying unit, where the first interconnect wire transmits the signal, a first shield member that shields the first electrode and the first interconnect wire, a shield potential controller including a first buffer circuit and a second buffer circuit, and a drive current of the second buffer circuit is larger than a drive current of the first buffer circuit. Before a predetermined time point when the pulse wave sensor measures the pulse wave, the shield potential controller starts applying, to the first shield member, a first generation signal generated by the first buffer circuit on the basis of the signal. At the predetermined time point, the shield potential controller starts applying, to the first shield member, a second generation signal generated by the second buffer circuit on the basis of the signal.

In the electronic device according to the above aspect, the first electrode and the first interconnect wire are shielded by the shield member driven by the second buffer circuit having a relatively large drive current at the time point when the pulse wave sensor is measured. In this manner, noise coupled into the cardiac potential acquired by the electrode due to the pulse wave signal is reduced. The reason is as follows. The amplitude of the pulse wave signal is larger than the amplitude of the cardiac potential, and the cardiac potential and the pulse wave signal have different in phases. Consequently, the first electrode and the first interconnect wire can be shielded by using an output line of a buffer having a relatively large drive current (for example, 1 mA). In this way, the electronic device can reduce the deterioration of the quality of the cardiac potential signal that occurs in simultaneous measurement of the pulse wave and the cardiac potential. For example, the first electrode is brought into contact with one of the fingers of a person to acquire the signal, and the pulse wave sensor detects the pulse wave from the finger. According to the above aspect, the electronic device can acquire a signal for electrocardiogram measurement and a signal for pulse wave measurement from a single finger of the person. Thus, the deterioration of the quality of the cardiac potential signal in simultaneous measurement of the pulse wave and the cardiac potential is reduced. In addition, since the number of measurement points required by the electronic device can be reduced, the usability of the electronic device can be increased.

For example, the pulse wave sensor includes a light emitting unit and a light emission control circuit that generates a light emission control signal used to control light emission of the light emitting unit. The shield potential controller acquires the light emission control signal and defines a time point when the acquired light emission control signal causes the light emitting unit to emit light as the predetermined time point.

In the electronic device according to the above aspect, the first electrode and the first interconnect wire are shielded by a shield member driven by a second buffer circuit having a relatively large drive current at the time point when the light emitting unit emits light. When the pulse wave sensor measures the pulse wave, the light emitting unit emits light. Accordingly, the electronic device can easily obtain the time point of measurement of the pulse wave by using the time point of light emission by the light emitting unit. Thus, deterioration of the quality of the cardiac potential signal can be reduced in simultaneous measurement of the pulse wave and the cardiac potential.

For example, the shield potential controller defines, as the predetermined time point, a time point when a new pulse wave peak is to be detected, and the time point is predicted on the basis of the pulse wave detected by the pulse wave sensor.

In the electronic device according to the above aspect, the first electrode and the first interconnect wire are shielded by a shield member driven by a second buffer circuit having a relatively large drive current at a time point when a new pulse wave peak is to be detected. Since the pulse wave measured by the pulse wave sensor has a periodic pattern, the time point at which a new pulse wave peak is measured can be predicted to some extent when the pulse wave is continuously measured. In this manner, the electronic device can easily obtain the measurement time point of the pulse wave by using the time point at which a new pulse wave peak is measured and reduce deterioration of the quality of the cardiac potential signal in simultaneous measurement of the pulse wave and the cardiac potential.

For example, the electronic device further includes a casing gripped by the fingers of a person. The first electrode and the pulse wave sensor are disposed side by side in a first direction so as to be exposed to the outside of the casing. The first electrode is circular in plan view, and the following expression is satisfied:

$$F \geq X + D + Y$$

where in plan view, X represents the diameter of the first electrode, Y represents the length of the pulse wave sensor in the first direction, D represents a minimum distance to be maintained between the first electrode and the pulse wave sensor, and F represents the diameter of a normal substantially circular contact area between the finger and the casing.

According to the above aspect, when a person grips an electronic device naturally, in other words, as usual, a human finger is in contact with both the electrode and the pulse wave sensor. Thus, simultaneous measurement of the pulse wave and the cardiac potential is performed properly.

For example, the first shield member may have an annular shape concentric with the first electrode in plan view. The distance between the first electrode and the first shield member is greater than or equal to twice a minimum value of a wiring interval on a substrate, and the width of the first shield member in a diameter direction in plan view is greater than or equal to three times the minimum value of the wiring interval on the substrate.

According to the above aspect, the electronic device can be made compact while maintaining the shielding effect of the electrode by the shield member. As a result, when a person grips the electronic device naturally, one of the fingers of the person is in contact with both the electrode and the pulse wave sensor more easily. Thus, simultaneous measurement of the pulse wave and the cardiac potential is properly performed.

For example, the electronic device may further includes a reception unit that receives one of a first instruction and a second instruction. The first instruction instructs the shield potential controller to apply the first generation signal to the first shield member without applying the second generation signal to the first shield member, and the second instruction instructs the shield potential controller to apply the first generation signal to the first shield member and further apply the second generation signal to the first shield member.

According to the above aspect, the electronic device can control the shielding effect by the shield member on the basis of an instruction from the user. As a result, simultaneous measurement of the pulse wave and cardiac potential can be performed at the time point that reflects the intention of the user.

For example, each of the first electrode and the second electrode is an active electrode.

According to the above aspect, by using the active electrode, the electronic device can measure the cardiac potential with accuracy higher than in measurement without using an active electrode.

For example, the electronic device further includes a signal receiving unit connected to the first amplifying unit by using a second interconnect wire. The signal receiving unit receives a signal amplified by the first amplifying unit. The shield potential controller further applies at least one of the first generation signal and the second generation signal to a second shield member that shields the second interconnect wire.

According to the above aspect, by using a buffer circuit, the electronic device also drives the shield member of the interconnect wire through which the signal amplified by the first amplifying unit is transmitted. Thus, an effect that the cardiac potential acquired by the electrode is accurately transmitted by the interconnect wire can be obtained.

For example, the shield potential controller includes a switching unit, and the switching unit includes a first switch that switches whether the first generation signal is applied to the second shield member and a second switch that switches whether the second generation signal is applied to the second shield member.

According to the above aspect, the electronic device is capable of controlling whether the shield member of the interconnect wire through which the signal amplified by the first amplifying unit is transmitted is driven by the buffer circuit. Thus, control can be performed such that the driving is performed when necessary. By performing driving when necessary, the effect of reduction in power consumption can be provided.

For example, the shield potential controller further includes a second amplifying unit that amplifies a second signal acquired by the second electrode, a third interconnect wire that electrically connects the second electrode to a terminal of the second amplifying unit and transmits the second signal, and a third shield member that shields the second electrode and the third interconnect wire. The shield potential controller further includes a third buffer circuit and a fourth buffer circuit having a drive current that is larger than a drive current of the third buffer circuit. The shield potential controller applies, to the third shield member, a third generation signal generated by the third buffer circuit on a basis of the second signal, and/or the shield potential controller applies, to the third shield member, a fourth generation signal generated by the fourth buffer circuit on a basis of the second signal at the predetermined time point.

In the electronic device according to the above aspect, in addition to the first electrode and the first interconnect wire, the second electrode and the third interconnect wire are shielded by a shield member driven by a second buffer circuit having a relatively large drive current. As a result, noise coupled into the cardiac potential acquired by the electrode due to the pulse wave signal can be reduced more.

According to another aspect of the present disclosure, a method for controlling an electronic device is provided. The electronic device includes a first electrode and a second electrode used to measure a cardiac potential, a pulse wave sensor disposed closer to the first electrode than to the second electrode, where the pulse wave sensor measures a pulse wave, a first amplifying unit that amplifies a signal acquired by the first electrode, a first interconnect wire that electrically connects the first electrode to a terminal of the first amplifying unit, where the first interconnect wire transmits the signal, a first shield member that shields the first electrode and the first interconnect wire, a shield potential controller including a first buffer circuit and a second buffer circuit, and a drive current of the second buffer circuit is larger than a drive current of the first buffer circuit. The method includes obtaining a predetermined time point when the pulse wave sensor measures the pulse wave, starting applying, to the first shield member, a first generation signal generated by the first buffer circuit on the basis of the signal before the predetermined time point, and starting applying, to the first shield member, a second generation signal generated by the second buffer circuit on a basis of the signal at the predetermined time point.

Thus, the same effect as that of the above-described electronic device can be obtained.

According to still another aspect of the present disclosure, a program that causes a computer to perform a method for controlling an electronic device is provided. The electronic device includes a first electrode and a second electrode used to measure a cardiac potential, a pulse wave sensor disposed closer to the first electrode than to the second electrode, where the pulse wave sensor measures a pulse wave, a first amplifying unit that amplifies a signal acquired by the first electrode, a first interconnect wire that electrically connects the first electrode to a terminal of the first amplifying unit, where the first interconnect wire transmits the signal, a first shield member that shields the first electrode and the first interconnect wire, a shield potential controller including a first buffer circuit and a second buffer circuit, and a drive current of the second buffer circuit is larger than a drive current of the first buffer circuit. The method includes obtaining a predetermined time point when the pulse wave sensor measures the pulse wave, starting applying, to the first shield member, a first generation signal generated by the first buffer circuit on a basis of the signal before the predetermined time point, and starting applying, to the first shield member, a second generation signal generated by the second buffer circuit on a basis of the signal at the predetermined time point.

Thus, the same effect as that of the above-described electronic device can be obtained.

Furthermore, according to yet still another aspect of the present disclosure, a non-transitory computer-readable recording medium storing a program that causes a computer to perform a method for controlling an electronic device is provided. The electronic device includes a first electrode and a second electrode used to measure a cardiac potential, a pulse wave sensor disposed closer to the first electrode than to the second electrode, where the pulse wave sensor detects a pulse wave, a first amplifying unit that amplifies a signal acquired by the first electrode, a first interconnect wire that electrically connects the first electrode to a terminal of the first amplifying unit, where the first interconnect wire transmits the signal, a first shield member that shields the first electrode and the first interconnect wire, and a shield potential controller including a first buffer circuit and a second buffer circuit having a drive current that is larger than a drive current of the first buffer circuit. The method includes obtaining a predetermined time point when the pulse wave sensor measures the pulse wave, starting applying, to the first shield member, a first generation signal generated by the first buffer circuit on a basis of the signal before the predetermined time point, and starting applying, to the first shield member, a second generation signal generated by the second buffer circuit on a basis of the signal at the predetermined time point. Thus, the same effect as that of the above-described electronic device can be obtained.

It should be noted that general or specific embodiments may be implemented as a system, a method, an integrated circuit, a computer program, a storage medium, such as a computer-readable CD-ROM, or any selective combination thereof.

Exemplary embodiments are described in detail below with reference to the accompanying drawings.

Note that each of the embodiments described below is a general or specific example of the present disclosure. A value, a shape, a material, a constituent element, the positions and the connection form of the constituent elements, steps, and the sequence of steps described in the embodiments are only examples and shall not be construed as limiting the scope of the present disclosure. In addition, among the constituent elements in the embodiments described below, the constituent element that does not appear in an independent claim, which has the broadest scope, is described as an optional constituent element.

First Exemplary Embodiment

According to a first exemplary embodiment, an electronic device, a method for controlling an electronic device, and a recording medium capable of reducing deterioration of the signal quality of the cardiac potential in simultaneous measurement of the pulse wave and the cardiac potential are described.

Description of Information Processing System Including Controller and Information Processing Apparatus FIG. 1 is an external view illustrating a usage scene of an information processing system 100. As illustrated in FIG. 1, the information processing system 100 includes a controller 1, an information processing apparatus 2, and a display device 3. The controller 1, the information processing apparatus 2, and the display device 3 are connected so as to be capable of communicating with one another wired or wirelessly. The controller 1, the information processing apparatus 2, and the display device 3 transmit and receive information. The information processing system 100 corresponds to an electronic device.

The controller 1 includes an input device that receives operation information input by a user to operate the information processing system 100. The user inputs the operation information for performing a desired process.

The information processing apparatus 2 receives the operation information input to the controller 1 and performs a predetermined process. As used herein, the term "predetermined process" refers to any application, such as a game, health management, or learning application, performed by a home computer.

The display device 3 displays the result of the process performed by the information processing apparatus 2. More specifically, the term "displaying" as used herein refers to outputting an image onto a display. Note that the display device 3 may output, to the display, the image and/or speech from the loudspeaker. Hereinafter, the term "displaying" refers to a concept including presentation of the result of process in the form of an image and presentation of the result of process in the form of speech.

Shape of Controller

Figure 2B:
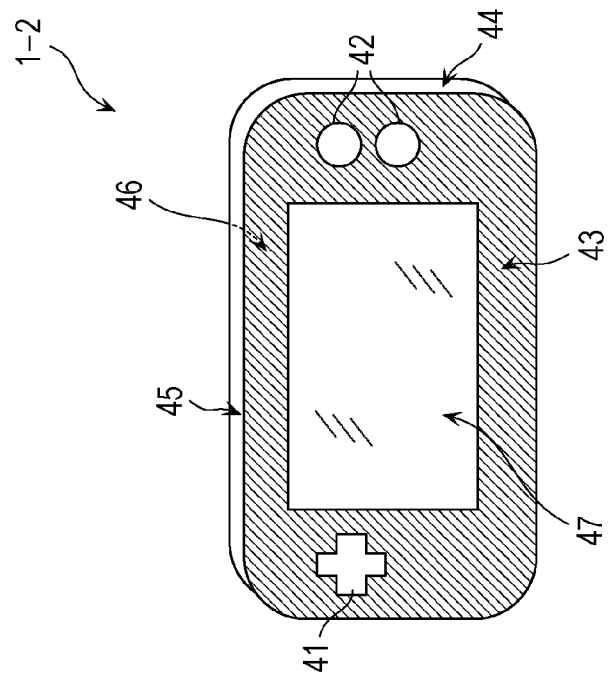
FIGS. 2A and 2B are external views illustrating examples of the shape of a controller.
Figure 2A:
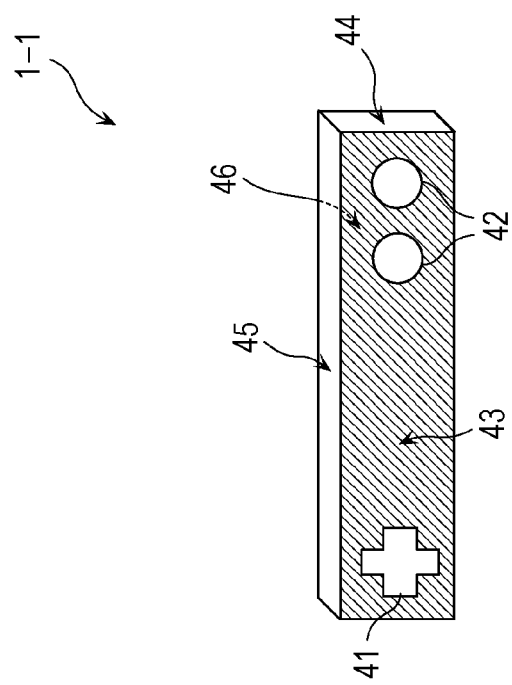

FIGS. 2A and 2B are external views illustrating examples of the shape of the controller 1. For example, the user grips the controller 1 with both hands and inputs operation information to the controller 1. A specific example of the shape of the controller 1 is a stick-type controller 1-1 (refer to FIG. 2A) and a pad-type controller 1-2 (refer to FIG. 2B).

The stick-type controller 1-1 illustrated in FIG. 2A has a stick form having a shape of a horizontally long bar. The user grips both sides of the controller 1-1 with both hands, operates an operation button 41 with the thumb of the left hand, and operates an operation button 42 with the thumb of the right hand. The operation button 41 has, for example, an arrow key that enables the user to input selection of one of the upward, downward, leftward and rightward directions, and the operation button 42 has, for example, two buttons for performing two types of control.

The pad-type controller 1-2 illustrated in FIG. 2B has a plate-like pad shape. The user grips both sides of the controller 1-2 with both hands, operates the operation button 41 with the thumb of the left hand, and operates the operation button 42 with the thumb of the right hand. The controller 1-2 includes a display unit 47 in the center. The display unit 47 is a display device that displays the conditions of the operation and/or the result of the process of an application.

Figure 3:
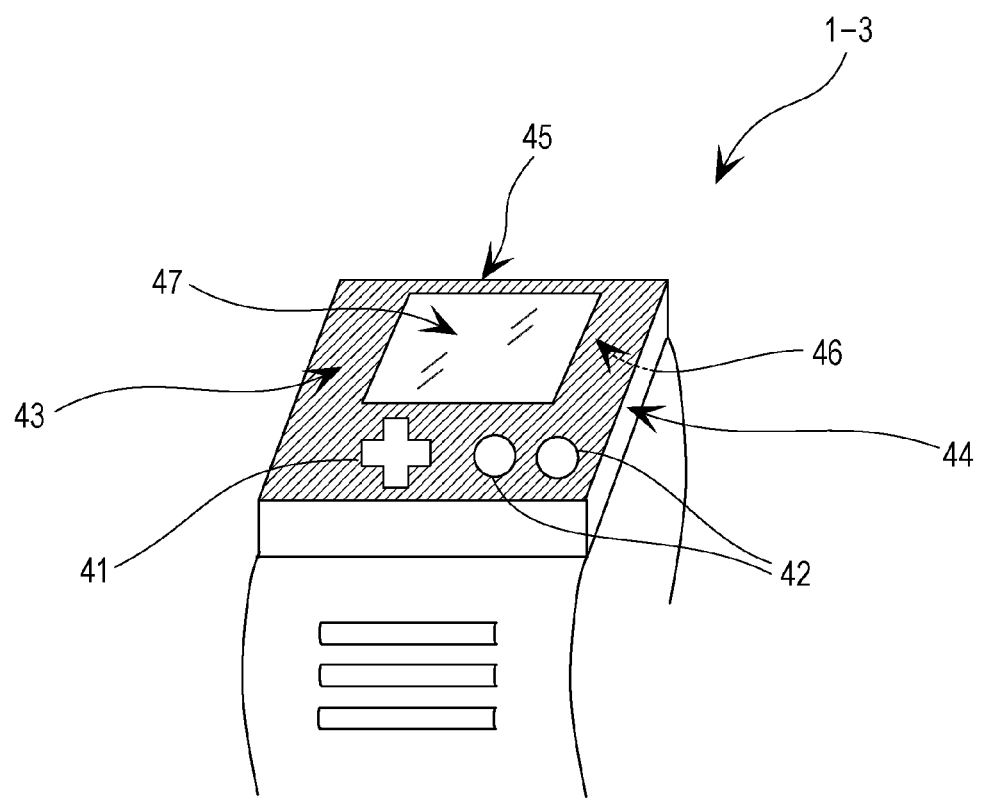
FIG. 3 is an external view illustrating another example of the shape of a controller.

FIG. 3 is an external view illustrating another example of the shape of the controller 1. Another example of the form of the controller 1 is a wristband-type controller 1-3 (refer to FIG. 3). As illustrated in FIG. 3, the wristband-type controller 1-3 has a wristband or wristwatch shape. For example, the user wears the controller 1-3 on the wrist of the left hand and operates the controller 1-3 with the right hand. More specifically, the user operates the operation button 41 and the operation button 42 with the thumb of the right hand. The controller 1-3 has a display unit 47 in the center. The display unit 47 is a display device that displays the conditions of the operation and the result of the process of an application.

Definition of Surfaces

The definitions of the surfaces used herein are described below with reference to FIGS. 2A and 2B.

The controller 1 has an operation surface 43, a left side surface (not illustrated), a right side surface 44, an upper side surface 45, a lower side surface (not illustrated), and a back surface 46.

For example, in the stick-type controller 1-1 (refer to FIG. 2A), the operation surface 43 is a surface having the operation button 41 and the operation button 42 disposed thereon. The surfaces on the left side, the right side, the upper side, and the lower side are referred to as the "left side surface" (not illustrated), the "right side surface 44", the upper side surface 45, and the lower side surface (not illustrated), respectively, as viewed toward the operation surface 43. The surface opposed to the operation surface 43 is referred to as the "back surface 46".

The same definitions (e.g., the operation surface 43) apply to the pad-type controller 1-2 and the wristband-type controller 1-3.

When the display unit 47 is configured in the form of a touch panel display, the operation buttons 41 and 42 may be displayed on the display unit 47. In this case, the surface having the display unit 47 of the controller 1 is defined as the operation surface 43. Alternatively, a screen of the display unit 47 for displaying information may be defined as the operation surface 43. A controller having the operation surface 43 configured by a touch panel display is typically a smartphone or a tablet computer. Such a smartphone or tablet computer that executes the application software for operating the information processing apparatus 2 has a function that is the same as the function of the controller 1 having the hardware-based operation button 41 and operation button 42. As used herein, the controller having the hardware-based operation buttons 41 and 42 and the controller having software-based operation buttons 41 and 42 (an operation input display) are collectively referred to as an "electronic device".

In the case where the operation surface 43, the left side surface (not illustrated), the right side surface 44, the upper side surface 45, the lower side surface (not illustrated), and the back surface 46 are formed as a single surface, each of the left side surface (not illustrated), the right side surface 44, the upper side surface 45, the lower side surface (not illustrated), and the back surface 46 is a portion of the single surface defined by the positional relationship with the operation surface 43.

The same definitions (e.g., the operation surface 43) can apply to the wristband-type controller 1-3 illustrated in FIG. 3. The controller having the operation surface 43 configured by a touch panel display is typically a smart watch.

Positions of Electrodes and Pulse Wave Sensor

The positions of the biopotential measuring electrode and the pulse wave sensor disposed on the controller 1 are described below.

FIGS. 4A and 4B illustrate examples of the positions of the electrodes when the electrodes are mounted on the back surface of the controller. FIGS. 4A and 4B illustrate examples of biomedical signal measuring electrodes 48 and 49 and a pulse wave sensor 61 mounted on the back surface 46 of the controllers 1-1 and 1-2, respectively.

At least a plurality of electrodes are mounted on the controller 1 in order to measure a biopotential signal. The biopotential signal is a signal indicating the potential difference between a plurality of positions at which the user (more specifically, the skin of the user) are in contact with a controller. An example of the biopotential signal is a potential difference between one of the fingers of the right hand of the user and one of the fingers of the left hand of the user, and examples of the biopotential signal include a biomedical signal derived from electrocardiogram. The controller 1 further includes the pulse wave sensor 61 having at least one light emitting diode (LED) and at least one photodetector (PD). An example of a pulse wave signal is a biomedical signal derived from a pulse wave obtained by photoelectrically converting the LED light reflected from one of the fingers of the right hand by using the PD. The pulse wave sensor is disposed in the vicinity of any one of the electrodes. In the examples illustrated in FIGS. 4A and 4B, the pulse wave sensor 61 is disposed in the vicinity of the electrode 49.

The user grips the stick-type controller 1-1 with both hands and operates the operation buttons 41 and 42 with the left and right thumbs, respectively. At this time, the user needs to resist depressing the operation buttons 41 and 42 with the thumbs by supporting the back surface 46 with the index finger or the middle finger. To support the back surface 46, the index or middle finger of the user is in contact with the back surface 46.

The controller 1-1 has the electrodes and the pulse wave sensor at positions at which the fingers of the user are in contact with the controller 1-1 when the user grips the controller 1-1.

For example, the back surface 46 has a plurality of electrodes and a pulse wave sensor in a predetermined range A including the positions corresponding to the positions of the operation buttons 41 and 42 on the operation surface 43. An example of the predetermined range A is a range including the position corresponding to the positions of the operation buttons 41 and 42, that is, the positions on the back surface 46 that face the back of the operation buttons 41 and 42 and is a range in which the fingers of the user can be placed to support the controller 1-1.

The stick-type controller 1-1 illustrated in FIG. 4A has the electrode 48 for the left hand disposed in a portion which the fingers of the left hand touch. In addition, the stick-type controller 1-1 has the electrode 49 for the right hand and the pulse wave sensor 61 disposed in a portion which the fingers of the right hand touch.

Similarly, in the case of the pad-type controller 1-2 illustrated in FIG. 4B, the user supports the back surface 46 with the fingers to resist depressing the operation buttons 41 and 42 disposed on the operation surface 43. The controller 1-2 includes the electrode 48 for the left hand, the electrode 49 for the right hand, and the pulse wave sensor 61 at positions on the back surface 46 at which the user touches to support the back surface 46. By mounting the electrodes and the pulse wave sensor at these positions, the information processing system 100 can continuously measure the biopotential and the pulse wave signal at the same time even when the user is operating the controller 1-2.

Figure 5A:
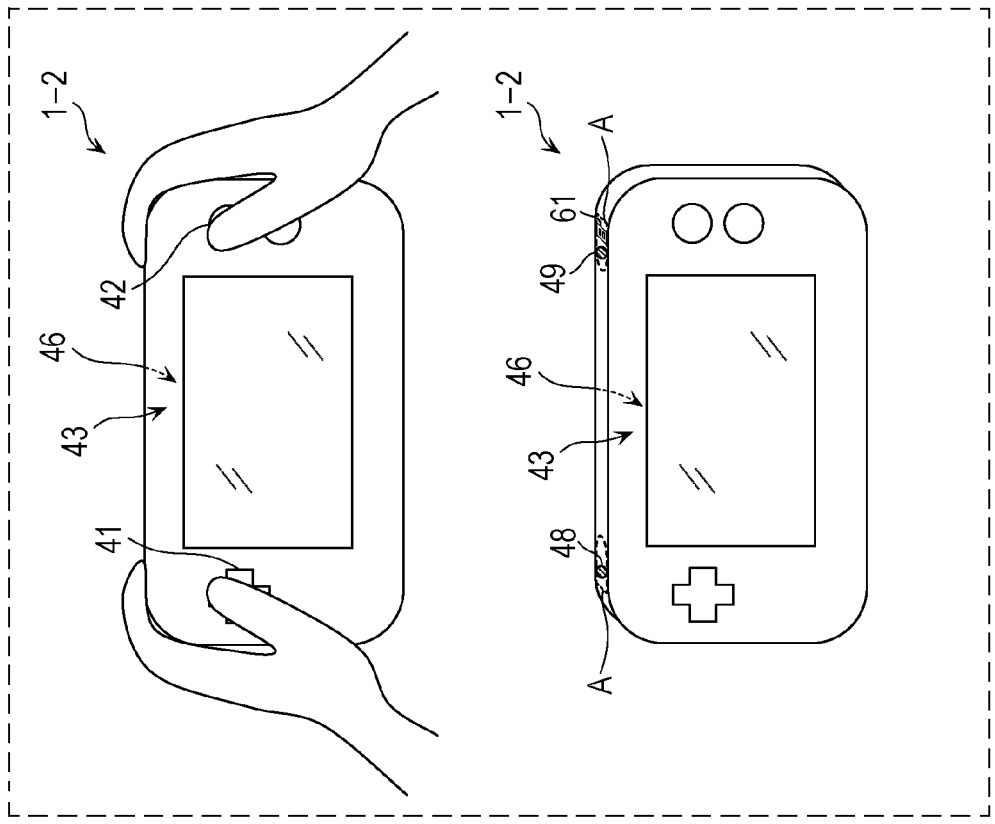
FIGS. 5A and 5B illustrate examples of the positions of the electrodes when the electrodes are mounted on the upper side surface of the controller.
Figure 5B:
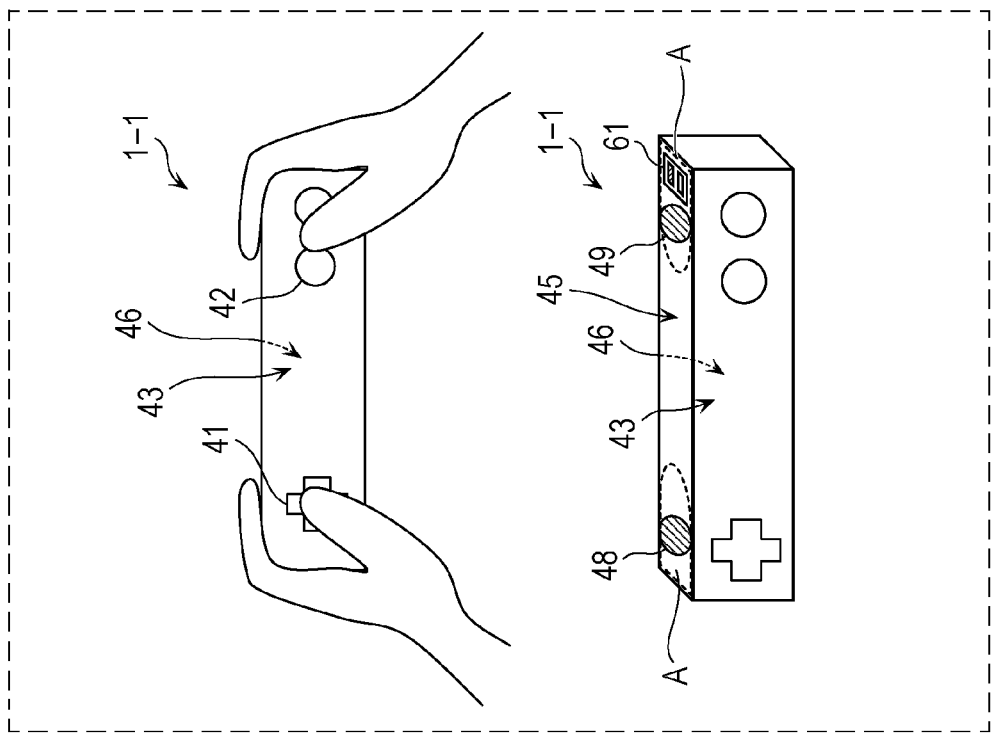

FIGS. 5A and 5B illustrate examples of the positions of the electrodes when the electrodes are mounted on the upper surface of the controller. FIG. 5A illustrates the positions of the electrodes in the controller 1-1, and FIG. 5B illustrates the positions of the electrodes in the controller 1-2.

FIGS. 5A and 5B illustrate examples in which the biomedical signal measuring electrodes and the pulse wave sensor are mounted on the upper side surface 45 of the controller 1. To hold the stick-type controller 1-1 with both hands, the user can place the index fingers on the upper side surface 45 and place the middle fingers, the ring fingers, and the little fingers on the back surface 46. In this case, in addition to supporting the back surface 46 to resist depressing the operation buttons 41 and 42, the user may place the index fingers on the upper side surface 45. The controller 1-1 may define predetermined ranges A in the upper side surface 45 on which the index fingers are placed and may have the electrode 48 for the left hand, the electrode 49 for the right hand, and the pulse wave sensor 61 in the ranges A.

Similarly, to hold the pad-type controller 1-2, the index fingers can be placed on the upper side surface 45. Therefore, the controller 1-2 may have the electrode 48 for the left hand, the electrode 49 for the right hand, and the pulse wave sensor 61 on the upper side surface 45.

Figure 6:
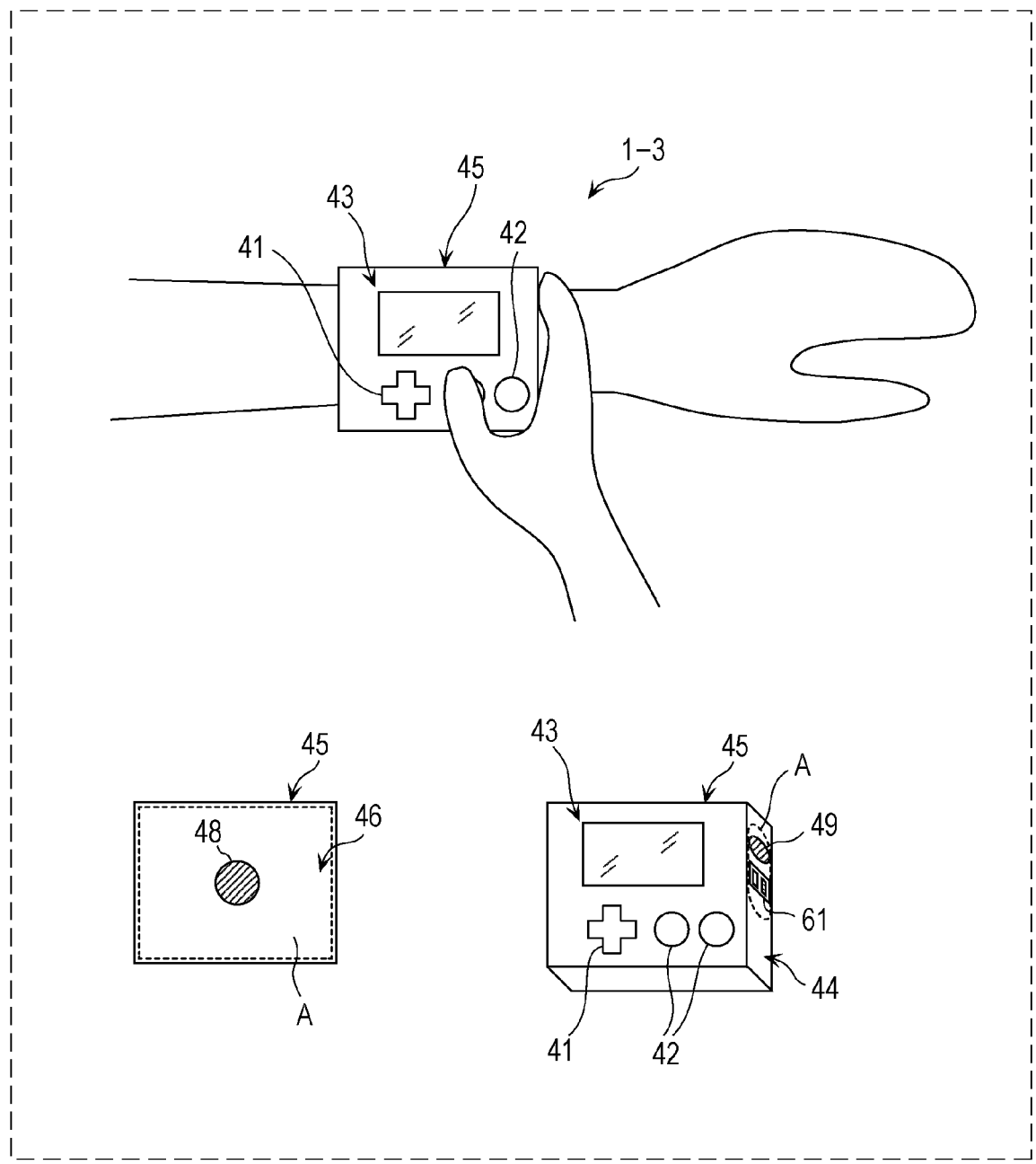
FIG. 6 illustrates an example of the positions of the electrodes when the electrodes are mounted on the back surface and the right side surface of the controller.

FIG. 6 illustrates an example in which the wristband-type controller 1-3 has one of the biomedical signal measuring electrodes mounted on the back surface 46 and the other biomedical signal measuring electrode and the pulse wave sensor mounted on the right side surface 44.

The user wears the wristband-type controller 1-3 on the wrist of the left hand and secures the controller 1-3 to the wrist of the left hand with a band (not illustrated) at this time. Thus, the electrode 48 for the left hand disposed on the back surface 46 is brought into contact with the wrist of the left hand. An example of the predetermined range A in which the electrode 48 for the left hand is placed is a range where the back surface 46 is in contact with the wrist of the left hand.

The user operates the operation buttons 41 and 42 with the thumb of the right hand. At this time, the user needs to resist depressing the operation buttons 41 and 42 with the thumb of the right hand by supporting the right side surface 44 with any one of the index finger, the middle finger, and the ring finger of the right hand. To support the right side surface 44, any one of the index finger, the middle finger, or the ring finger of the right hand of the user is brought into contact with the right side surface 44.

The controller 1-3 has the electrode 49 for the right hand and the pulse wave sensor 61 at the positions with which the fingers of the user are in contact when the user supports the right side surface 44 with any one of the index finger, the middle finger, and the ring finger of the right hand of the user.

An example of the predetermined range A in which the electrode 49 for the right hand and the pulse wave sensor 61 are mounted is a range including a position in the right side surface 44 at which the right side surface 44 is in contact with the upper side surface 45 and is a range in which the finger of the user can be placed to support the controller 1-3. By mounting the electrode 49 at this position, continuous measurement of the biopotential and the pulse wave signal is available even when the user is operating the controller 1-3.

Figure 7:
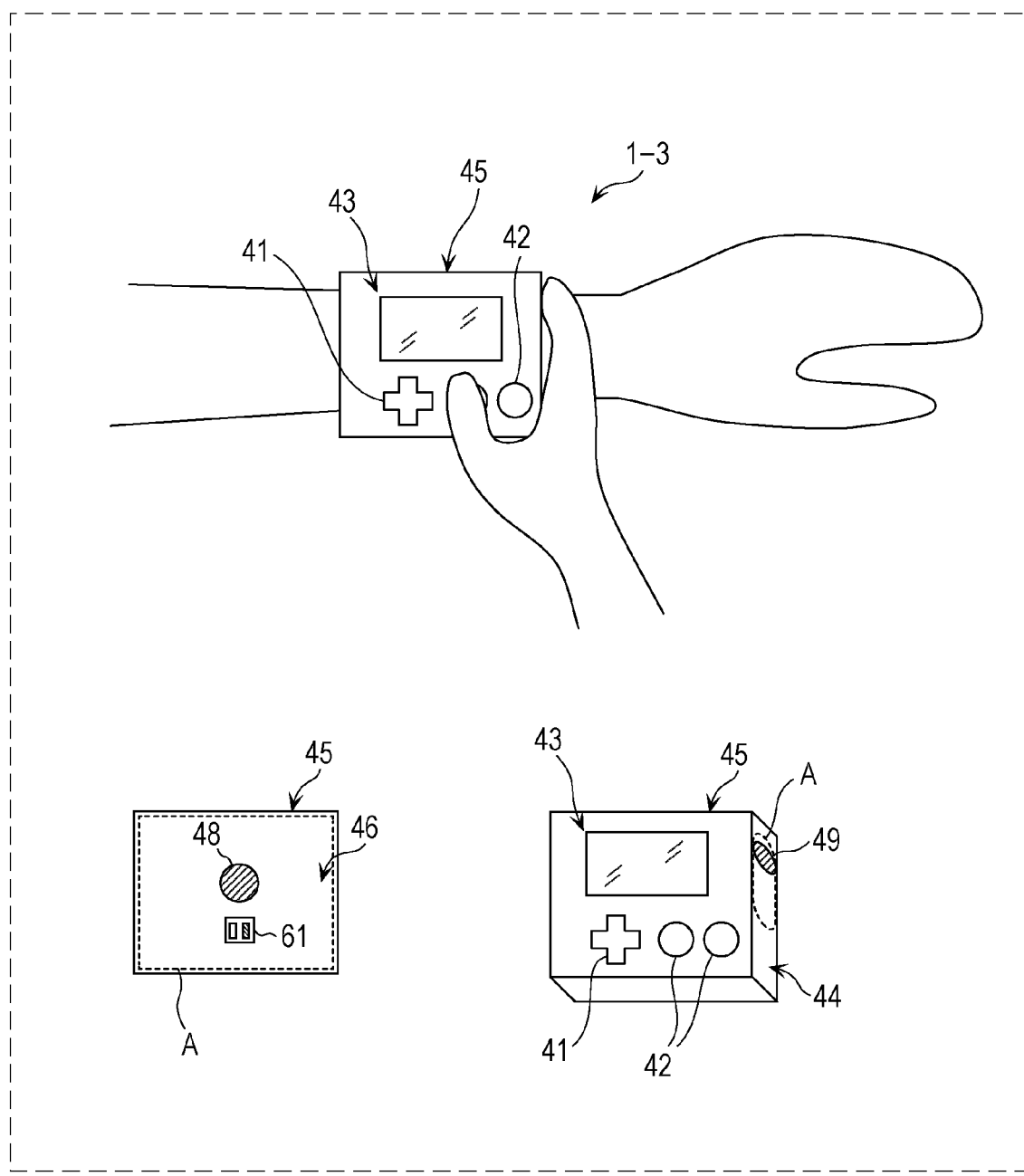
FIG. 7 illustrates another example of the positions of the electrodes when the electrodes are mounted on the back surface and the right side surface of the controller.

Instead of mounting the pulse wave sensor 61 at a position in the vicinity of the electrode 49 for the right hand, the pulse wave sensor 61 may be mounted at a position in the vicinity of the electrode 48 for the left hand, as illustrated in another example in FIG. 7. By mounting the pulse wave sensor 61 at this position, the pulse wave sensor 61 can be maintained in contact with the wrist of the left hand. Accordingly, even when the user is operating the controller 1-3 with the finger of the right hand, continued measurement of the pulse wave signal is enabled.

Figure 8:
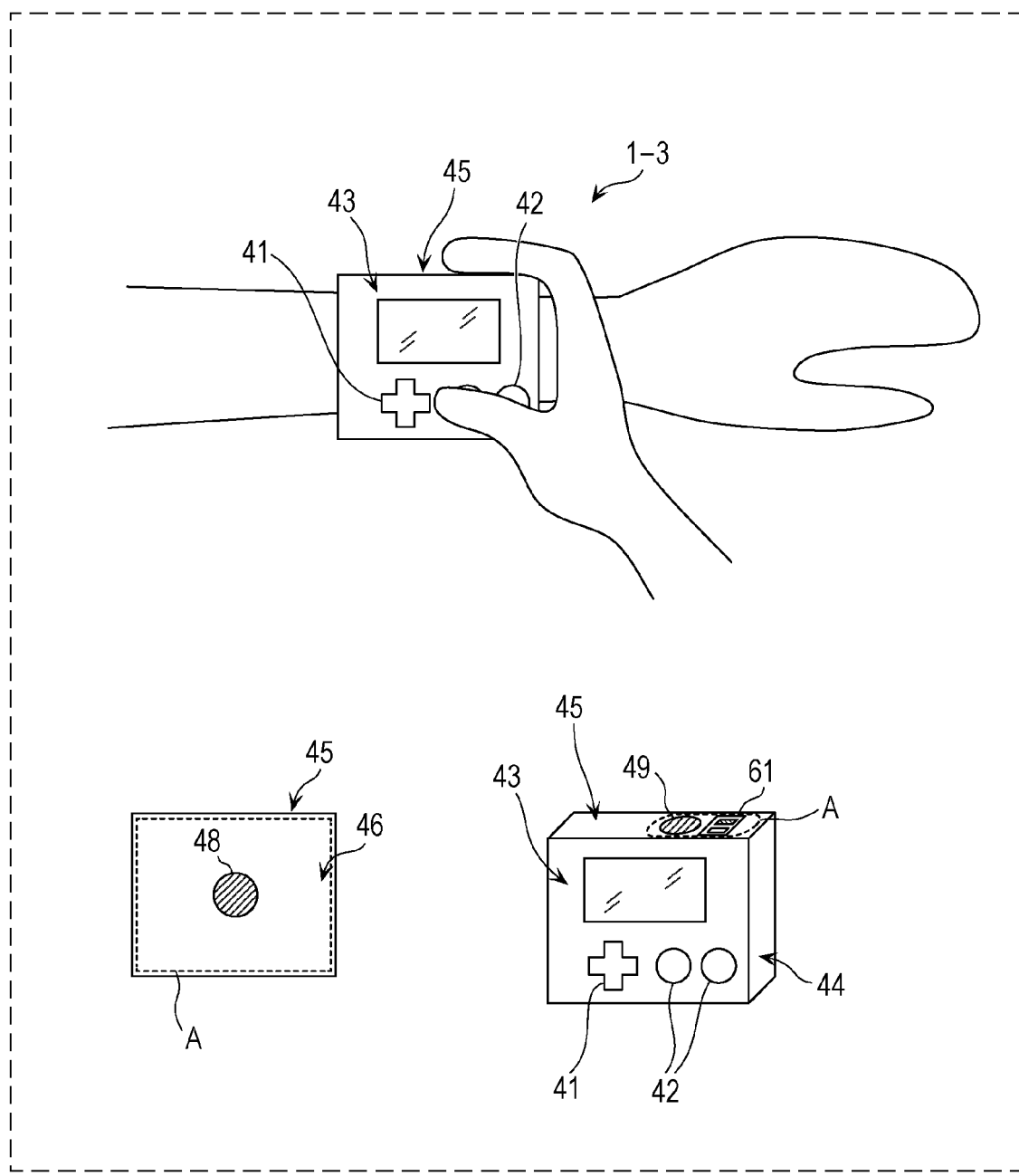
FIG. 8 illustrates an example of the positions of the electrodes when the electrodes are mounted on the back surface and the upper side surface of the controller.

FIG. 8 illustrates an example in which the biomedical signal measuring electrodes are mounted on the back surface 46 and the upper side surface 45 of the wristband-type controller 1-3.

The user wears the wristband-type controller 1-3 on the wrist of the left hand and secures the wristband-type controller 1-3 to the wrist of the left hand with a band (not illustrated) at this time. Thus, the electrode 48 for the left hand mounted on the back surface 46 is brought into contact with the wrist of the left hand.

The user operates the operation buttons 41 and 42 with the thumb of the right hand. At this time, the user needs to resist depressing the operation buttons 41 and 42 with the thumb of the right hand by supporting the upper side surface 45 with any one of the index finger, the middle finger, and the ring finger of the right hand. To support the upper side surface 45, any one of the index finger, the middle finger, and the ring finger of the right hand of the user is brought into contact with the upper side surface 45.

The controller 1-3 has an electrode 49 for the right hand at a position at which the finger of the user is in contact with the controller when the user supports the upper side surface 45 of the controller 1-3 with any one of the index finger, the middle finger, and the ring finger of the right hand of the user.

An example of a predetermined range A in which the right-hand electrode 49 and the pulse wave sensor 61 are mounted is a range including the position at which the operation button 41 is projected onto the upper side surface 45. By mounting the electrode at this position, continuous measurement of the biomedical signal and the pulse wave signal can be performed even during operation.

Note that the pulse wave sensor 61 may be mounted at a position (not illustrated) in the vicinity of the electrode 48 for the left hand instead of being mounted at a position in the vicinity of the electrode 49 for the right hand. By mounting a pulse wave sensor at this position, continuous measurement of the pulse wave signal can be performed even when the user is operating the controller 1-3.

Shape and Number of Electrodes

Figure 9:
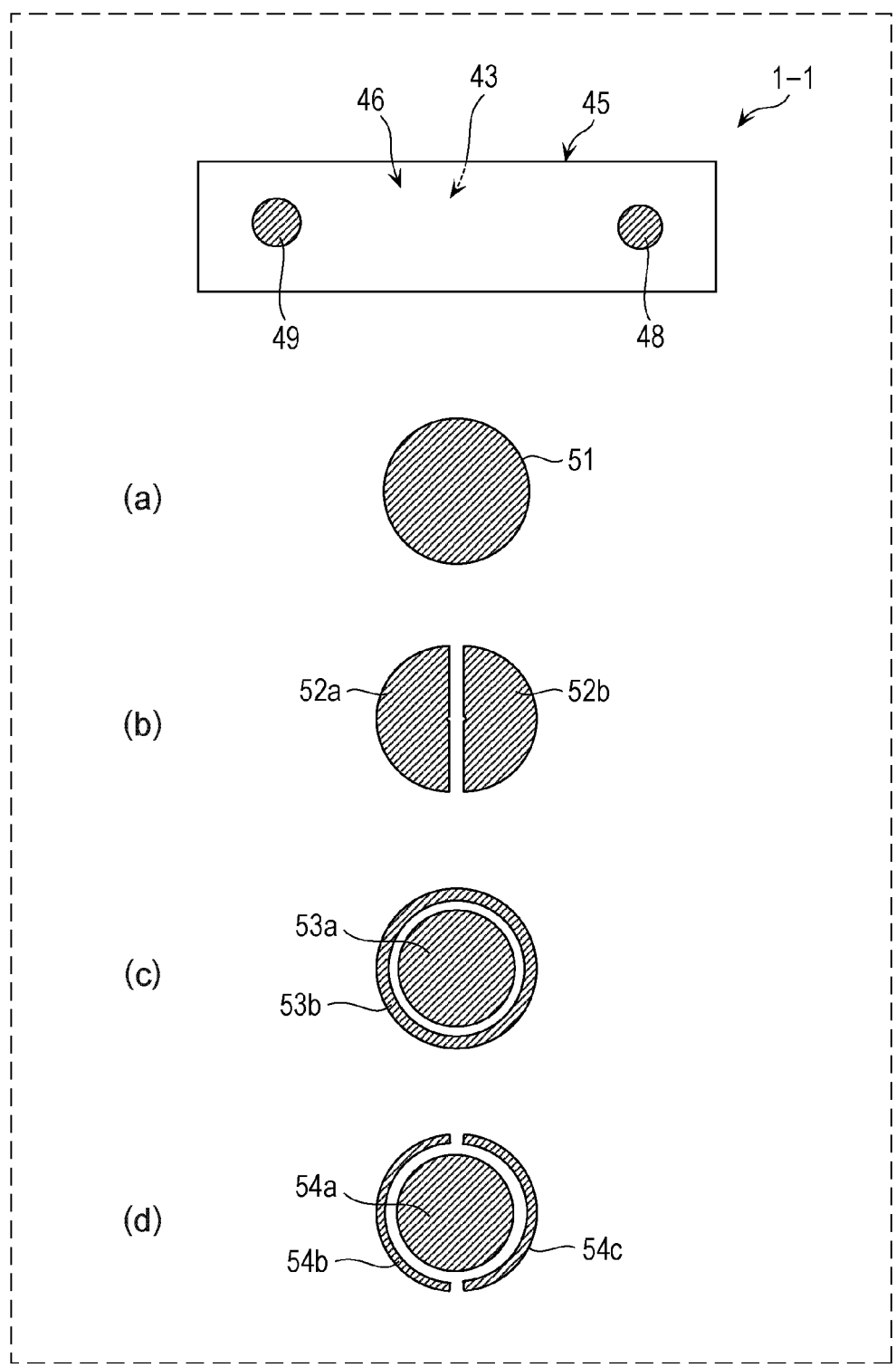
FIG. 9 illustrates examples of the shape and the number of electrodes in the controller.

FIG. 9 illustrates examples of the shape and the number of electrodes in the controller 1. FIGS. 9(a) to 9(d) illustrate examples of the shape of the electrode. The electrode is made of a conductive substance. An example of the material of the electrode is gold or silver. Alternatively, the material of the electrode may be silver-silver chloride. This is because silver-silver chloride is less likely to be polarized when it is in contact with the living body.

The electrode 51 illustrated in FIG. 9(a) is a circular electrode similar to an electrode used for medical use. In addition to the circular electrode 51 illustrated in FIG. 9(a), an electrode having one of a variety of shapes may be used in accordance with an application. In addition, the number of electrodes that are in contact with one hand is not limited to one. More specifically, one of the following configurations may be employed: (1) a configuration including two semicircular electrodes 52a and 52b as illustrated in FIG. 9(b), (2) a configuration including a circular electrode 53a and an annular electrode 53b disposed so as to be concentric with the circular electrode 53a as illustrated in FIG. 9(c), and (3) a configuration including a circular electrode 54a and two semicircular annular electrodes 54b and 54c as illustrated in FIG. 9(d).

Figure 10A:
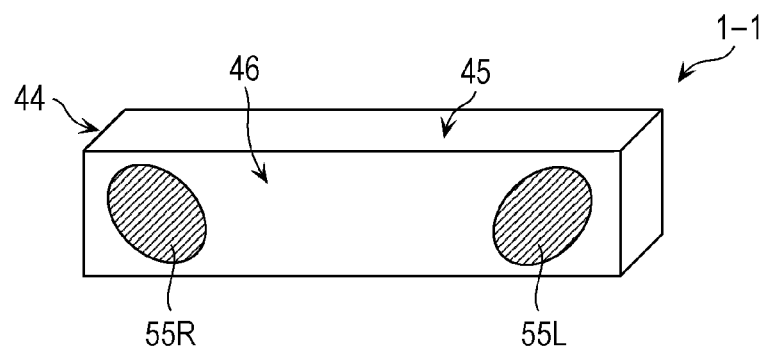
FIGS. 10A to 10C illustrate other examples of the shape of the electrode in the controller.
Figure 10B:
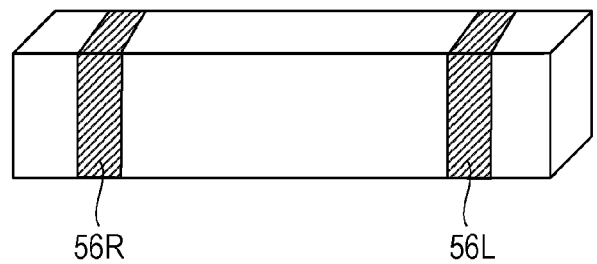
Figure 10C:

In addition, as illustrated in FIGS. 10A to 10O, the shape of the electrode is not limited to a circular shape. More specifically, as illustrated in FIG. 10A, relatively large electrodes 55L and 55R that cover a relatively wide area with which the hand is likely to be in contact may be mounted such that the contact is maintained at all times. Alternatively, a configuration including belt-like electrodes 56L and 56R extending on the upper side surface 45 and the lower side surface in addition to the back surface 46 (refer to FIG. 10B) or a configuration including a plurality of belt-like electrodes (electrodes 57La and 57Lb and electrodes 57Ra and 57Rb) (refer to FIG. 10O) may be employed. In this manner, even when the user holds the controller in a variety of ways, the biopotential signal can be measured.

Shape of Pulse Wave Sensor and Number of LEDs

FIGS. 11(a) to 11(e) illustrate examples of the shape of the pulse wave sensor 61.

Figure 11:
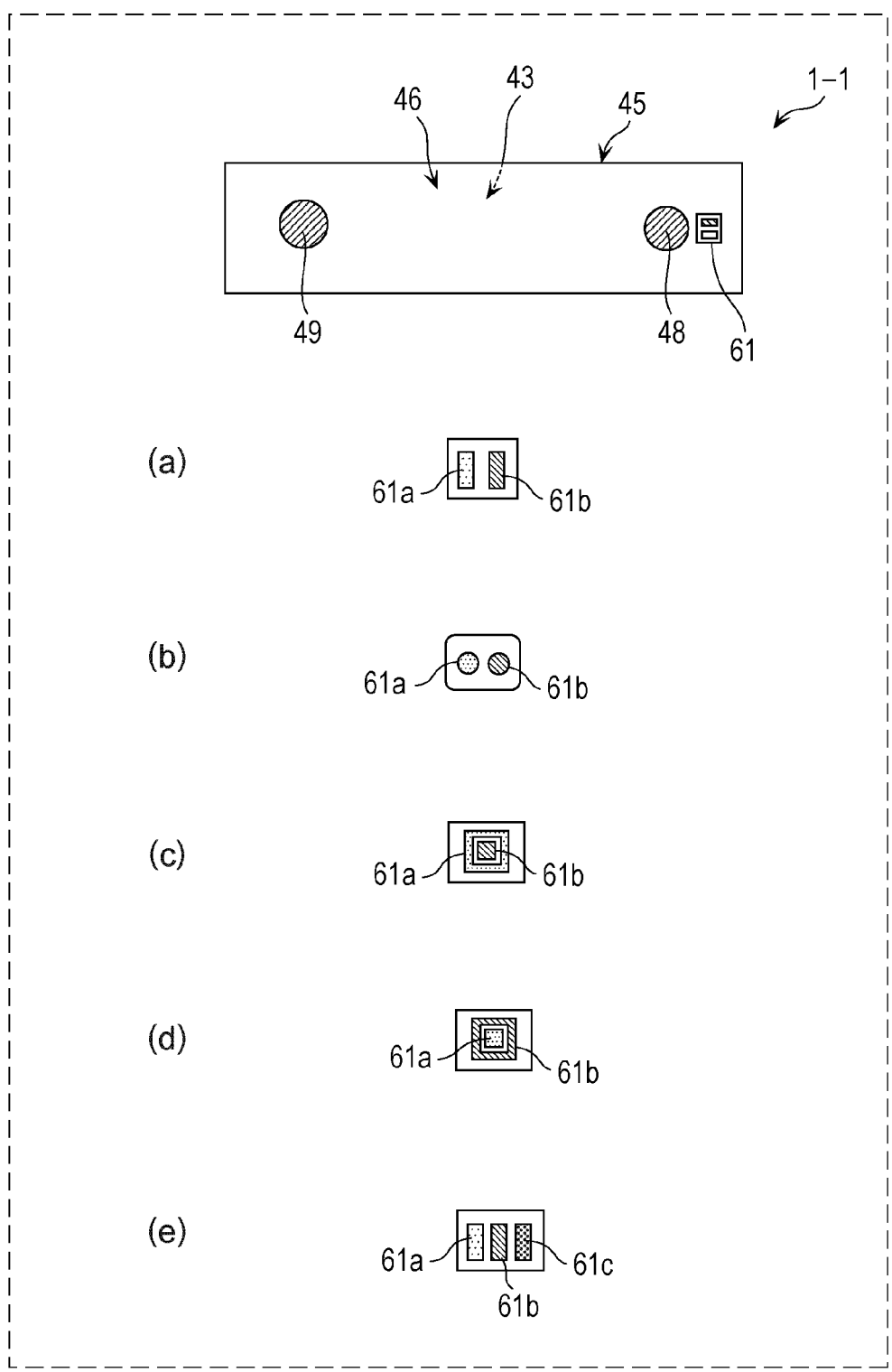
FIG. 11 illustrates examples of the shapes of a pulse wave sensor and the number of LEDs in the controller.

The pulse wave sensor 61 in FIG. 11(a) is configured to include a rectangular LED 61a and a rectangular PD 61b arranged side by side. In addition to the above configuration, various shapes of the pulse wave sensor 61 can be employed in accordance with an application. For example, one of the following configurations may be employed: (1) a configuration including a circular LED 61a and a circular PD 61b arranged side by side as illustrated in FIG. 11(b), (2) a configuration including a PD 61b surrounded by an annular LED 61a as illustrated in FIG. 11(c), (3) a configuration including an LED 61a surrounded by an annular PD 61b as illustrated in FIG. 11(d), and (4) a configuration including two LEDs 61a and 61c arranged with a PD 61b therebetween. In the above configuration (4), the LED 61a may be a red LED, and the LED 61c may be an infrared LED, for example.

Positional Relationship Between Electrode and Pulse Wave Sensor

Figure 12A:
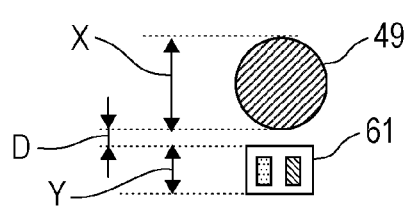
FIGS. 12A and 12B illustrate the positional relationship between the electrode and the pulse wave sensor.
Figure 12B:
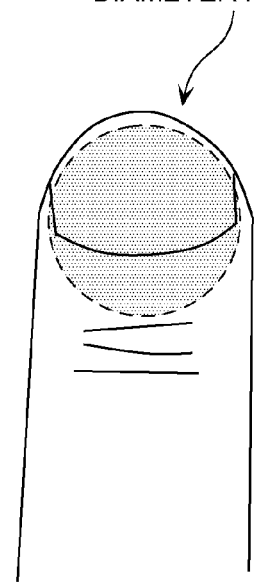

FIGS. 12A and 12B illustrate the relative positional relationship between the electrode 49 and the pulse wave sensor 61 illustrated in FIGS. 4A and 4B. In this example, the electrode 49 is circular in shape, and each of the LED 61a and the PD 61b of the pulse wave sensor 61 is rectangular in shape.

When an adult male touches the upper side surface 45 with the tip of the middle finger, the contact area between the user and the controller 1 is substantially circular in shape with a diameter of about 14 mm. The size of the contact area between the controller 1 and each of the index finger and the ring finger of the adult male is substantially the same as the size of the contact area between the controller 1 and the middle finger. The electrode for an adult female or child may be configured to have a size smaller than the size for the adult male by a predetermined value in accordance with the size of the hand.

The size of the electrode is determined under presumption that the contact range of each of the index finger, the middle finger, and the ring finger is circular with a diameter F=14 mm. More specifically, a diameter X of the circular electrode 49 is 6 mm, and a length Y of the pulse wave sensor 61 in a direction perpendicular to the arrangement direction of the LED 61a and the PD 61b (that is, the longitudinal direction in FIGS. 12A and 12B) is 3 mm. Here, the direction perpendicular to the alignment direction of the LED 61a and the PD 61b coincides with the direction from the first joint of the finger to the fingertip.

The positional relationship is such that when the finger is brought into contact with the center of the electrode 49, the LED 61a and PD 61b of the pulse wave sensor 61 are in contact with the finger. That is, the electrode 49 and the pulse wave sensor 61 are positioned within a predetermined area. Here, the distance between the electrode 49 and the pulse wave sensor 61 is determined by the dimensions of the electrode 49.

Let X be the diameter of the electrode 49. Let Y be the length of the pulse wave sensor 61 in a direction parallel to the LED 61a and the PD 61b, and let D be the distance between the electrode 49 and the pulse wave sensor 61. Then, the following expression may be satisfied:

$$F \geq X + D + Y \quad (1)$$

For example, if F=14 mm, X=6 mm, D=1 mm, and Y=3 mm, expression (1) is satisfied.

The dimensions of the electrode may be those obtained by reducing or enlarging the above-described dimensions on the basis of the actual contact area of the finger.

Measurement Time of Biopotential and Pulse Wave

Figure 13:
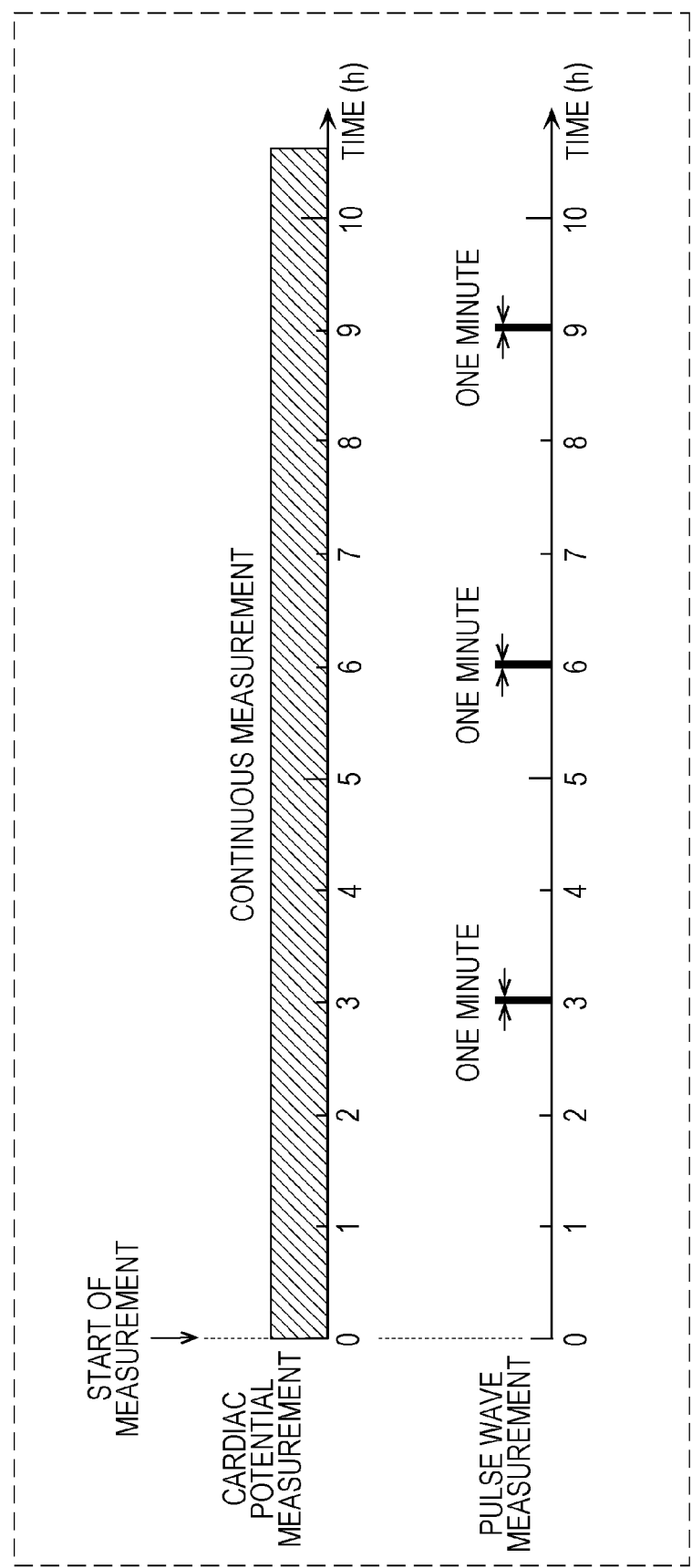
FIG. 13 illustrates an example of the measurement time of the cardiac potential and the pulse wave.

FIG. 13 illustrates an example of the measurement times of the biopotential and the pulse wave. As illustrated in FIG. 13, the cardiac potential is continuously measured by the user by using the electrodes. At this time, the pulse wave is measured by using the pulse wave sensor at intervals of several hours, as illustrated in FIG. 13. More specifically, for example, the pulse wave is measured for 1 minute at intervals of 3 hours.

Figure 14:
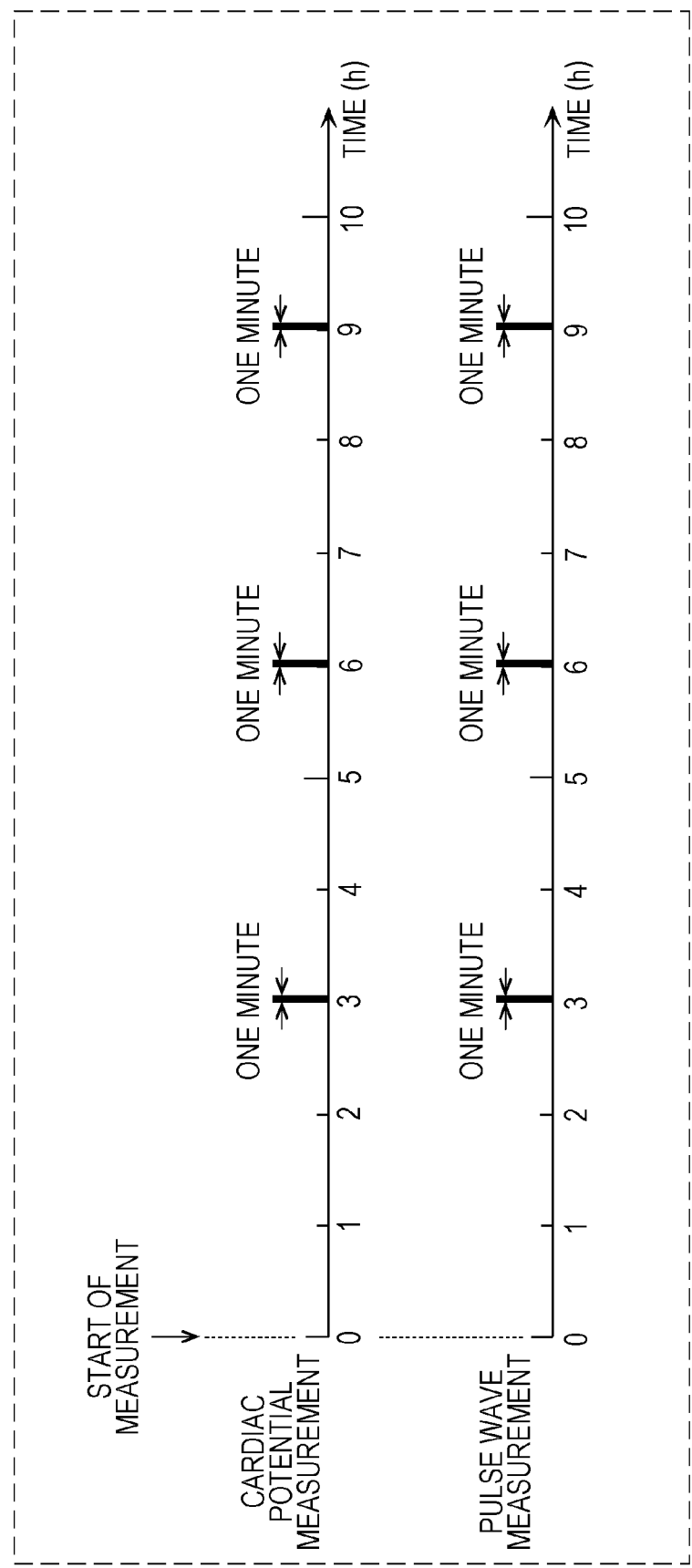
FIG. 14 illustrates another example of the measurement time of the cardiac potential and the pulse wave.

FIG. 14 illustrates another example of the measurement time of the biomedical signal and the pulse wave. The cardiac potential and the pulse wave are measured at the same time by using the biopotential measuring electrode 49 and the pulse wave sensor 61. The measurement is performed on the index finger of the right hand of the user from the time the user grips the wristband-type controller 1-3 illustrated in FIG. 6 (a reference time) at intervals of several hours. More specifically, for example, the cardiac potential and the pulse wave are measured at the same time for 1 minute at intervals of 3 hours.

System Configuration Diagram

Figure 15:
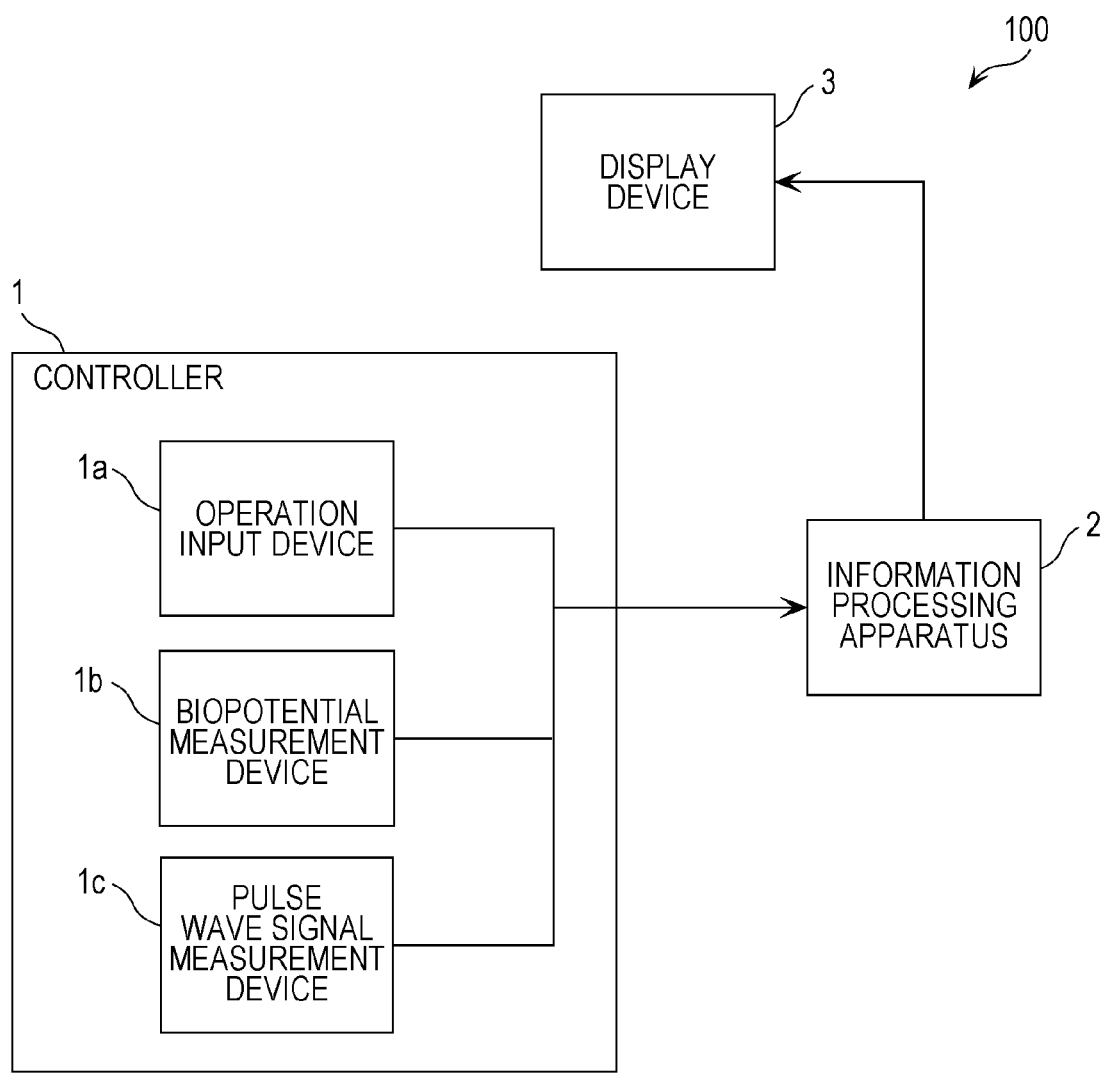
FIG. 15 is a block diagram of the system configuration of the information processing system.

FIG. 15 illustrates the system configuration of the information processing system 100. The controller 1 includes an operation input device 1a, a biopotential measurement device 1b, and a pulse wave signal measurement device 1c.

The controller 1 measures the operation input from the user and the biopotential and the pulse wave signal when the user operates the controller 1. The information including the measured biopotential and pulse wave signal is sent to the information processing apparatus 2.

Upon receiving inputs from the operation input device 1a, the biopotential measurement device 1b, and the pulse wave signal measurement device 1c, the information processing apparatus 2 performs predetermined processing and outputs the result of processing to the display device 3. The controller 1 and the information processing apparatus 2 are connected with each other through wireless or wired communication.

Figure 16:
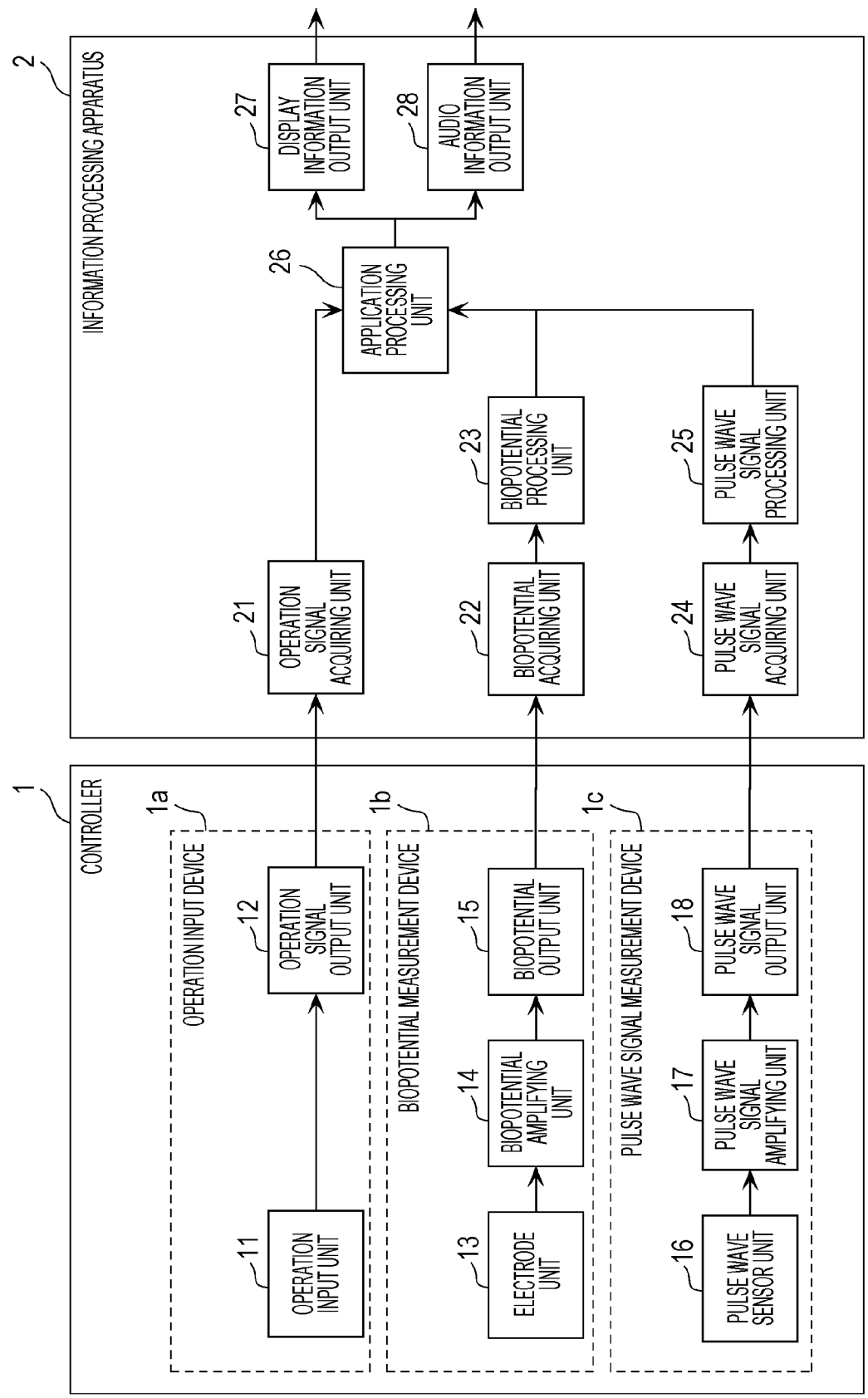
FIG. 16 is a block diagram illustrating the configurations of the controller and an information processing apparatus of the information processing system.

FIG. 16 illustrates the configurations of the controller 1 and the information processing apparatus 2.

The operation input device 1a included in the controller 1 includes an operation input unit 11 and an operation signal output unit 12. The operation input unit 11 is an unit that acquires operation signals input from the operation buttons 41 and 42 and performs a determination process. The acquired operation signals are sent from the operation signal output unit 12 to the information processing apparatus 2.

The biopotential measurement device 1b included in the controller 1 includes an electrode unit 13, a biopotential amplifying unit 14, and a biopotential output unit 15.

The pulse wave signal measurement device 1c included in the controller 1 includes a pulse wave sensor unit 16, a pulse wave signal amplifying unit 17, and a pulse wave signal output unit 18.

The electrode unit 13 includes a plurality of electrodes. The plurality of electrodes are disposed, for example, at positions at which the right hand of the user is in contact with the controller 1 and at positions at which the left hand of the user is in contact with the controller 1.

The biopotential amplifying unit 14 amplifies the biopotential corresponding to the potential difference between the electrodes. For example, the potential difference between the right hand and the left hand is amplified by the biopotential amplifying unit 14. The amplified signal is converted into a digital signal by an A/D converter. Thereafter, the information about the biopotential converted into the digital signals is sent from the biopotential output unit 15 to the information processing apparatus 2.

Note that if a biopotential having a level greater than or equal to a predetermined value can be measured, the biopotential amplifying unit 14 may measure the potentials of the plurality of electrodes without amplifying the biopotentials. Therefore, hereinafter, the biopotential amplifying unit 14 is also referred to as a "biomedical signal measuring unit".

The pulse wave sensor unit 16 includes a pulse wave sensor having an LED and a PD. For example, the pulse wave sensor is disposed at a position at which the right hand of the user is in contact with the controller 1.

The pulse wave signal amplifying unit 17 converts the value of a current flowing through the PD of the pulse wave sensor unit 16 into a voltage signal (also referred to as a "pulse wave signal") and, thereafter, amplifies the value by a predetermined amplification factor. The amplified pulse wave signal is converted into a digital signal by an A/D converter. Information about the pulse wave signal converted into the digital signal is sent from the pulse wave signal output unit 18 to the information processing apparatus 2.

Note that if the pulse wave signal having a signal level greater than or equal to a predetermined value can be measured, the pulse wave signal amplifying unit 17 may convert the value of a current flowing through the PD of the pulse wave sensor into the voltage signal without amplify the pulse wave signal. The pulse wave signal amplifying unit 17 is also referred to as a "pulse wave signal measuring unit".

The information processing apparatus 2 receives the operation input information by using an operation signal acquiring unit 21, receives a source signal of the biopotential by using a biopotential acquiring unit 22 and receives the source signal of the pulse wave signal by using a pulse wave signal acquiring unit 24. In this manner, the information processing apparatus 2 receives the information from the controller 1.

A biopotential processing unit 23 performs the process of extracting the biopotential from the source signal of the biopotential acquired by the biopotential acquiring unit 22. This is because in many cases, it is difficult to use the source signal as useful information about the biopotential. For example, the biopotential processing unit 23 performs a process of, for example, acquiring heartbeat information by detecting a peak from a time-series change in a signal indicating a change in the potential between both hands.

A pulse wave signal processing unit 25 performs a process of extracting a pulse wave signal from the source signal of the pulse wave signal acquired by the pulse wave signal acquiring unit 24. This is because in many cases, it is difficult to use the source signal as useful information about the pulse wave signal. For example, the pulse wave signal processing unit 25 performs a process of, for example, acquiring pulse wave information by detecting a peak from a time-series change in a pulse wave signal.

An application processing unit 26 performs the primary processing of the information processing apparatus 2. Examples of processing performed by the application processing unit 26 include game progress control in a game application, recording, management and display of data in a health management application, and question setting, grading of the answers, and displaying of the result of the grading in a learning application. Note that the processing performed by the application processing unit 26 may include the process of calculating the pulse wave propagation time obtained from the biopotential processing unit 23 and the pulse wave signal processing unit 25 and the process of estimating the blood pressure. The application processing unit 26 accomplishes the processing by receiving an input from the controller 1 and performing a predetermined process.

A display information output unit 27 and an audio information output unit 28 output a visual signal and an audio signal, respectively, in order to provide feedback to the user, the result of the processing performed by the application processing unit 26. The output signal is sent to the display device 3.

The display device 3 displays the signals output from the display information output unit 27 and the audio information output unit 28. In this manner, the signals are presented to the user. Examples of the display device 3 include a television set, a display, or a loudspeaker.

Note that the controller 1 may include the biopotential processing unit 23 and the pulse wave signal processing unit 25. In this case, the information processing apparatus 2 does not include the biopotential processing unit 23 and the pulse wave signal processing unit 25, and the application processing unit 26 receives the biopotentials acquired by the biopotential processing unit 23 and the pulse wave signal acquired by the pulse wave signal processing unit 25.

Hardware Configuration

Figure 17:
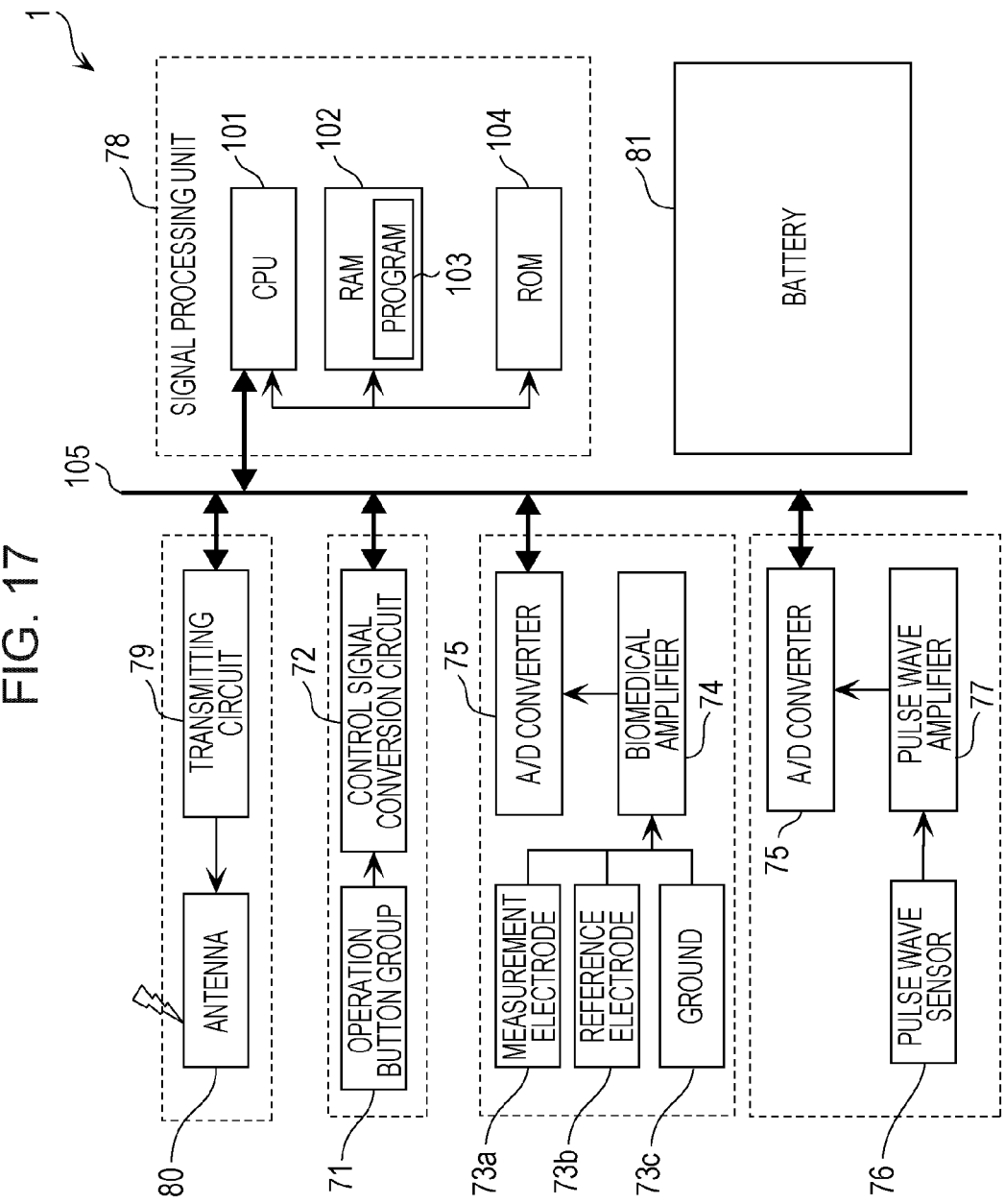
FIG. 17 is a block diagram illustrating the hardware configuration of the controller.

FIG. 17 is a block diagram illustrating the hardware configuration of the controller 1. The controller 1 includes an operation button group 71, a control signal conversion circuit 72, a measuring electrode 73*a*, a reference electrode 73*b*, a ground 73*c*, a biomedical amplifier 74, an A/D converter 75, a pulse wave sensor 76, a pulse wave amplifier 77, a transmitting circuit 79, a signal processing unit 78, an antenna 80, and a battery 81.

Among them, the operation button group 71 and the control signal conversion circuit 72 correspond to the operation input unit 11 illustrated in FIG. 16. In addition, the measuring electrode 73*a*, the reference electrode 73*b*, and the ground 73*c* correspond to the electrode unit 13 illustrated in FIG. 16, and the biomedical amplifier 74 corresponds to the biopotential amplifying unit 14 illustrated in FIG. 16.

Note that the pulse wave signal amplifying unit 17 may be included in the biopotential amplifying unit 14. Note that the A/D converter 75 may be included in the biopotential amplifying unit 14 and/or the pulse wave signal amplifying unit 17.

The signal processing unit 78 includes a central processing unit (CPU) 101, a memory 102, a program 103, and a read only memory (ROM) 104.

The transmitting circuit 79 and the antenna 80 function as the biopotential output unit 15 and/or the operation signal output unit 12 illustrated in FIG. 16. These units are also referred to as an "output unit" or a "transmission unit".

These constituent elements are connected to one another via a bus 105, and can exchange data with one another. In addition, electric power is supplied from the battery 81 to each of the circuits.

The press information regarding each of the buttons in the operation button group 71 is converted by the control signal conversion circuit 72 and is sent to the CPU 101 via the bus 105.

The measuring electrode 73*a*, the reference electrode 73*b*, and the ground 73*c* are connected to the biomedical amplifier 74, and the electrodes are disposed at predetermined positions of the controller. The potential difference between the measuring electrode 73*a* and the reference electrode 73*b* is amplified by the biomedical amplifier 74 and is converted from an analog biopotential signal into a digital signal by the A/D converter 75. Thereafter, the digital signal is sent to the CPU 101 via the bus 105 in the form of a biomedical signal that is processable and transmittable.

The pulse wave amplifier 77 has the pulse wave sensor 76 connected thereto. The pulse wave amplifier 77 is disposed at a predetermined position of the controller 1. The value of a current flowing through the PD of the pulse wave sensor 76 is converted into a voltage signal by the pulse wave amplifier 77 and, thereafter, is amplified and converted from an analog pulse wave signal into a digital signal by the A/D converter 75. The digital signal is sent to the CPU 101 via the bus 105 in the form of the pulse wave signal that is processable and transmittable.

The CPU 101 executes the program 103 stored in the memory 102. The processing procedure indicated by a flowchart (described below) is set forth in the program 103. The controller 1 converts the operation signal, the biopotential signal, and the pulse wave signal in accordance with the program 103 and sends the converted signals to the information processing apparatus 2 via the transmitting circuit 79 and the antenna 80. In some cases, the program 103 is stored in the ROM 104.

Note that the signal processing unit 78, the control signal conversion circuit 72, the transmitting circuit 79, the biomedical amplifier 74, the pulse wave amplifier 77, and the A/D converter 75 may be provided in the form of hardware achieved by incorporating a computer program into a single semiconductor circuit, such as a digital signal processor (DSP). If these elements are integrated into a single semiconductor circuit, the mounting area is advantageously reduced. In addition, the consumed power is advantageously reduced.

Alternatively, the biomedical amplifier 74, the pulse wave amplifier 77, and the A/D converter 75 may be integrated into a single semiconductor circuit. The signal processing unit 78, the control signal conversion circuit 72, and the transmitting circuit 79 may be integrated into another semiconductor circuit. These two semiconductor circuits may be connected to each other within a single package (may be integrated into a system in package (SiP)). In this manner, these elements may be provided in the form of hardware such as a DSP. By producing the above two semiconductor circuits through separate processes, the cost can be reduced more than when the elements are integrated into a single semiconductor circuit.

Figure 18:
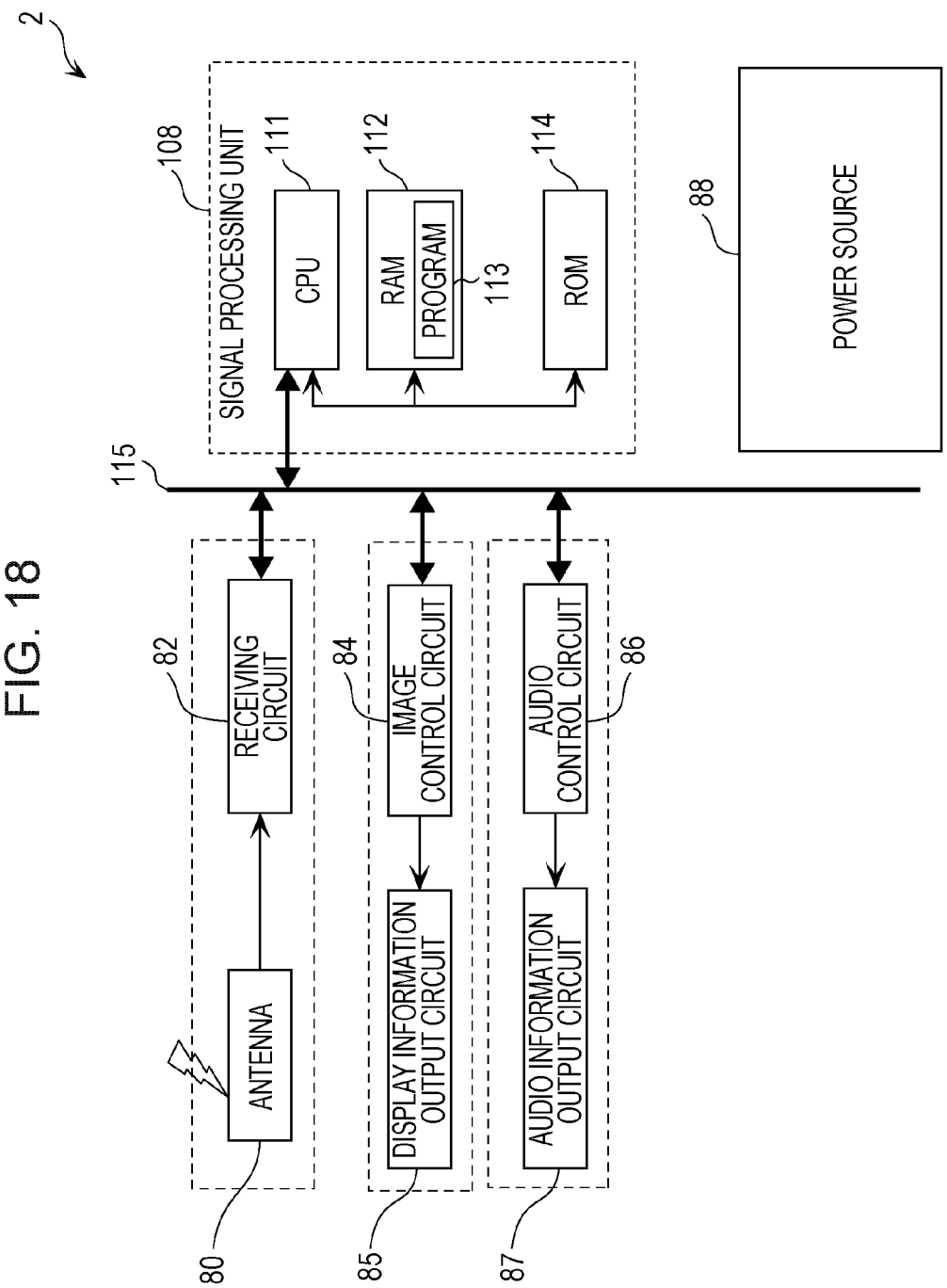
FIG. 18 is a block diagram illustrating the hardware configuration of the information processing apparatus.

FIG. 18 illustrates the hardware configuration of the information processing apparatus 2. The information processing apparatus 2 includes the antenna 80, a receiving circuit 82, a signal processing unit 108, an image control circuit 84, a display information output circuit 85, an audio control circuit 86, an audio information output circuit 87, and a power source 88.

Among them, the antenna 80 and the receiving circuit 82 function as the biopotential acquiring unit 22 and/or the pulse wave signal acquiring unit 24 and/or the operation signal acquiring unit 21 illustrated in FIG. 16. The antenna 80 and the receiving circuit 82 are also referred to as a "receiving unit".

The signal processing unit 108 includes a CPU 111, a memory 112, a program 113, and a ROM 114. The signal processing unit 108 functions as the biopotential processing unit 23 and/or the pulse wave signal processing unit 25 and/or the application processing unit 26 illustrated in FIG. 16. The image control circuit 84 and the display information output circuit 85 function as the display information output unit 27 illustrated in FIG. 16. In addition, the audio control circuit 86 and the audio information output circuit 87 function as the audio information output unit 28 illustrated in FIG. 16. These elements are connected to one another via a bus 115 and can exchange data with one another. Furthermore, electric power is supplied from a power source 88 to the circuits.

The operation information and the biomedical information sent from the controller 1 are received by the receiving circuit 82 via the antenna 80 and are sent to the CPU 111 via the bus 115.

The CPU 111 executes the program 113 stored in the memory 112. The processing procedure indicated by a flowchart described below is set forth in the program 113. The information processing system 100 converts the operation signal, the biopotential signal, and the pulse wave signal in accordance with the program 113 and performs a process for executing a predetermined application. Thus, the information processing system 100 generates a signal in order to provide feedback to the user with an image and/or sound. In some cases, the program 113 is stored in the ROM 114.

The feedback image signal generated by the signal processing unit 108 is output from the display information output circuit 85 via the image control circuit 84. The feedback audio signal is output from the audio information output circuit 87 via the audio control circuit 86.

Note that the signal processing unit 108, the receiving circuit 82, the image control circuit 84, and the audio control circuit 86 may be provided in the form of hardware, such as a DSP, in which a program is incorporated into a single semiconductor circuit. If the circuits are integrated into a single semiconductor circuit, the consumed power can be advantageously reduced.

Overview of Process Flow

FIG. 19 illustrates the process flow of the controller 1 and the information processing apparatus 2. Steps S11 to S18 correspond to the internal process performed by the controller 1, and steps S21 to S28 correspond to the process performed by the information processing apparatus 2.

Step S11

The operation input unit 11 receives an operation input. More specifically, upon receiving the operation input, the operation input unit 11 detects which one of the operation buttons is pressed. An example of the time point when the operation input is received is the time point when the operation button is pressed.

Step S12

The operation signal output unit 12 sends the operation signal corresponding to the operation input received by the operation input unit 11 in step S11 to the information processing apparatus 2 (the operation signal acquiring unit 21).

Step S13

The biopotential amplifying unit 14 measures a biopotential corresponding to a potential difference between the plurality of electrode units 13. For example, the potential difference between the right hand and the left hand of the user that are in contact with the electrode units 13 is measured as the biopotential. In addition, the biopotential amplifying unit 14 amplifies the measured biopotential.

Step S14

The biopotential output unit 15 sends the biopotential amplified in step S13.

Step S15

The pulse wave signal measurement device 1c determines whether the pulse wave is measured. If it is determined that the pulse wave is measured (Yes in step S15), the processing proceeds to step S16. Otherwise (No in step S15), the processing proceeds to step S21.

Step S16

The pulse wave signal measurement device 1c controls the LED by sending an LED control signal to the pulse wave sensor unit 16.

Step S17

The pulse wave signal amplifying unit 17 measures a pulse wave signal corresponding to an electric current flowing through the PD of the pulse wave sensor unit 16. In addition, the pulse wave signal amplifying unit 17 amplifies the measured pulse wave signal.

Step S18

The pulse wave signal output unit 18 sends the pulse wave signal amplified in step S17.

Note that the process in steps S13 and S14 and the process from steps S15 to S18 may be independent processes performed in parallel.

Note that the process in steps S11 and S12 and the process in steps S13 and S14 may be independent processes performed in parallel, that is, all of the processes from step S11 to step S14 need not be performed in sequence.

Note that the process in steps S11 and S12 and the process in steps S15 to S18 may be performed in parallel as independent processes, that is, all of the processes from step S11 to step S18 need not be performed in sequence.

Step S21

The operation signal acquiring unit 21 receives the operation signal sent from the operation signal output unit 12 in step S12.

Step S22

The biopotential acquiring unit 22 receives the source signal of the biomedical signal sent from the biopotential output unit 15 in step S14.

Step S23

The biopotential processing unit 23 extracts the biopotential from the source signal of the biomedical signal received by the biopotential acquiring unit 22 in step S22.

Step S24

The pulse wave signal acquiring unit 24 determines whether the pulse wave signal sent from the pulse wave signal output unit 18 in step S18 is received. If a pulse wave signal is received (Yes in step S24), the processing proceeds to step S25. Otherwise (No in step S24), the processing proceeds to step S27.

Step S25

The pulse wave signal acquiring unit 24 receives the source signal of the pulse wave signal sent from the pulse wave signal output unit 18 in step S24.

Step S26

The pulse wave signal processing unit 25 extracts a pulse wave signal from the source signal of the pulse wave signal received by the pulse wave signal acquiring unit 24 in step S25.

Step S27

The application processing unit 26 receives the operation information sent from the operation signal acquiring unit 21, the biopotential information sent from the biopotential processing unit 23, and the pulse wave information sent from the pulse wave signal processing unit 25. Thereafter, the application processing unit 26 performs predetermined application processing.

Step S28

The display information output unit 27 outputs image information to provide feedback of the result of processing performed by the application processing unit 26 to the user. Note that in this step, at the same time as or instead of the process performed by the display information output unit 27 to output the image information, the audio information output unit 28 may output the audio information to provide feedback of the result of processing performed by the application processing unit 26 to the user. The display device 3 displays the image or outputs the audio information on the basis of the image information output from the display information output unit 27 or the audio information output from the audio information output unit 28 in the present step.

Note that the process in step S22 and step S23 and the process in step S24 to step S26 may be independent processes performed in parallel.

Note that the application processing unit 26 need not use all of the operation information received from the operation signal acquiring unit 21, the biopotential information received from the biopotential processing unit 23, and the pulse wave information received from the pulse wave signal processing unit 25. The application processing unit 26 may perform the processing by using the biopotential signal and the pulse wave signal. Alternatively, the application processing unit 26 may perform the processing by using only the biopotential signal. In that case, step S21 of receiving the operation signal may be removed.

The configurations of the electrode unit 13, the biopotential amplifying unit 14, the pulse wave sensor unit 16, the biopotential processing unit 23, the pulse wave signal processing unit 25, and the application processing unit 26, which are one of the features of the present exemplary embodiment, are described in more detail below.

Electrode Unit and Pulse Wave Sensor Unit

FIG. 20A illustrates an example of the arrangement of the electrode unit 13 and the pulse wave sensor unit 16. FIG. 20B illustrates an example of the positional relationship between the finger of the user and each of the electrode unit 13 and the pulse wave sensor unit 16. In FIG. 20A, a disk-shaped electrode 49 (circular in top view) is disposed at the center of the contact area of the controller 1 in contact with the finger of the user. Note that the electrode 49 may have various shapes in top view, as illustrated in FIG. 9. In addition, the thickness of the electrode 49 is, for example, several 10 µm to several 100 µm.

When the tip of the middle finger of an adult male is in contact with the back surface 46, the area in which the user is in contact with the controller 1 is approximately 14 mm in diameter. Each of the index finger and the ring finger of an adult man is in contact with the controller 1 in substantially the same area as the middle finger. The electrode for an adult female or child may be configured to have a size smaller than the size of the electrode for an adult male by a predetermined degree in accordance with the size of the hand.

The size of the electrode is determined under presumption that the contact area of each of the index finger, the middle finger, and the ring finger is circular with a diameter F=14 mm. More specifically, a diameter X of the circular electrode 49 is 6 mm. A direction perpendicular to the direction in which the LEDs and the PD of the pulse wave sensor 61 are arranged (that is, the longitudinal direction in FIGS. 20A and 20B) corresponds to the first direction. In other words, the first direction is a direction in which a straight line that passes through the center of the circular electrode 49 extends in the longitudinal direction in FIG. 20A.

According to the above-described positional relationship, when the ball of the finger of the user is in contact with the center of the electrode 49, the LED and the PD of the pulse wave sensor 61 are in contact with the finger of the user and, thus, a signal for electrocardiogram measurement and a signal for the pulse wave measurement can be acquired from the finger (refer to FIG. 20B). That is, the electrode 49 and the pulse wave sensor 61 are positioned within a predetermined area. Here, an example of the predetermined area is the contact area of the finger of the user. At least the electrode 49 and the LED and the PD of the pulse wave sensor 61 are located within the above-mentioned predetermined area. The predetermined distance between the electrode 49 and the pulse wave sensor 61 is determined in accordance with the size of the electrode 49. Note that to measure the pulse wave by using the pulse wave sensor 61, it is desirable that a slight air gap be formed between the finger and each of the LED and the PD of the pulse wave sensor 61. To measure the pulse wave, it is desirable that the length D3 of the air gap be about 0.6 mm.

Let X be the diameter of the electrode 49. Let Y be the width of the pulse wave sensor 61 in a direction perpendicular to the direction in which the LED and the PD of the pulse wave sensor 61 are arranged, and let D be the distance between the electrode 49 and the pulse wave sensor 61. Then, the condition indicated by expression (1) may be satisfied. For example, if X=6 mm, Y=3 mm and D=1 mm, then a diameter F of 14 mm, which indicates the contact area of the finger of the user, satisfies expression (1). Accordingly, it can be determined that the electrode 49 and the pulse wave sensor 61 are positioned within the predetermined area.

Note that the dimensions of the electrode may be those obtained by reducing or enlarging the above-described dimensions on the basis of the actual contact area of the finger.

In addition, one end of an interconnect wire 59 is electrically connected to a portion (for example, a circular central portion in top view) of the back surface of the electrode 49 (the surface located inside the controller 1). The interconnect wire 59 is used to electrically connect the electrode 49 to an input terminal of a buffer 90.

Furthermore, a shield 65 is disposed around the electrode 49 so as to surround the electrode 49. FIG. 20A illustrates the arrangement positions of the electrode 49 and the shield 65. FIG. 20A(a) is a front view of the electrode 49, and FIG. 20A(b) is a perspective view of the electrode 49. Here, the shield 65 which surrounds the electrode 49 corresponds to the first shield member. Like the electrode 49, the shield 65 that surrounds the electrode 48 corresponds to the third shield member.

As illustrated in FIGS. 20A(a) and 20A(b), the electrode 49 and the shield 65 are disposed on a substrate. The electrode 49 is formed at a position to be in contact with the finger of the user when the finger is placed. The shield 65 is formed at a position so as to surround the outer circumference of the electrode 49. The shield 65 has an annular shape slightly larger than the electrode 49. The material of the shield 65 is a conductive substance (for example, copper). The shield 65 does not have to be a perfectly closed annular shape. Part of the annular shape may be cut out. In addition, the pattern of the interconnect wire 59 that connects the electrode 49 to the biopotential amplifying unit 14 may be formed in the above-described part.

The height of the shield 65 from a surface of the substrate may be smaller than the height of the electrode 49 from the surface of the substrate by at least the thickness of the electrode 49 (for example, about several 10 µm to several 100 µm). This is because the finger of the user is not brought into electrical contact with the shield 65. Note that the pulse wave sensor 61 needs to be in the vicinity of the finger, but does not have to be in contact with the finger. For example, the pulse wave sensor 61 may be separated from the finger by several 100 µm (more specifically, 600 µm). When the ball of the finger of the user is in contact with the electrode 49 and if the position slightly deviated from the position of the ball of the finger is in the vicinity of the pulse wave sensor 61, the above-described appropriate distance can be maintained.

As illustrated in FIG. 20A, let D1 be the distance between the electrode 49 and the shield 65, let W be the width of the pattern of the shield 65, and let D2 be the distance between the shield 65 and the pulse wave sensor 61. Then, the following expression (2) may be satisfied:

$$D = D1 + D2 + W \qquad (2)$$

When the electrode 49 and the pulse wave sensor 61 are disposed on a substrate, any interconnect wire pattern need not be provided on the surface having the electrode 49 and the pulse wave sensor 61 thereon in the range of the distance D1 between the electrode 49 and the shield 65. For example, if D1=0.2 mm, W=0.3 mm, and D2=0.5 mm, then, expression (2) is satisfied.

Here, as in the above example, the design may be such that D1 is twice the minimum value (0.1 mm) of the wiring interval on the substrate. In addition, the design may be such that W is three times the minimum value of the line width (0.1 mm) for the substrate in consideration of the case in which the driving capability of the shield 65 is maximized. D2 represents a minimum distance between the pulse wave sensor 61 and the interconnect wire. Normally, the distance D2 is set to 0.5 mm.

Note that, as illustrated in FIGS. 21A and 21B, the substrate having the electrode 49 and the shield 65 arranged thereon may be a multilayer substrate. A circular pattern of a shield 65a may be disposed on a layer below the layer having the electrode 49 disposed thereon so as to be concentric with the electrode 49. FIG. 21A is a front view of the layer having the shield 65a thereon, and FIG. 21B is an exploded perspective view of the layers. As illustrated in FIG. 21B, the layer having the electrode 49 and the shield 65 disposed thereon has the same structure as in FIG. 20A(a).

The shield 65a is connected to the shield 65 illustrated in FIG. 20A. Let Z be the diameter of the pattern of the shield 65a. Then, the following expression may be satisfied:

$$X + 2 \times D1 \leq Z \leq X + 2 \times (D1 + W) \qquad (3)$$

For example, if X=6 mm, D1=0.2 mm, and W=0.3 mm, then the shield 65a forms a circle with a diameter Z=7 mm. The shield 65a illustrated in FIGS. 21A and 21B is electrically connected through vias (not illustrated) provided on the pattern of the shield 65 illustrated in FIG. 20A.

Note that the shield 65a may be formed as an interconnect wire pattern (not illustrated) that does not include a path through which the interconnect wire 59 connects the electrode 49 to the biopotential amplifying unit 14.

Shield Disposed on Controller

Figure 22:
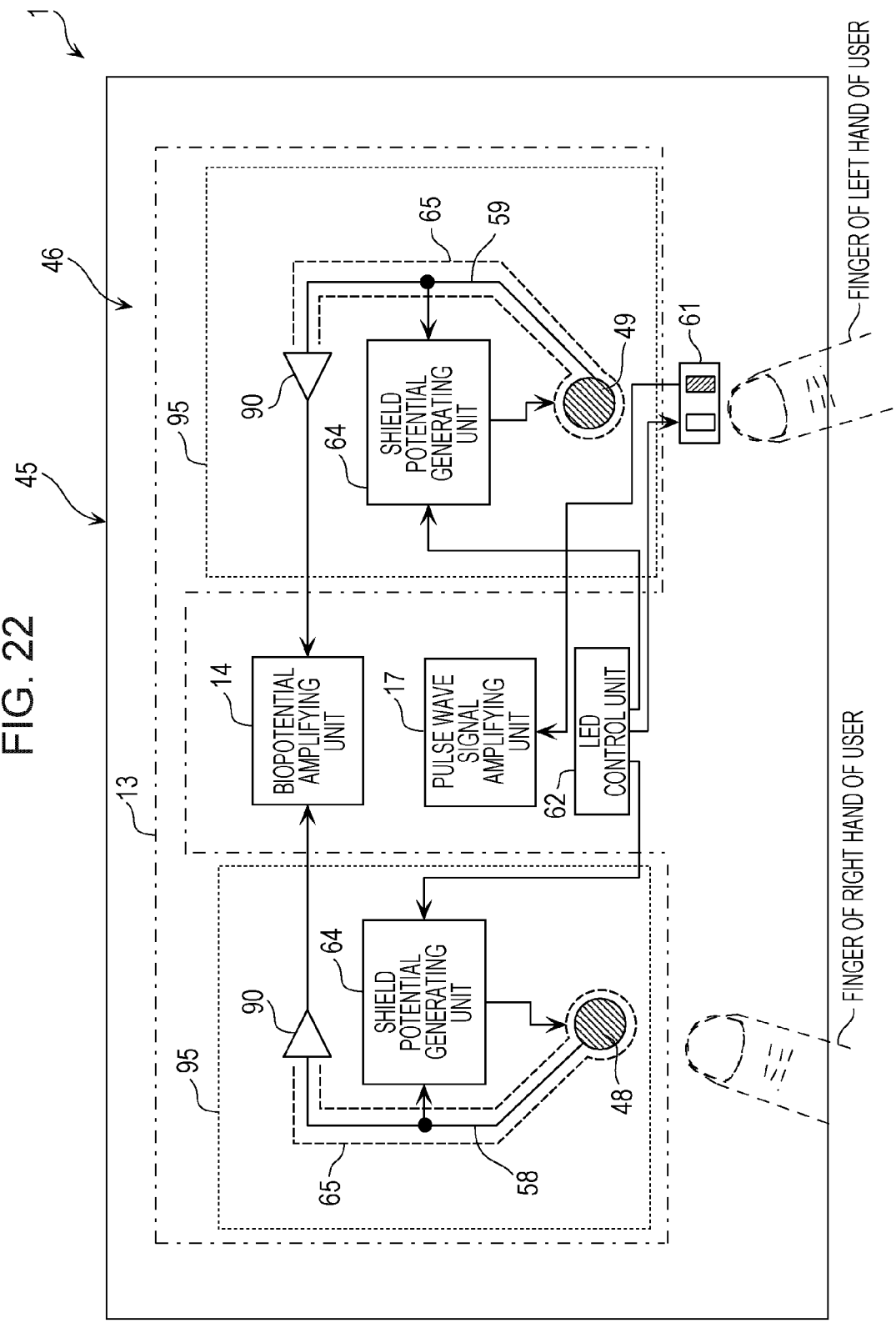
FIG. 22 illustrates the configuration of a shielded active electrode disposed on the back surface of the controller according to the first exemplary embodiment.

FIG. 22 illustrates an example of the electrodes disposed on the back surface 46 of the controller 1.

The electrode unit 13 is disposed on the casing of the controller 1. The electrode unit 13 has at least two electrodes 48 and 49, two interconnect wires 58 and 59, and two shields 65 disposed therein. Note that one of the electrodes 48 and 49 (e.g., the electrode 48) functions as a reference electrode, and the other electrode (e.g., the electrode 49) functions as a measuring electrode. Of the electrodes 48 and 49, the electrode 49 disposed at a position in the vicinity of the pulse wave sensor 61 corresponds to the first electrode, and the electrode 48 corresponds to the second electrode.

As illustrated in FIG. 22, when the user grips the controller with both hands, the electrode 48 is in contact with the finger of the left hand of the user, and the electrode 49 and the pulse wave sensor 61 are in contact with the finger of the right hand of the user. As can be seen from the example illustrated in FIG. 22, when the ball of the middle finger of the right hand and the ball of the middle finger of the left hand of the user are in contact with the electrodes 48 and 49, respectively, the fingers are in contact with all of the electrode units and the pulse wave sensor.

As illustrated in FIG. 22, the potentials detected by the electrodes 48 and 49 are buffered in the buffer 90 and are sent to the biopotential amplifying unit 14. Note that the buffer 90 connected to the electrode 49 by the interconnect wire 59 corresponds to a first amplifying unit, and the interconnect wire 59 corresponds to the first interconnect wire. In addition, the buffer 90 connected to the electrode 48 by the interconnect wire 58 corresponds to the second amplifying unit, and the interconnect wire 58 corresponds to the third interconnect wire.

The areas around the electrodes 48 and 49 and the interconnect wires 58 and 59 from the electrodes 48 and 49 to the input terminals of the buffer 90 are covered with a shield 65. The shield 65 is formed on the substrate as an interconnect wire pattern having a shape and a position so as to surround the outer circumference of the electrode 48 and the interconnect wire 58. Note that the shield 65 needs to have an interconnect wire pattern so that the electrical potential is the same throughout the pattern. In addition to the structure in which the shield 65 surrounds the entire outer circumference of the electrode 48 and the interconnect wire 58, even the structure in which the shield 65 does not surround part of the circumference (for example, 10%) can provide a certain level of the effect.

In addition, in the same manner as described above, the shield 65 is formed on the substrate as an interconnect wire pattern having a shape and a position so as to surround the outer circumference of the electrode 49 and the interconnect wire 59. Like the above-described structure, in addition to the structure in which the shield 65 surrounds the entire outer circumference of the electrode 49 and the interconnect wire 59, even the structure in which the shield 65 does not surround part of the circumference (for example, 10%) can provide a certain level of the effect.

The distance D1 between the shield 65 and each of the interconnect wire 58 between the electrode 48 and the input terminal of the buffer 90 and the interconnect wire 59 between the electrode 49 and the input terminal of the buffer 90 may be set to 0.2 mm. The potential of each of the shields 65 is supplied from a shield potential generating unit 64 which has received the control signal from an LED control unit 62.

A combination of any one of the electrodes 48 and 49 and the buffer 90 serves as a so-called active electrode 95. The active electrode 95 further includes the shield 65 and the shield potential generating unit 64.

Figure 23:
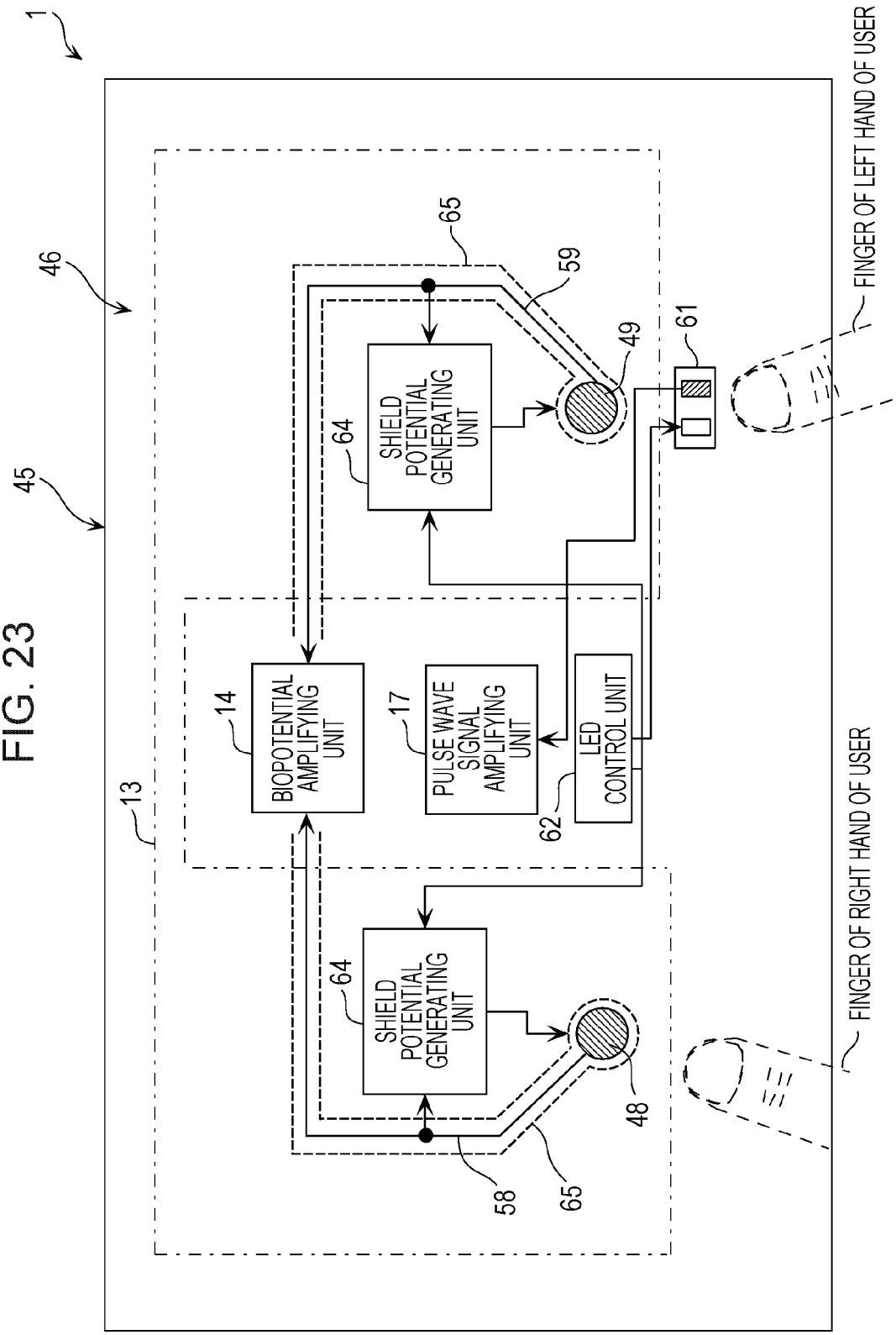
FIG. 23 is a configuration diagram illustrating another example of the arrangement of shields on the back surface of the controller according to the first exemplary embodiment.

Note that as illustrated in FIG. 23, if the buffer 90 is not provided in the path between the biopotential amplifying unit 14 and each of the electrodes 48 and 49, the path from the biopotential amplifying unit 14 to each of the electrodes 48 and 49 may be shielded by the shield 65.

Connection from Electrode Unit to Biopotential Amplifying Unit

Figure 24:
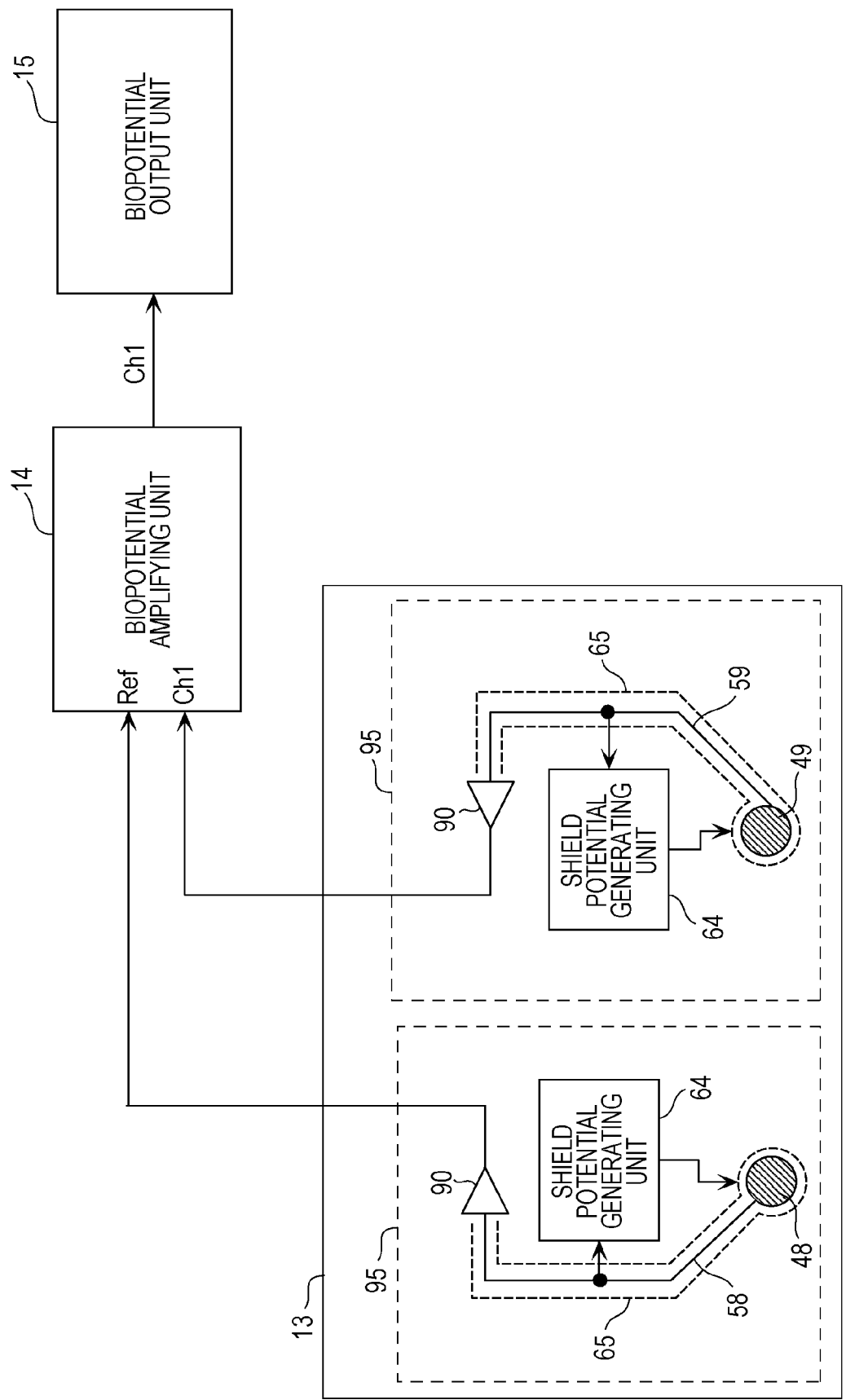
FIG. 24 illustrates connection between an electrode unit and a biopotential amplifying unit according to the first exemplary embodiment.

FIG. 24 illustrates connection from the electrode unit 13 of the controller 1 to the biopotential amplifying unit 14. The description below is given with reference to the electrode 49 serving as a measuring electrode (Ch1) and the electrode 48 serving as a reference electrode (Ref).

For each of the active electrodes 95 of the electrode unit 13, the electrodes 48 and 49 are connected to Ch1 and Ref of the biopotential amplifying unit 14 via the buffers 90, respectively. In the biopotential amplifying unit 14, the difference between the signal of Ch1 and the signal of Ref is calculated, and the resultant value is amplified (differential amplified). The amplified signal is subjected to filtering in a lowpass filter and is converted into a digital signal by an A/D converter. Thereafter, the digital signal is output to the biopotential output unit 15.

Figure 25:
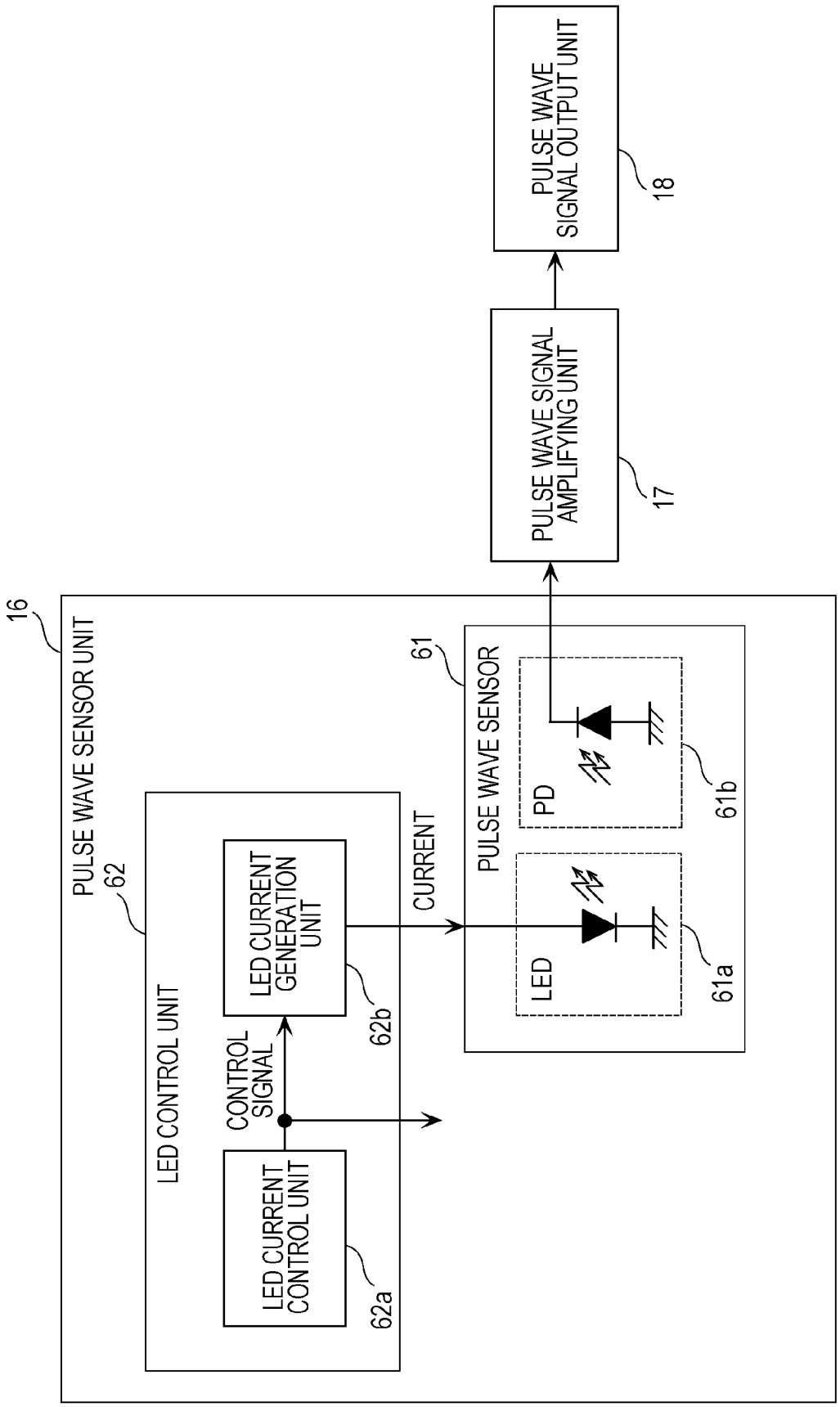
FIG. 25 illustrates the configuration of a pulse wave sensor unit and a pulse wave signal amplifying unit according to the first exemplary embodiment.

FIG. 25 illustrates a connection from the pulse wave sensor unit 16 of the controller 1 to the pulse wave signal amplifying unit 17. The pulse wave sensor unit 16 includes the LED control unit 62 and the pulse wave sensor 61. The LED control unit 62 includes an LED current control unit 62a and an LED current generation unit 62b. The LED current control unit 62a sends, to the LED current generation unit 62b, a control signal for controlling the amount of current flowing in the LED 61a. The LED current generation unit 62b supplies, to the LED 61a, the amount of current based on the control signal sent from the LED current control unit 62a.

Note that the predetermined current may be a constant current that does not vary with time or may be a current pulse, such as a pulse wave, which has a constant amplitude and which periodically turns on and off the current. The LED 61a emits light having a predetermined wavelength distribution characteristic on the basis of the current flowing between the anode and the cathode terminals of the LED 61a. The light is received by the middle finger of the right hand of the user, and the light reflected by the middle finger is converted into a current flowing between the cathode and anode terminals of the PD 61b. The cathode terminal of the PD 61b is connected to the pulse wave signal amplifying unit 17.

Figure 26:
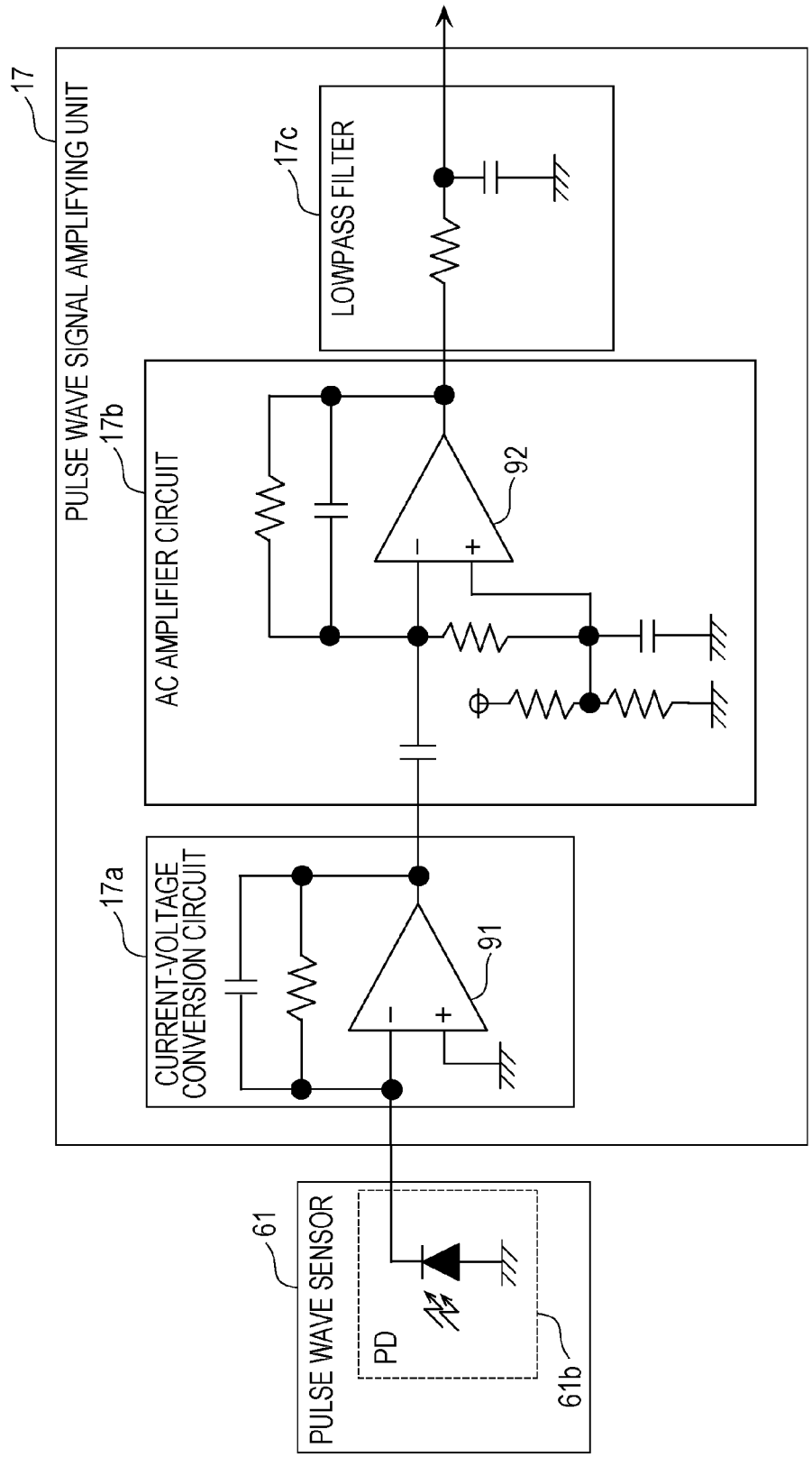
FIG. 26 is a circuit diagram of the pulse wave signal amplifying unit according to the first exemplary embodiment.

FIG. 26 is an example of a circuit diagram of the pulse wave signal amplifying unit 17. The pulse wave signal amplifying unit 17 includes a current-voltage conversion circuit 17a, an AC amplifier circuit 17b, and a lowpass filter 17c. The current-voltage conversion circuit 17a converts the current flowing through the cathode terminal of the PD 61b into a voltage signal in the pulse wave sensor unit 16. While removing a DC component, the AC amplifier circuit 17b amplifies, by using the amplifier 92, a voltage waveform output from the current-voltage conversion circuit 17a which uses an amplifier 91. The amplified pulse wave signal is subjected to filtering in the lowpass filter 17c. In the pulse wave signal amplifying unit 17 illustrated in FIG. 16, the pulse wave signal is further converted into a digital signal by an A/D converter, and the digital data of the pulse wave signal is output to the pulse wave signal output unit 18.

Shield Potential Generating Unit

Figure 27:
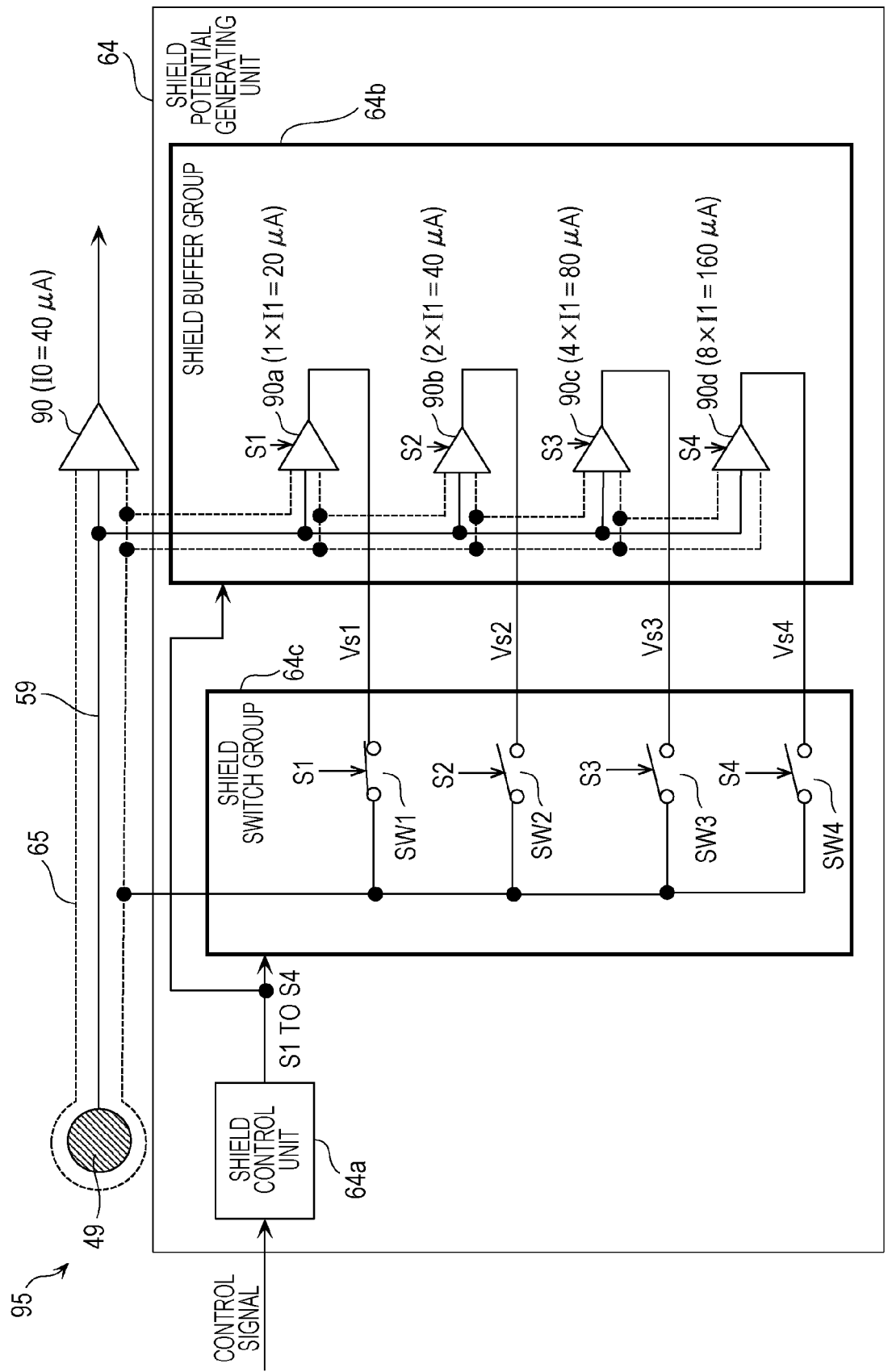
FIG. 27 is a circuit diagram of a shield potential generating unit according to the first exemplary embodiment.

FIG. 27 illustrates the shield potential generating unit 64 provided in the active electrode 95. A shield 65 is disposed around the electrode 49 and around the interconnect wire 59 connected between the electrode 49 and the input terminal of the buffer 90. In addition, the electrode unit 13 includes the shield potential generating unit 64. The shield potential generating unit 64 corresponds to the shield potential controller.

Note that the distance between the interconnect wire 59 between the electrode 49 and the input terminal of the buffer 90 and the shield 65 may be set to 0.2 mm.

The consumption current 10 of the buffer 90 is set to 40 µA. The shield potential generating unit 64 includes a shield control unit 64a, a shield buffer group 64b, and a shield switch group 64c. The shield control unit 64a receives a control signal from the above-mentioned LED control unit 62 (not illustrated) and sends shield control signals S1 to S4 to the shield buffer group 64b and the shield switch group 64c, as illustrated in FIG. 27.

FIG. 27 illustrates an example of the arrangement of buffers in the shield buffer group 64b. The shield buffer group 64b includes buffers 90a, 90b, 90c, and 90d having different driving capabilities. The potential detected by the electrode 49 is input to the buffers 90a, 90b, 90c and 90d at the same time. An interconnect wire connected to the buffers 90a, 90b, 90c and 90d is covered by the shield 65. The operation of each of the buffers 90a, 90b, 90c and 90d is controlled by the shield control unit 64a. More specifically, the operations of the buffers 90a, 90b, 90c and 90d are controlled by the shield control signals S1, S2, S3 and S4 output from the shield control unit 64a, respectively. Interconnect wires from the buffer output terminals Vs1, Vs2, Vs3, and Vs4 are connected to corresponding switches in the shield switch group 64c. Since the potential of each of the output terminals Vs1, Vs2, Vs3, and Vs4 is equal to the potential obtained by amplifying the potential of the interconnect wire by a factor of 1, the potential of each of the output terminals Vs1, Vs2, Vs3, and Vs4 is the same as the potential detected by the electrode 49. In contrast, the interconnect wires corresponding to the output terminals Vs1, Vs2, Vs3, and Vs4 support the driving capability (20 µA, 40 µA, 80 µA, and 160 µA) which correspond to the power consumption of the buffers 90a, 90b, 90c, and 90d, respectively.

Note that a circuit portion connected from the interconnect wire 59 to the shield 65 via the buffer 90a and the switch SW1 corresponds to a first buffer circuit, and a circuit portion connected from the interconnect wire 59 to the shield 65 via the buffer 90b and the switch SW2 corresponds to a second buffer circuit. In addition, the second buffer circuit may include one or both of a circuit portion connected from the interconnect wire 59 to the shield 65 via the buffer 90c and the switch SW3 and a circuit portion connected from the interconnect wire 59 to the shield 65 via the buffer 90d and the switch SW4. Under the control of the shield control unit 64a, the shield potential generating unit 64 applies the signal transmitted via the interconnect wire 59 to the shield 65 via the first buffer circuit and/or the second buffer circuit.

The circuit portions corresponding to the first buffer circuit and the second buffer circuit, which are disposed in the interconnect wire 58 that connects the electrode 48 to the buffer 90, are referred to as a third buffer circuit and a fourth buffer circuit, respectively. The shield potential generating unit 64 applies a signal transmitted via the interconnect wire 58 to the shield 65 via the third buffer circuit and/or the fourth buffer circuit.

The driving capabilities of the buffers 90a, 90b, 90c, and 90d may be in a ratio of 1:2:4:8, as illustrated in FIG. 27, or 1:1:1:1. Alternatively, any appropriate ratio may be used.

In addition, FIG. 27 illustrates an example of the arrangement of switches in the shield switch group 64c. The shield switch group 64c includes a plurality of switches SW1, SW2, SW3, and SW4. One terminal of each of the switches SW1, SW2, SW3, and SW4 is connected to a respective output terminal Vs1, Vs2, Vs3, and Vs4 of the buffers 90a, 90b, 90c, and 90d in the shield buffer group 64b. The other terminal of each of the switches SW1, SW2, SW3, and SW4 is connected to the interconnect wire from the shield 65. The switches SW1, SW2, SW3, and SW4 are controlled by the shield control signals S1, S2, S3, and S4 sent from the shield control unit 64a, respectively. The sizes of the switches SW1, SW2, SW3, and SW4 may be in a ratio of 1:1:1:1. Alternatively, a ratio that is the same as the ratio of the driving capabilities of the buffers 90a, 90b, 90c and 90d in the shield buffer group 64b (i.e., 1:2:4:8) may be used.

Figure 28:
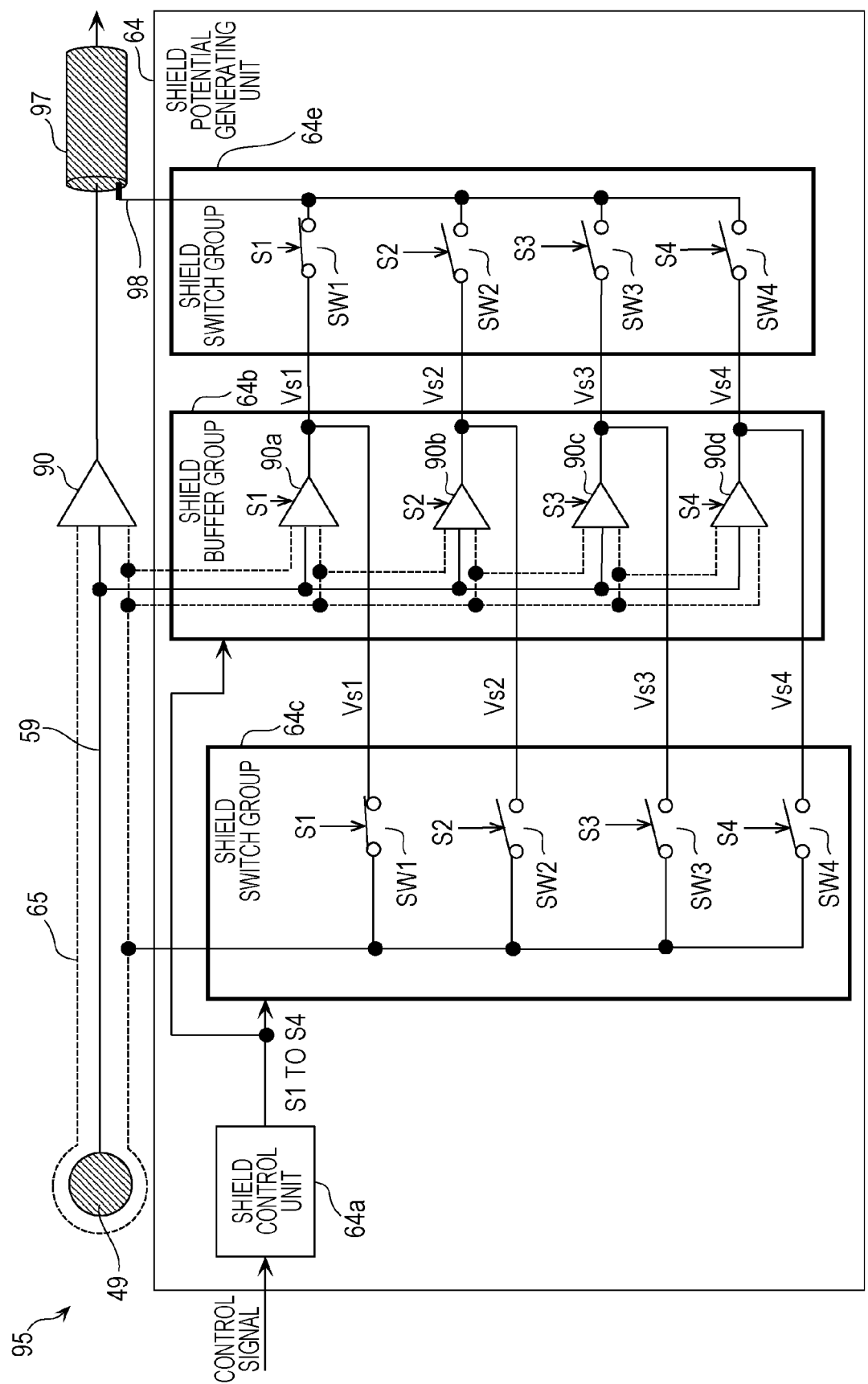
FIG. 28 is a circuit diagram of a shield potential generating unit according to a first modification of the first exemplary embodiment.

The shield potential generating unit 64 may supply a shielding potential to a shielded wire (corresponding to the third shield member) of a coaxial cable in addition to the shield used around the electrodes. More specifically, as illustrated in FIG. 28, the electrode unit 13 further includes a shield switch group 64e, and the buffers 90a, 90b, 90c, and 90d in the shield buffer group 64b are connected to the shield switch group 64e. The buffers 90a, 90b, 90c, and 90d are connected to a respective terminal of the switches SW1, SW2, SW3, and SW4 of the shield switch group 64e. The other terminals of the switches SW1, SW2, SW3, and SW4 are connected together and to a shielded line 98 of a coaxial cable 97. The core of the coaxial cable 97 is connected to the output terminal of the buffer 90 and is further connected to the biopotential amplifying unit 14 (not illustrated). In this manner, to strictly protect the output of the buffer 90 from external noise when the pulse wave is measured, a shield potential having an appropriate current driving capability is advantageously supplied to the coaxial cable. Note that in this case, the biopotential amplifying unit 14 corresponds to the signal receiving unit, and the shield switch group 64e corresponds to the switching unit.

Figure 29:
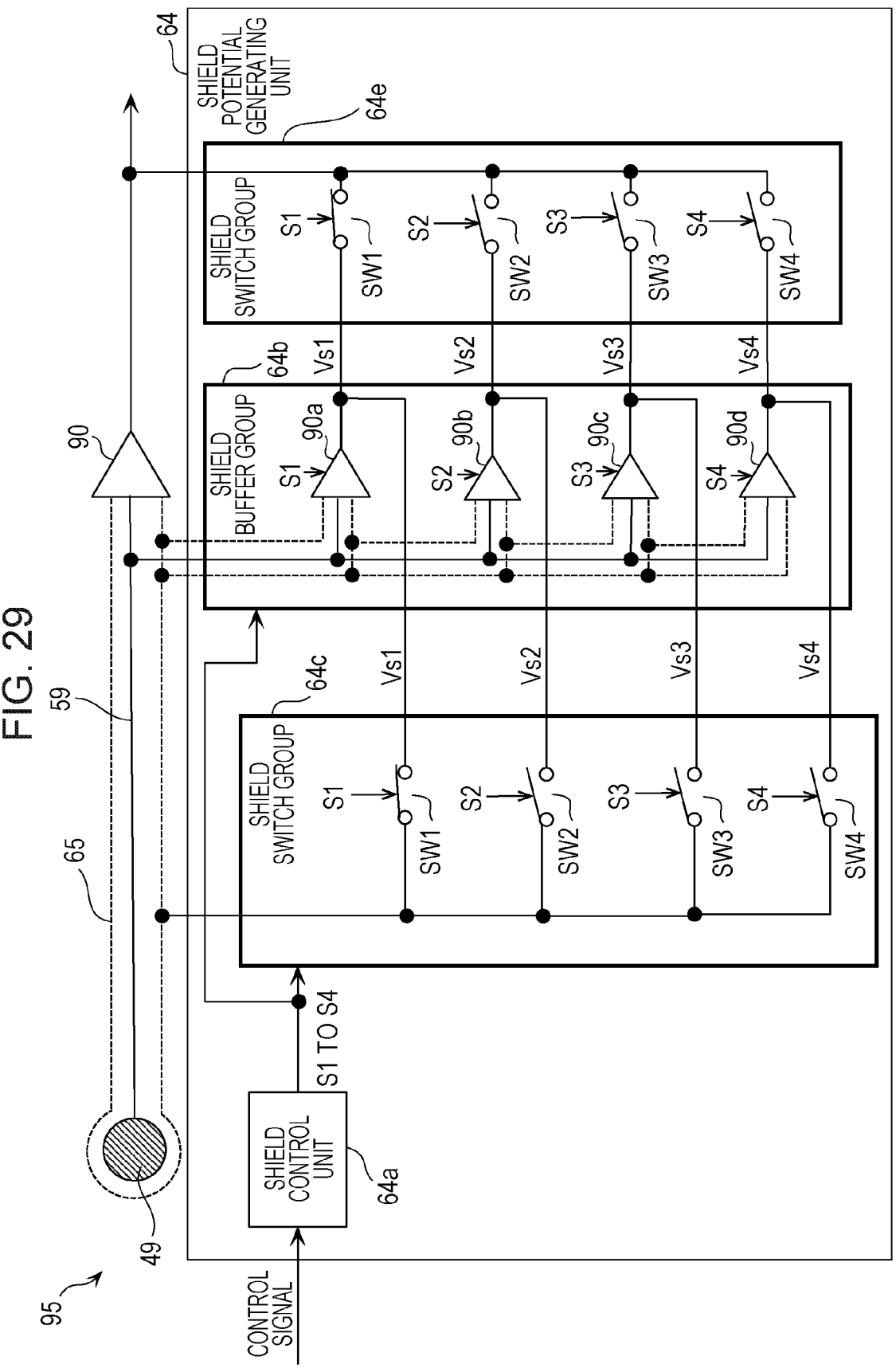
FIG. 29 is a circuit diagram of a shield potential generating unit according to a second modification of the first exemplary embodiment.

Note that by using not only the shield used around the electrodes but also the driving capability of each of the buffers 90a, 90b, 90c, and 90d of the shield buffer group 64b, the shield potential generating unit 64 can increase the driving capability of the buffering operation performed by the buffer 90. For example, as illustrated in FIG. 29, when the interconnect wire that connects the output terminal of the buffer 90 to the biopotential amplifying unit 14 (not illustrated) is relatively long, the current driving capability of the interconnect wire needs to be increased. In this case, the driving capability can be increased by the amount corresponding to the buffers selected by using the shield control signals S1 to S4 in the shield buffer group 64b of the shield potential generating unit 64.

Figure 30:
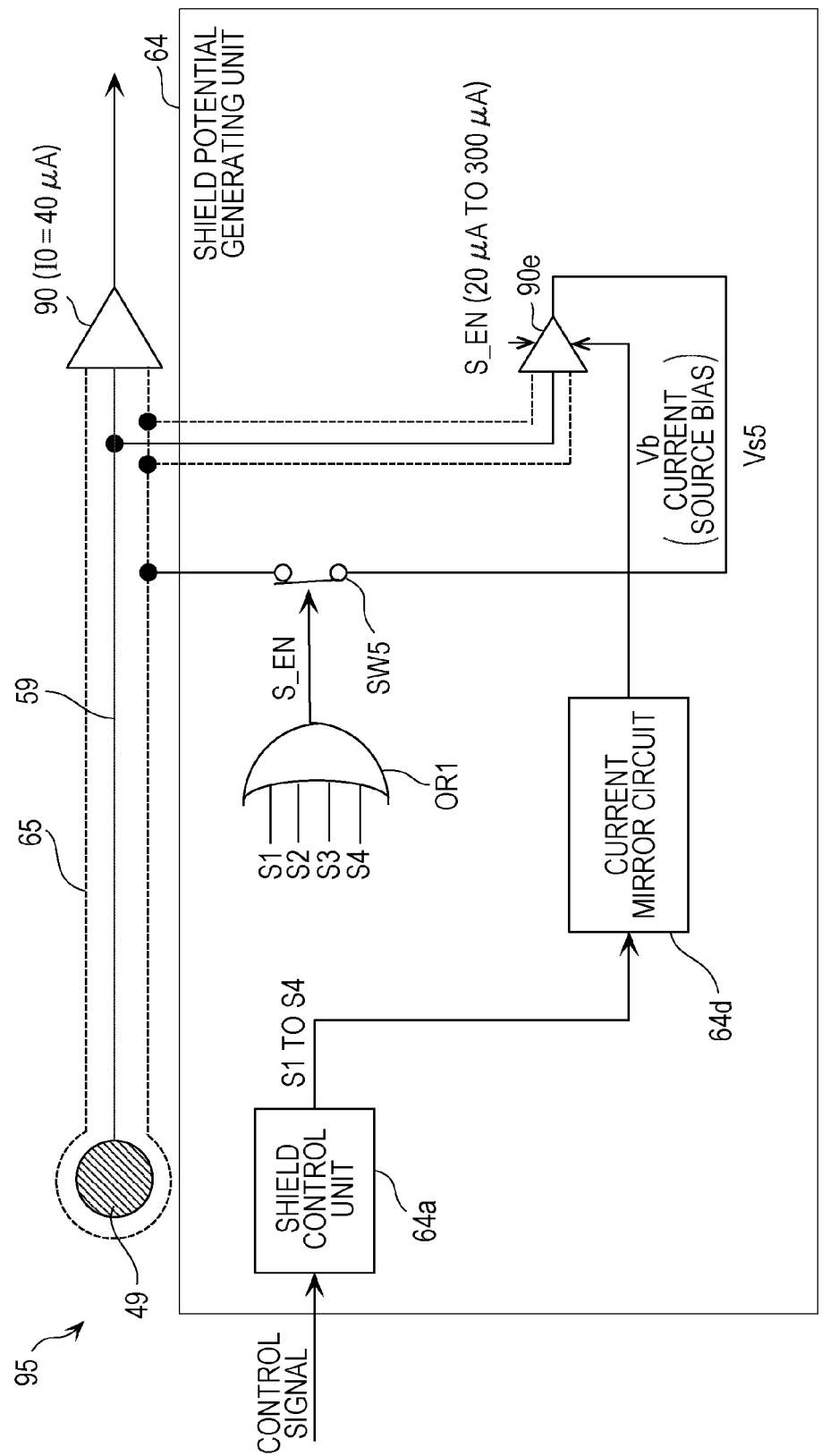
FIG. 30 is a circuit diagram of a shield potential generating unit according to a third modification of the first exemplary embodiment.

In addition, note that instead of using the shield buffer group 64b and the shield switch group 64c, the shield potential generating unit 64 can be configured by using a buffer 90e having variable driving capability, a switch SW5, a current mirror circuit 64d, and an OR gate OR1 (refer to FIG. 30). The mirror ratio of the current source generated by the current mirror circuit 64d is changed on the basis of the shield control signals S1 to S4, and a bias voltage Vb for a tail current source provided inside the buffer 90e is supplied. In the example illustrated in FIG. 30, the current driving capability of the buffer 90e can be changed from 20 μA to 300 μA in accordance with the combination of the shield control signals S1 to S4. The four shield control signals S1 to S4 are input to the OR gate, and a signal S_EN which is a logical sum (OR) of S1 to S4 is supplied from the OR gate as a control signal of the switch SW5. In addition, the signal S_EN is input to the buffer 90e to control the operation performed by the buffer 90e. An output signal Vs5 of the buffer 90e is supplied via the switch SW5 in the form of a shield potential.

Control Flow of Shield Control Unit

Figure 32:
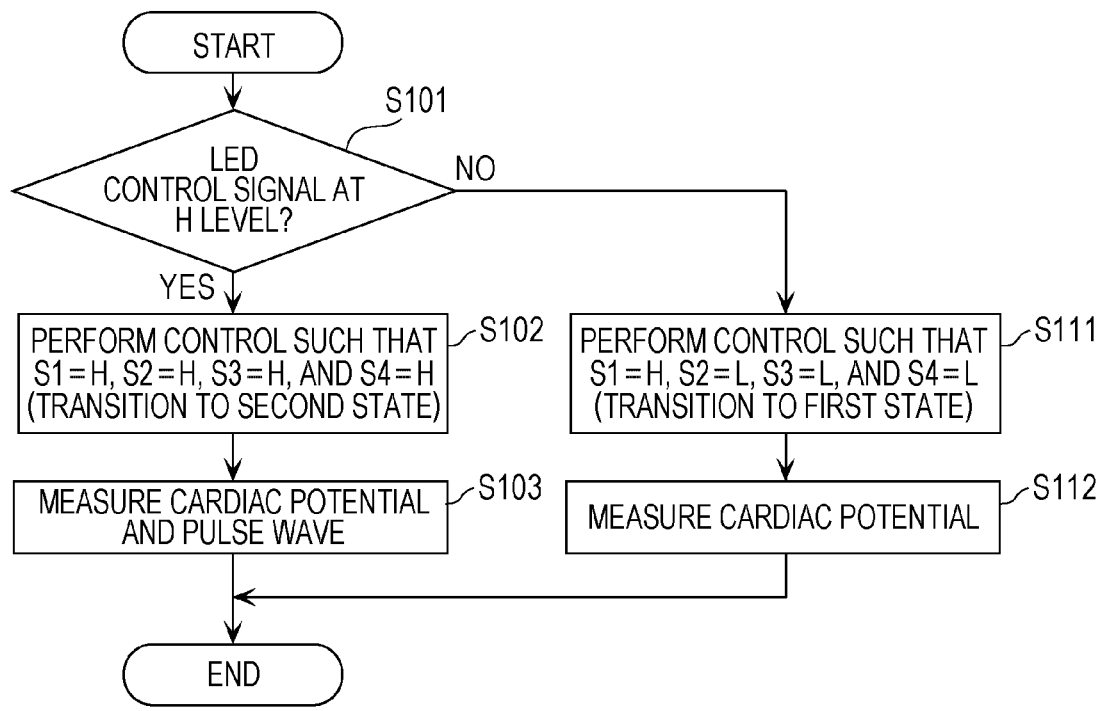
FIG. 32 is a flowchart illustrating a control method for use of the shield control unit according to the first exemplary embodiment.

FIG. 31 illustrates the variation of the measurement state. The first state is a measurement state in which the cardiac potential is measured, and the second state is a measurement state in which both the cardiac potential and the pulse wave are measured (simultaneous measurement). The processing performed in the first state and the second state illustrated in FIG. 31 is described below with reference to the flowchart illustrated in FIG. 32. Steps S101 to S103 and steps S111 and S112 in FIG. 32 are performed by the shield control unit 64a disposed in the controller 1. Note that hereinafter, the term "H" and "H level" refer to high level (high potential), and the terms "L" and "L level" refer to low level (low potential).

Step S101
The shield control unit 64a determines whether the LED control signal is at the H level. If the LED control signal is at the H level (YES in step S101), the processing proceeds to step S102. Otherwise (NO in step S101), the processing proceeds to step S111.

Step S102
The shield control unit 64a outputs the shield control signals S1 to S4. The logic level of the control signal S1 is H. The logic level of the control signal S2 is H. The logic level of the control signal S3 is H. The logic level of the control signal S4 is H. This combination of the logic levels indicates that the measurement state is to be switched to the second state in which the cardiac potential and the pulse wave are measured.

Step S103
The controller 1 and the information processing apparatus 2 measure the pulse wave signal by using the pulse wave sensor 61 while measuring the cardiac potential by using the electrode 49.

Step S111
The shield control unit 64a outputs the shield control signals S1 to S4. The logical level of the control signal S1 is H. The logical level of the control signal S2 is L. The logical level of the control signal S3 is L. The logical level of the control signal S4 is L. This combination of the logic levels indicates that the measurement state is to be switched to the first state in which the cardiac potential is measured.

Step S112
The controller 1 and the information processing apparatus 2 measure the cardiac potential by using the electrode 49.

Through the series of processes described above, the shield control unit 64a applies the signal transmitted via the first interconnect wire to the first shield member via the second buffer circuit at a predetermined time point at which the pulse wave is measured by the pulse wave sensor 61. The predetermined time point is a time point at which the LED control unit 62 instructs the LED to emit light.

As described above, the information processing system 100 measures the pulse wave and the cardiac potential while switching between the first state and the second state. In this manner, deterioration of the signal quality of the cardiac potential in the simultaneous measurement of the pulse wave and the cardiac potential can be prevented.

Example of Control of Shield Driving Capability

An example of control of the shield driving capability by using the shield control unit 64a is described with reference to FIGS. 31 and 33. A time t represents an elapsed time from a start time t0 of the simultaneous measurement of the cardiac potential and the pulse wave. The first state and the second state are separately described under the assumption that the first state occurs before the time t0 and the second state occurs after the time t0.

Figure 33:
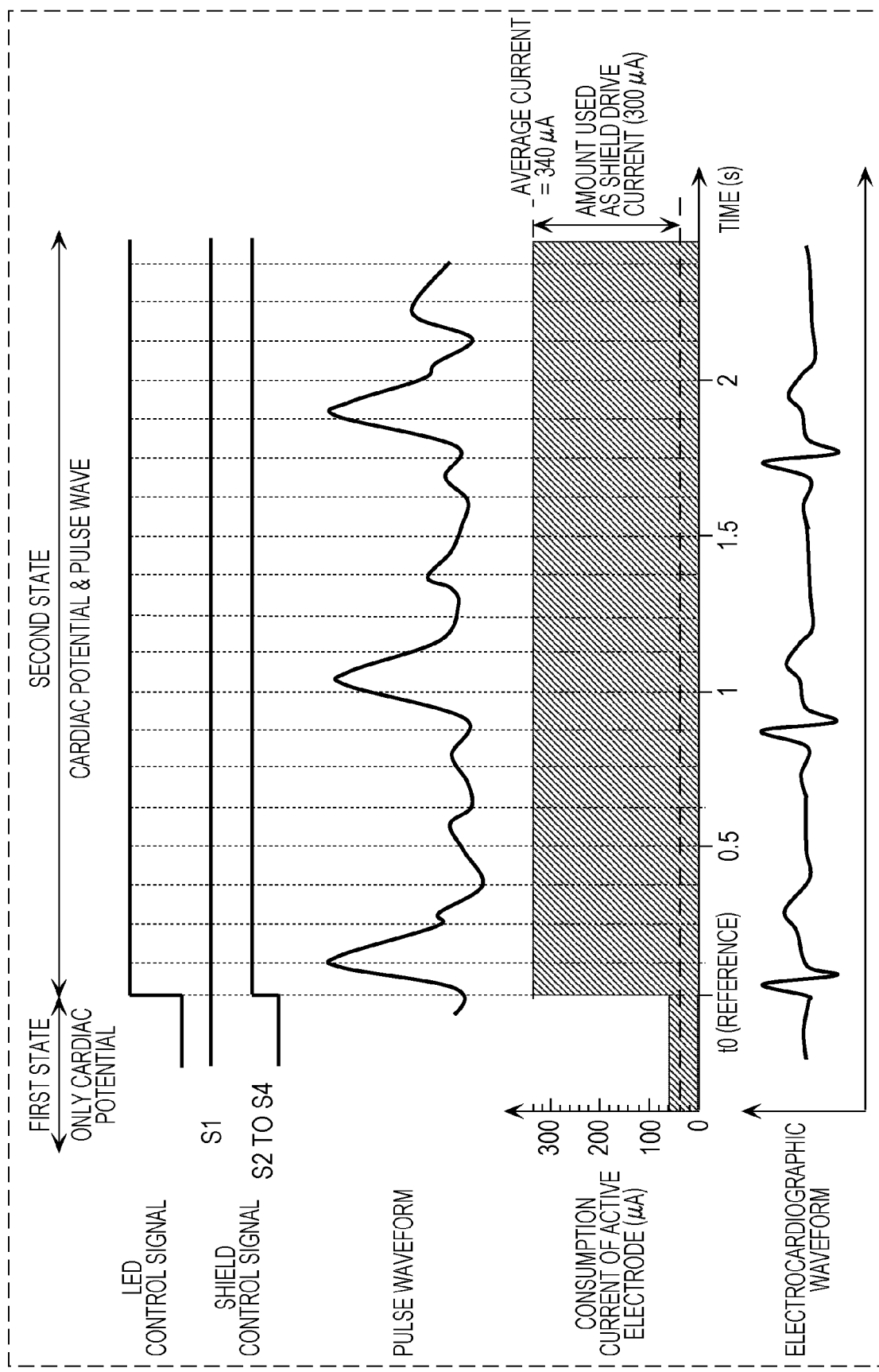
FIG. 33 illustrates an example of a time-series change in the shield driving capability according to the first exemplary embodiment.

The first state represents a state in which the cardiac potential is measured at a time before the time t0 in FIG. 33. At this time, as illustrated in FIG. 31, the level of the control signal received from the LED control unit 62 is L (off). The level of the shield control signal S1 output from the shield control unit 64a is H. The level of the shield control signal S2 is L. The level of the shield control signal S3 is L. The level of the shield control signal S4 is L. As a result, control is performed so that the operation performed by the buffer 90a of the shield buffer group 64b is turned on, the operation performed by the buffer 90b is turned off, the operation performed by the buffer 90c is turned off, and the operation performed by the buffer 90d is turned off. In addition, the switch SW1 in the shield switch group 64c is closed, the switch SW2 is open, the switch SW3 is open, and the switch SW4 is open.

Accordingly, the potential Vs1 having the driving capability of I1=20 µA is supplied as the potential of the shield 65. The current consumed by one active electrode 95 is 60 µA, which is equal to the sum of I0 and I1. To measure the cardiac potential, the driving capability of the shield 65, that is, the current consumption of the active electrode 95 need not be higher than is necessary. Note that the electrode 48 (not illustrated) used as the reference electrode is not disposed at a position in the vicinity of the pulse wave sensor 61. Accordingly, even in the second state (simultaneous measurement of electrocardiogram and pulse wave) described below, it is not necessary to change the consumption current of the active electrode 95 from 60 µA.

The second state is a state in which the cardiac potential and the pulse wave are measured at the same time, and the second state starts at the time t0 in FIG. 33. At this time, the drive current of the shield 65 of the electrode 49 used as the measuring electrode for Ch1 is changed. As illustrated in FIG. 31, the control signal received from the LED control unit 62 is H (on), and the levels of the shield control signals S1 to S4 output from the shield control unit 64a are all H. Thus, control is performed so that the operations performed by the buffers 90a to 90d of the shield potential generating unit 64 are all turned on, and the switches SW1, SW2, SW3, and SW4 in the shield switch group 64c are all closed. Consequently, the potential Vs1 having the driving capability of 15×I1=300 µA, which is the sum of the driving capabilities of the buffers 90a to 90d, is supplied as the potential of the shield 65. By increasing the driving capability of the interconnect wire of the shield 65 to 300 µA, the electrocardiographic waveform and the pulse waveform illustrated in FIG. 33 can be obtained at the same time. At this time, the consumption current per active electrode 95 is 340 µA. This consumption current is about ⅓ of the value obtained in existing active electrodes. That is, the cardiac potential and the pulse wave having high signal quality can be simultaneously measured with low power consumption.

Biopotential Processing Unit

Figure 34:
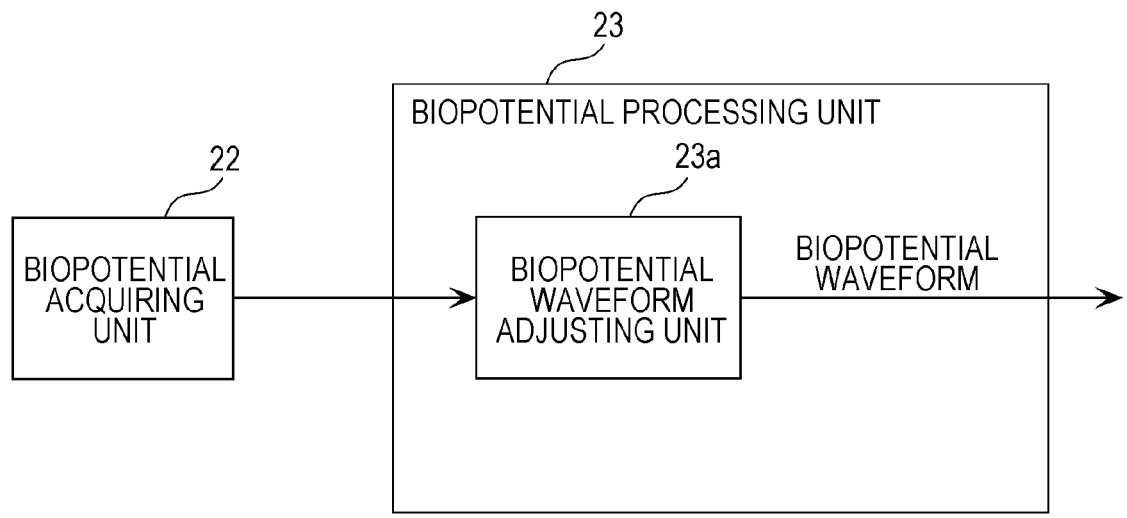
FIG. 34 is a block diagram illustrating the configuration of a biopotential processing unit according to the first exemplary embodiment.

FIG. 34 illustrates the configuration of the biopotential processing unit 23. The biopotential processing unit 23 illustrated in FIG. 34 includes a biopotential waveform adjusting unit 23a. An example of the controller 1 includes at least the biopotential acquiring unit 22 and the biopotential waveform adjusting unit 23a.

The biopotential acquiring unit 22 acquires the information about biopotential between the electrode 48 and the electrode 49.

The cardiac potential data of Ch1 acquired by the biopotential acquiring unit 22 is sent to the biopotential waveform adjusting unit 23a. The biopotential waveform adjusting unit 23a includes a highpass filter having a changeable cutoff frequency and a lowpass filter. The biopotential waveform adjusting unit 23a may include a notch filter that blocks the frequency (50 Hz or 60 Hz) of the commercial power supply. The biopotential waveform adjusting unit 23a performs signal processing using these filters and the like to generate a biopotential waveform. The generated biopotential waveform is displayed on the display device 3 via the display information output unit 27.

Pulse Wave Signal Processing Unit

Figure 35:
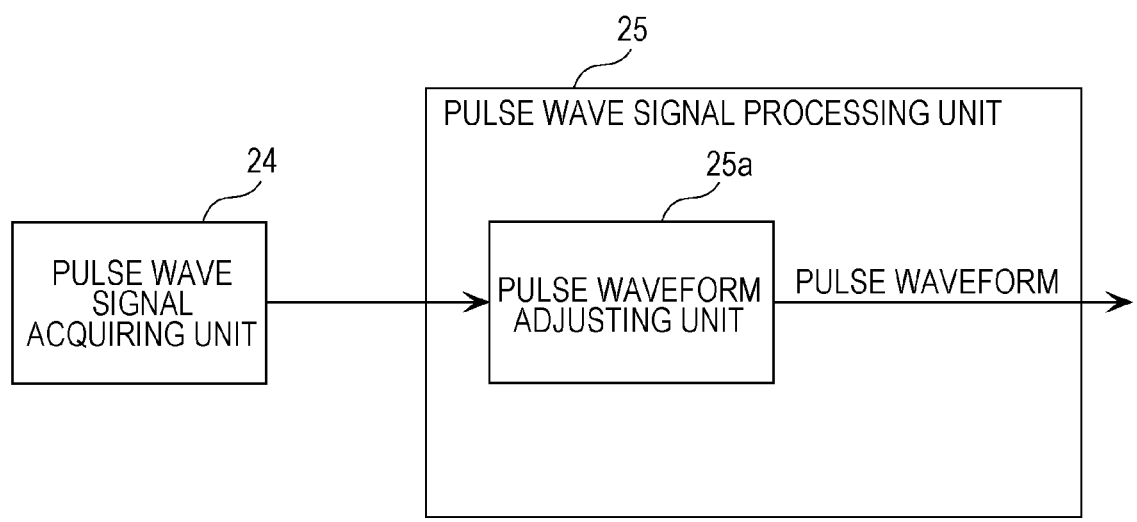
FIG. 35 is a block diagram illustrating the configuration of a pulse wave signal processing unit according to the first exemplary embodiment.

FIG. 35 illustrates the configuration of the pulse wave signal processing unit 25. The pulse wave signal processing unit 25 illustrated in FIG. 35 includes a pulse waveform adjusting unit 25a. An example of the controller 1 includes at least the pulse wave signal acquiring unit 24 and the pulse waveform adjusting unit 25a.

The pulse wave signal acquiring unit 24 acquires the information about the pulse wave signal detected by the pulse wave sensor unit 16.

The data of the pulse wave signal acquired by the pulse wave signal acquiring unit 24 is sent to the pulse waveform adjusting unit 25a. The pulse waveform adjusting unit 25a includes a highpass filter having a changeable cutoff frequency and a lowpass filter. The pulse waveform adjusting unit 25a may include a notch filter that blocks the frequency (50 Hz or 60 Hz) of the commercial power supply. The pulse waveform adjusting unit 25a performs signal processing using these filters and the like to generate a pulse waveform. The generated pulse waveform is sent to the display device 3 via the display information output unit 27 and is displayed by the display device 3.

Application Processing Unit

Figure 36:
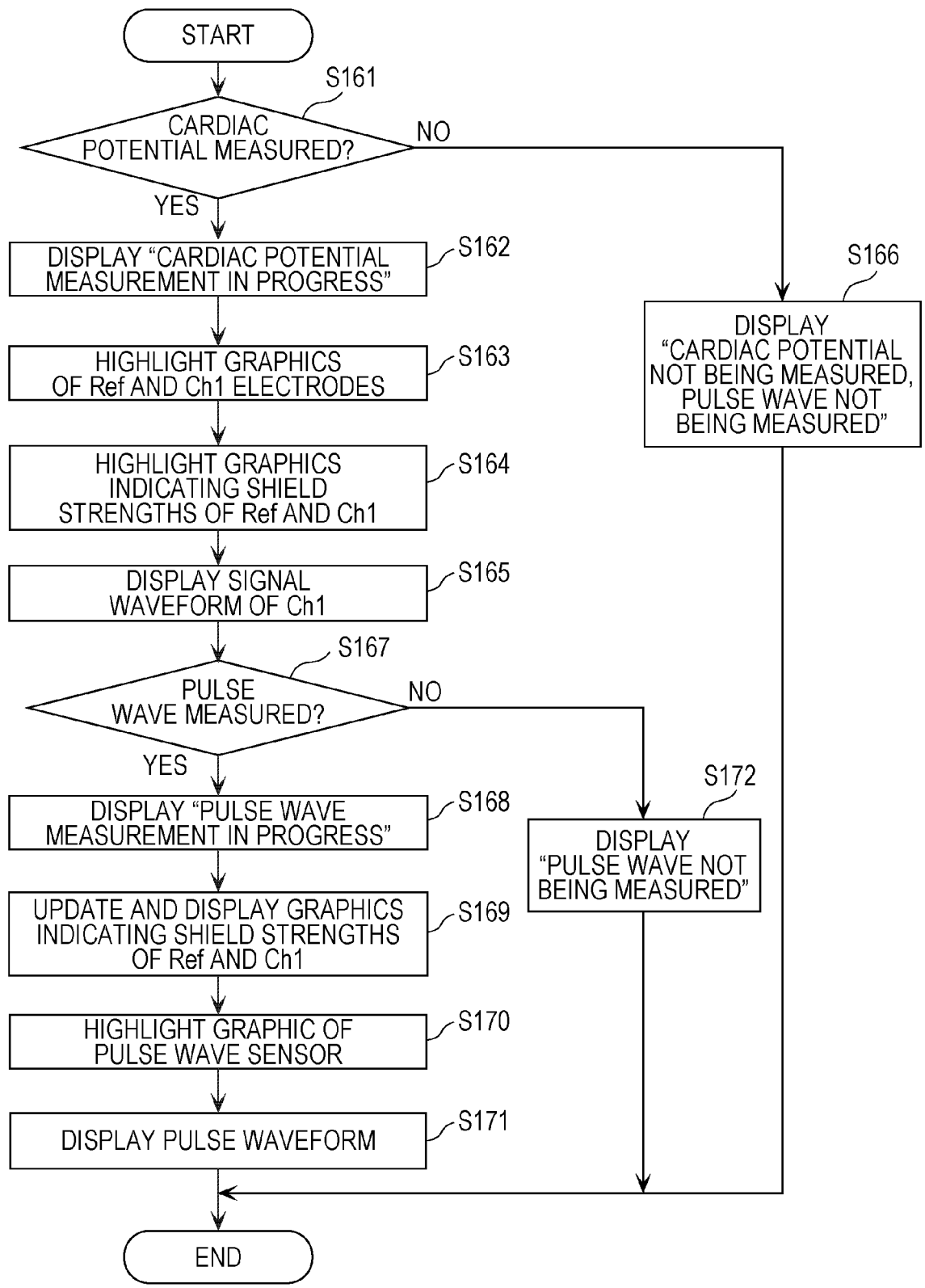
FIG. 36 is a flowchart of application processing performed by an application processing unit according to the first exemplary embodiment.
Figure 37:
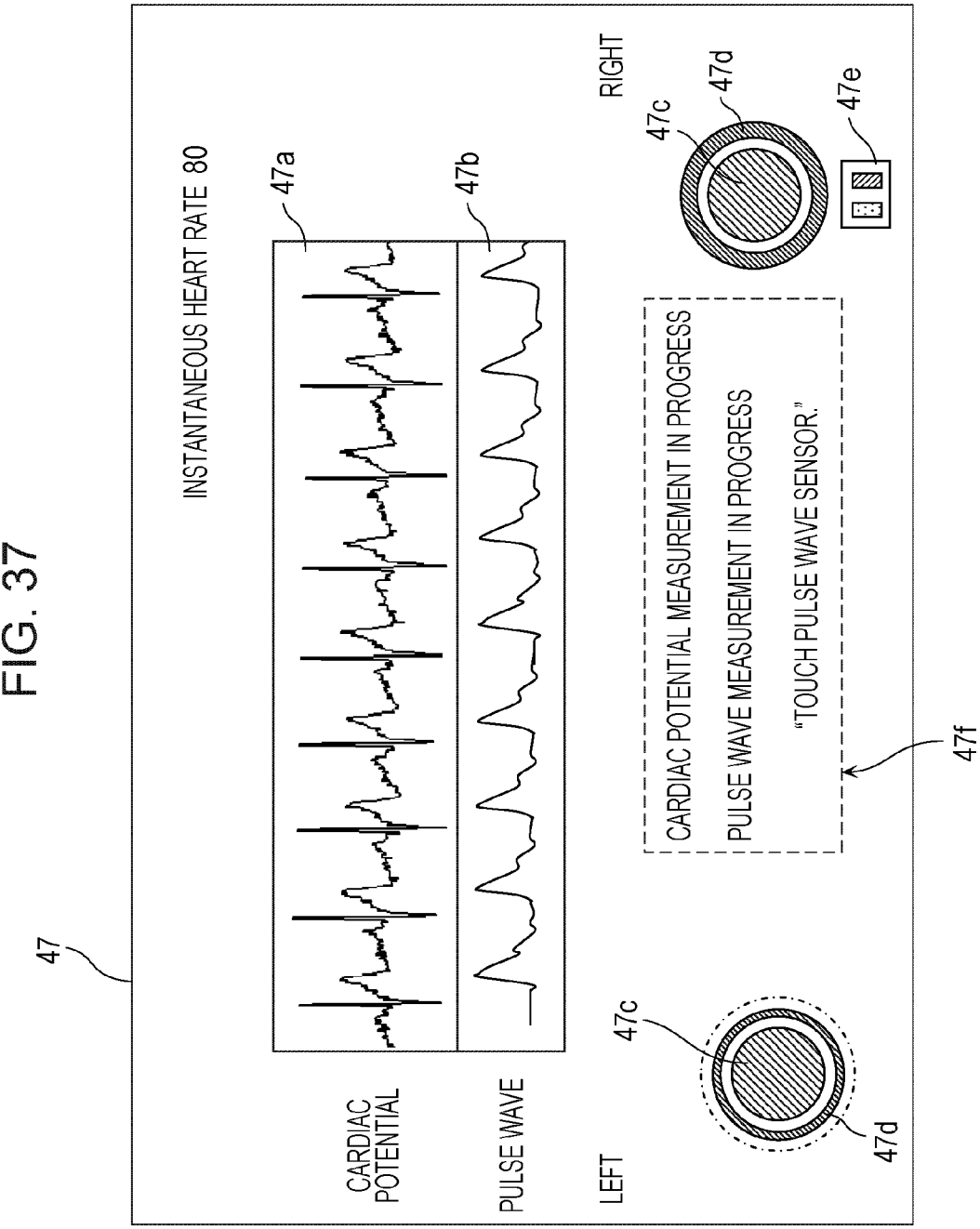
FIG. 37 illustrates an image displayed by a display unit according to the first exemplary embodiment.

FIG. 36 illustrates a process flow of the application processing unit 26 that processes biometric information. A flowchart illustrated in FIG. 36 is described with reference to the displayed image illustrated in FIG. 37. FIG. 37 illustrates the arrangement of the electrodes provided on the back surface of the controller 1 as viewed transparently from the front surface. In addition, the image illustrated in FIG. 37 may be displayed on the display device 3 (refer to, for example, FIG. 1) or the display unit 47 (refer to FIG. 2(b)) of the controller 1. In this example, FIG. 37 illustrates the image displayed on the display unit 47.

In FIG. 37, the electrocardiographic waveform and the pulse waveform currently being measured are displayed in an electrocardiographic waveform graphic display section 47a and the pulse waveform graphic display section 47b of the display unit 47, respectively. In addition, when the cardiac potential is being measured, a corresponding electrode graphic display section 47c is colored and displayed in the screen. However, when the cardiac potential is not measured, the corresponding electrode graphic display section 47c is displayed in white. Furthermore, when a pulse wave signal is being measured, a corresponding pulse wave sensor graphic display section 47e is displayed in colors corresponding to the LED and PD. However, when the pulse wave signal is not measured, the corresponding pulse wave sensor graphic display section 47e is displayed as a white box without displaying both LED and PD.

Step S161

The application processing unit 26 determines whether the cardiac potential is being measured on the basis of the output result of the biopotential processing unit 23. If the cardiac potential is being measured (YES in step S161), the processing proceeds to step S162. However, if the cardiac potential is not measured (NO in step S161), the processing proceeds to step S166.

Step S162

Since the cardiac potential is being measured, the display information output unit 27 causes the display unit 47 to display the message "cardiac potential measurement in progress".

Step S163

The display information output unit 27 causes the display unit 47 to highlight the graphics of the electrodes corresponding to Ref (reference electrode) and Ch1 (measurement electrode). As a result, the highlighting is applied to the graphics of the electrodes displayed in the electrode graphic display section 47c in FIG. 37.

Step S164

The display information output unit 27 causes the display unit 47 to highlight the graphics corresponding to the respective shields of Ref (reference electrode) and Ch1 (measurement electrode). As a result, the highlighting is applied to the graphics of the shields displayed in a shield graphic display section 47d in FIG. 37.

Step S165

The display information output unit 27 displays the electrocardiographic waveform measured by Ch1 (the measurement electrode) in the electrocardiographic waveform graphic display section 47a in FIG. 37.

Step S166

Since the cardiac potential and the pulse wave are not being measured, the display information output unit 27 causes the display unit 47 to display a message "Cardiac potential not being measured, pulse wave not being measured", and the processing is completed. The message is displayed in a measurement state display section 47f of the display unit 47.

Step S167

The application processing unit 26 determines whether the pulse wave is being measured on the basis of the output result of the pulse wave signal processing unit 25. If the pulse wave is being measured (YES in step S167), the processing proceeds to step S168. However, if the pulse wave is not being measured (NO in step S167), the processing proceeds to step S172.

Step S168

Since the pulse wave signal is being measured, the display information output unit 27 causes the display unit 47 to display the message "Pulse wave measurement in progress" in the measurement state display section 47f. Step S169

The display information output unit 27 updates the graphics corresponding to the strengths of the shield of Ref (reference electrode) and Ch1 (measurement electrode) and causes the display unit 47 to highlight the graphics. The graphics are highlighted in the shield graphic display section 47d of FIG. 37. In general, unlike the measurement of the cardiac potential, the strength of the shield is increased to the maximum of the driving capability of the shield. Accordingly, display is performed such that the line width of the shield graphic display section 47d on the right is maximized.

Step S170

The display information output unit 27 causes the display unit 47 to highlight the graphic corresponding to the pulse wave sensor. The highlighting is applied to the graphic of the pulse wave sensor in the pulse wave sensor graphic display section 47e in FIG. 37.

Step S171

The display information output unit 27 displays the pulse wave signal waveform measured by the pulse wave sensor in the pulse waveform graphic display section 47b in FIG. 37, and the processing is completed.

Step S172

Since the pulse wave is not being measured, the display information output unit 27 causes the display unit 47 to display the message "Pulse wave not being measured", and the processing is completed. The message is displayed in the measurement state display section 47f.

Modifications of Display Section

Figure 38:
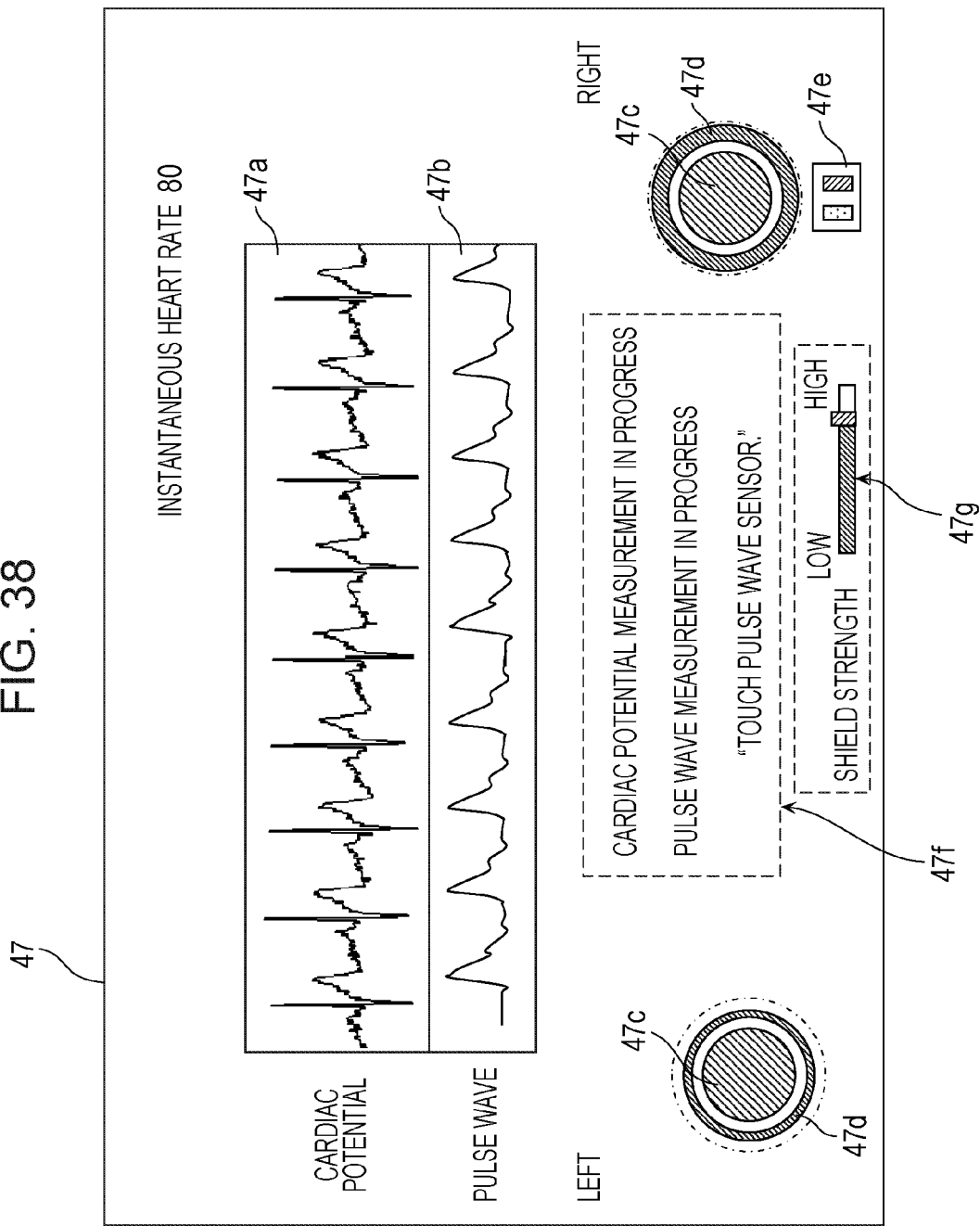
FIG. 38 illustrates an example of the modified image displayed by the display unit according to the first exemplary embodiment.

As illustrated in the display unit 47 of FIG. 38, the user may adjust the strength (the driving capability) of the shield controlled by the shield control unit 64a by operating a shield driving capability setting section 47g. The shield control signals S1 to S4 corresponding to the shield driving capability set in the shield driving capability setting section 47g of the display unit 47 illustrated in FIG. 38 are updated from the values illustrated in FIG. 31. Thereafter, the potential of the shield 65 having the shield driving capability corresponding to the updated setup value is supplied by the shield control unit 64a.

Note that the shield driving capability setting section 47g corresponds to the reception unit that receives an instruction indicating which of the first buffer circuit and the second buffer circuit is to be used by the shield potential generating unit 64 to apply a signal to the first shield member.

Effects

As described above, the driving capability of the shield disposed around the electrode provided on the controller 1 can be changed on the basis of the control signal sent from the LED control unit 62. Accordingly, when the biopotential and the pulse wave are measured at the same time, low-power-consumption and high signal quality simultaneous measurement of the biopotential and the pulse wave can be provided.

Second Exemplary Embodiment

The overall basic configuration of an information processing system according to the present exemplary embodiment is the same as the configuration illustrated in FIGS. 15 and 16. Accordingly, the processing of the biopotential processing unit 23, the processing of the pulse wave signal processing unit 25, and the control of the shield control unit 64a, which have the configurations that differ from those of the first exemplary embodiment, are described below.

Biopotential Processing Unit

Figure 39:
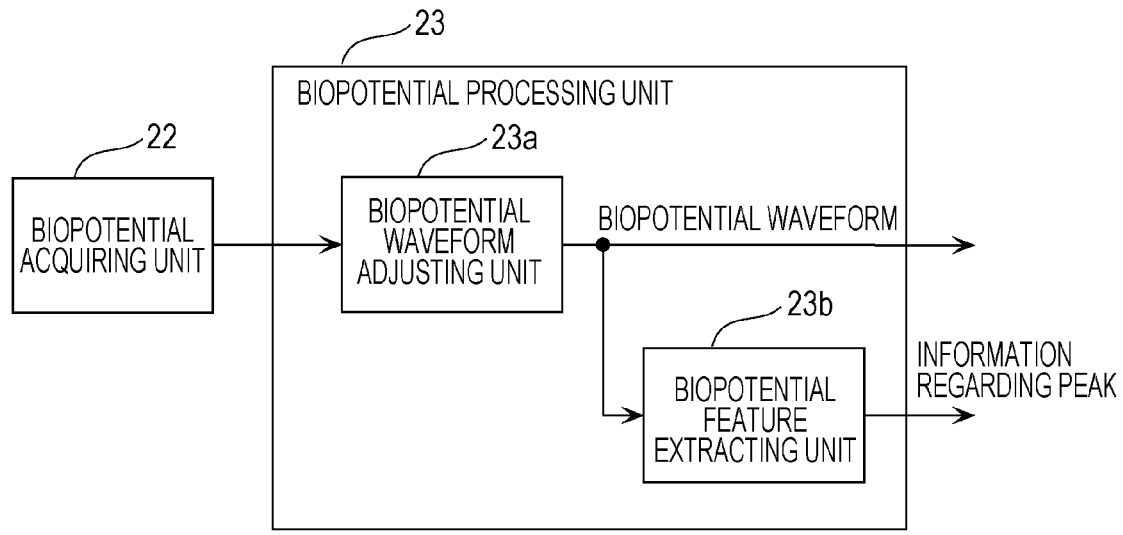
FIG. 39 is a block diagram illustrating the configuration of a biopotential processing unit according to a second exemplary embodiment.

FIG. 39 illustrates the configuration of the biopotential processing unit 23. The biopotential processing unit 23 illustrated in FIG. 39 includes a biopotential feature extracting unit 23b in addition to the biopotential waveform adjusting unit 23a. The controller 1 includes at least the biopotential acquiring unit 22, the biopotential waveform adjusting unit 23a, and the biopotential feature extracting unit 23b.

The biopotential feature extracting unit 23b extracts the feature of the biopotential on the basis of the biopotential waveform shaped by the biopotential waveform adjusting unit 23a. For example, components such as P wave, Q wave, R wave, S wave, T wave, and U wave are extracted from the electrocardiographic waveform shaped by biopotential waveform adjusting unit 23a, and the interval of temporally adjacent R waves (the RR interval) is calculated. In this manner, the information regarding the period of the electrocardiographic waveform is extracted.

Note that the information extracted by the biopotential feature extracting unit 23b may be displayed on the display device 3 via the display information output unit 27.

Pulse Wave Signal Processing Unit

Figure 40:
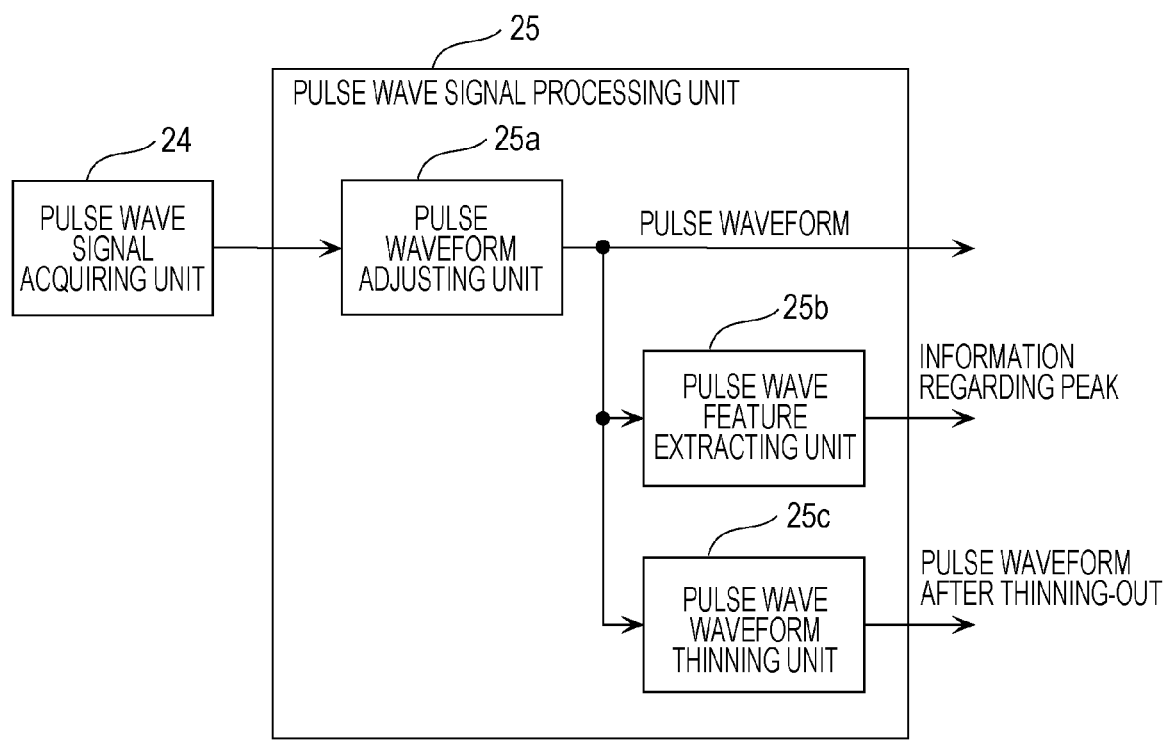
FIG. 40 is a block diagram illustrating the configuration of a pulse wave signal processing unit according to the second exemplary embodiment.

FIG. 40 illustrates the configuration of the pulse wave signal processing unit 25. The pulse wave signal processing unit 25 illustrated in FIG. 40 includes a pulse wave feature extracting unit 25b and a pulse waveform thinning unit 25c in addition to the pulse waveform adjusting unit 25a. An example of the controller 1 includes at least the pulse wave signal acquiring unit 24, the pulse waveform adjusting unit 25a, the pulse wave feature extracting unit 25b, and the pulse waveform thinning unit 25c.

The pulse wave feature extracting unit 25b extracts the feature of the pulse wave on the basis of the pulse waveform shaped by the pulse waveform adjusting unit 25a. For example, the pulse waveform adjusting unit 25a calculates a velocity pulse waveform, which is the first derivative of the pulse wave with respect to time, and an acceleration pulse waveform, which is the second derivative of the pulse wave with respect to time. The information about the peak of the pulse waveform is extracted on the basis of the velocity pulse waveform. The information about each of the peaks and/or the inflection point of the pulse waveform is extracted on the basis of the acceleration pulse waveform.

Note that the information extracted by the pulse wave feature extracting unit 25*b* may be sent to the display device 3 via the display information output unit 27 and may be displayed by the display device 3.

The pulse waveform thinning unit 25*c* outputs the pulse waveform subjected to a thinning-out process based on a predetermined thinning-out interval. For example, when the sampling frequency of the pulse waveform is 1024 Hz and the number of thinning-out points is 64, the thinning-out interval is $\frac{1}{16}$ (0.0625) of a second.

Control Flow of Shield Control Unit

FIG. 41 illustrates a measurement state and a variation of the shield control signal. The values of the shield control signals S1 to S4 are determined on the basis of the waveform information of the pulse wave. Since the first state is a state in which the biopotential is measured and the pulse wave is not measured, the values of the shield control signal S1 is set to H, and the values of the shield control signal S2 to S4 are all set to L. The second state is a state in which the cardiac potential and the pulse wave are simultaneously measured. One of the variations illustrated in FIG. 41 is selected as the values of the shield control signals S1 to S4 on the basis of the amplitude and the period of the pulse wave.

Figure 42:
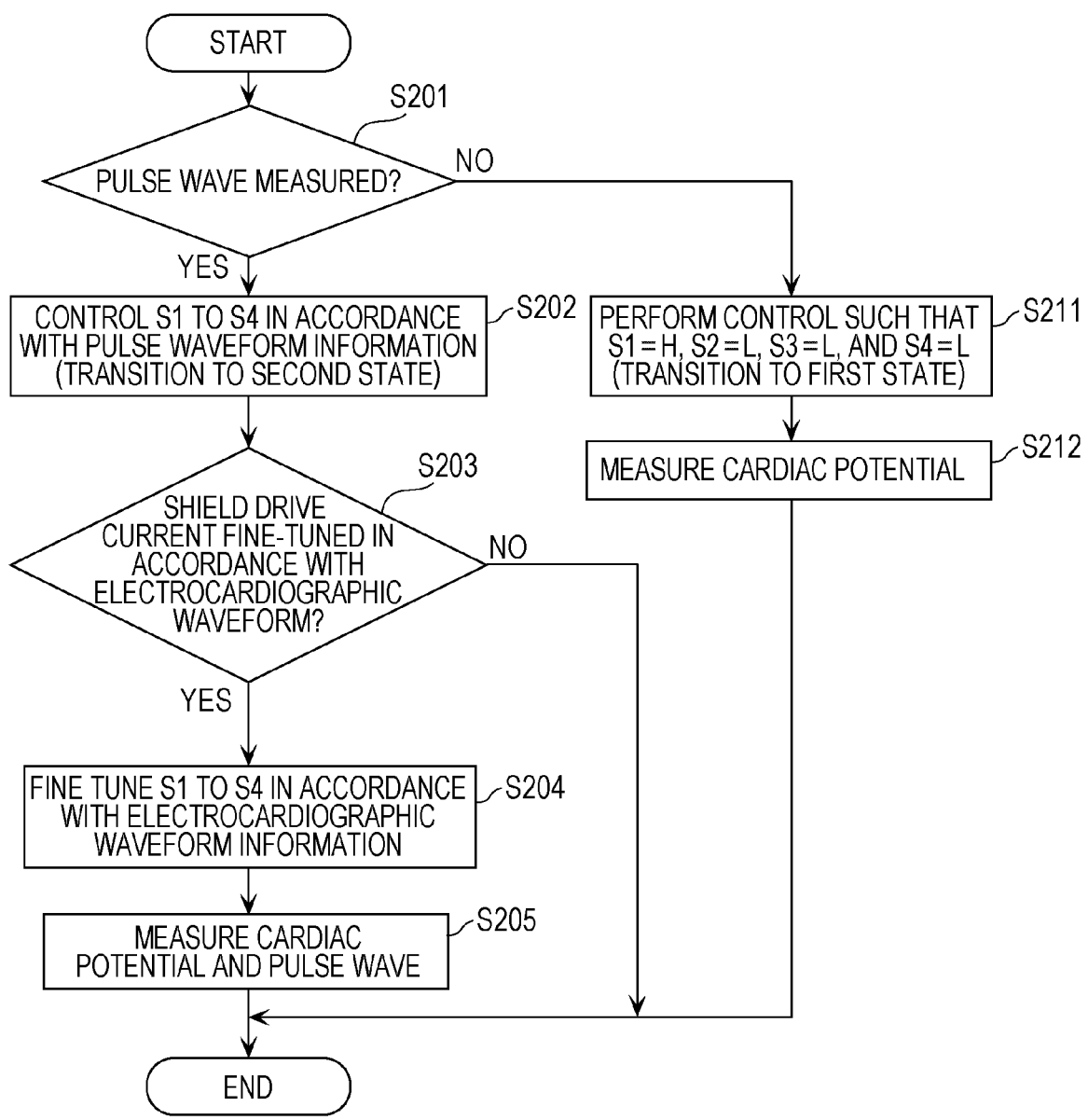
FIG. 42 is a flowchart of a control method for use of the shield control unit according to the second exemplary embodiment.

The processing for the first state and the second state illustrated in FIG. 41 is described with reference to the flowchart illustrated in FIG. 42. Note that the processing in steps S231 to S237 in FIG. 42 is performed by the shield control unit 64*a* disposed in the controller 1.

Step S201

The shield control unit 64*a* determines whether the pulse wave is measured on the basis of the pulse waveform information. If it is determined that the pulse wave is measured (YES in step S201), the processing proceeds to step S202. Otherwise (NO in step S201), the processing proceeds to step S211. Note that it is determined that pulse wave is measured if, for example, a new pulse wave peak predicted on the basis of the pulse wave detected by the pulse wave sensor 61 should be detected.

Step S202

The shield control unit 64*a* outputs the shield control signals S1 to S4. One of the combinations illustrated in FIG. 41 is selected for the shield control signals S1 to S4 on the basis of the waveform information of the pulse wave. This operation corresponds to changing the measurement state to the second state in which the cardiac potential and the pulse wave are measured.

Step S203

The shield control unit 64*a* determines whether the drive current of the shield is finely adjusted in accordance with the electrocardiographic waveform. If it is determined that the drive current of the shield is finely adjusted (YES in step S203), the processing proceeds to step S204. Otherwise (NO in step S203), the processing is completed.

Step S204

The shield control unit 64*a* performs fine adjustment by using the combination of the values of the shield control signals S1 to S4 selected in step S202 on the basis of the information about the electrocardiographic waveform. Step S205

The controller 1 and the information processing apparatus 2 measure the pulse wave signal by using the pulse wave sensor 61 while measuring the cardiac potential by using the electrode 49.

Step S211

The shield control unit 64*a* outputs the shield control signals S1 to S4. The logical levels of the shield control signals S1 to S4 are H, L, L, and L, respectively. This operation corresponds to changing the measurement state to the first state in which the cardiac potential is measured. Step S212

The controller 1 and the information processing apparatus 2 measure the cardiac potential by using the electrode 49.

Through the series of processes described above, the shield control unit 64*a* applies, to the first shield member, the signal sent via the second buffer circuit and the first interconnect wire at a predetermined time point when the pulse wave is measured by the pulse wave sensor 61. The predetermined time point is a time point when a new pulse wave peak, which is predicted on the basis of the pulse wave detected by the pulse wave sensor 61, should be detected.

As described above, the controller 1 and the information processing apparatus 2 measure the pulse wave and the cardiac potential while switching between the first state and the second state. In this manner, deterioration of the quality of the cardiac potential signal in the simultaneous measurement of the pulse wave and the cardiac potential can be prevented.

Example of Control Performed by Shield Control Unit

An example of control of the shield driving capability performed by the shield control unit 64*a* is described below with reference to FIG. 43. A time t represents an elapsed time from a start time t0 of the simultaneous measurement of the cardiac potential and the pulse wave. The first state and the second state are separately described under the assumption that the first state occurs before the time t0 and the second state occurs after the time t0.

The first state represents a state in which the cardiac potential is measured before t0 illustrated in FIG. 43. At this time, as illustrated in FIG. 28, the cardiac potential is measured, and there is no information about the pulse waveform. Accordingly, the level of the shield control signal S1 output from the shield control unit 64*a* is H, and the levels of the shield control signals S2 to S4 are all L. Control is performed so that the operation of the buffer 90*a* in the shield buffer group 64*b* is turned on, the operations of the buffers 90*b* to 90*d* are turned off, the switch SW1 in the shield switch group 64*c* is closed, and the switches SW2 to SW4 are all open. Therefore, the potential Vs1 having the driving capability of I1=20 µA is supplied as the potential of the shield 65. The consumption current per active electrode 95 is 60 µA. Note that the electrode 48 (not illustrated) used as the reference electrode is not disposed in the vicinity of the pulse wave sensor 61. Accordingly, even in the second state (simultaneous measurement of the electrocardiogram and pulse wave) described below, the consumption current of the active electrode 95 need not be changed from 60 µA.

The second state is a state in which simultaneous measurement of the cardiac potential and pulse wave is performed from the time t0 illustrated in FIG. 43. At this time, the drive current of the shield 65 of the electrode 49 used as a measuring electrode for Ch1 is changed on the basis of the pulse wave information.

For example, in the case of the pulse waveform illustrated in FIG. 43, since the time t0 is relatively close to the peak time of the pulse wave amplitude, control is performed so that the level of the shield control signal S1 output from the shield control unit 64a is L, the levels of the shield control signals S2 and S3 are H, and the level of the shield control signal S4 is L. As a result, control is performed so that the operation of the buffer 90a in the shield buffer group 64b is turned off, the operations of the buffers 90b and 90c are turned on, the operation of the buffer 90d is turned off, the switch SW1 in the shield switch group 64c is open, the switches SW2 and SW3 are closed, and the switch SW4 is open. Therefore, the potential Vs1 having the driving capability of 6×I1=120 µA, which is the sum of the driving capacities of the buffers 90a to 90c, is supplied to the interconnect wire as the potential of the shield 65. By increasing the driving capability of the interconnect wire of the shield 65 to 120 µA, the electrocardiographic waveform and the pulse waveform can be acquired at the same time, as illustrated in FIG. 43. At this time, the consumption current per active electrode 95 is 160 µA.

When the time is 1/16 of a second, the level of the shield control signal S1 output from the shield control unit 64a is H. The level of the shield control signal S2 is L, the level of the shield control signal S3 is H, and the level of the shield control signal S4 is H. Accordingly, the shielding driving capability is controlled to 260 µA. At this time, the consumption current per active electrode 95 is 300 µA. In the same manner as described above, the shield control unit 64a controls the driving capability of the shield on the basis of the pulse waveform.

After the pulse wave signal passes the peak point, the electrocardiographic waveform continues to have an amplitude sufficiently smaller than the pulse wave signal. Note that by slightly increasing the driving capability of the shield around a time point when the T wave and U wave, which are typical waveforms of the electrocardiographic waveform, appear, a slight change in the electrocardiographic waveform can be reliably detected. For example, when, like the T wave of the electrocardiographic waveform at a time of 5/16 second (0.3125 second), a waveform having an amplitude smaller than the R wave appears, the shield control unit 64a may further fine tune the driving capability of the shield control unit 64a on the basis of the biopotential waveform. To accurately detect the T wave of the electrocardiographic waveform although the amplitude of the pulse wave is close to the reference (GND), the driving capability of the shield at this time is increased to 120 µA.

As described above, the average value of the consumption current of the active electrode is 120 µA per electrode, which is one-eighth of the consumption power required for existing active electrodes.

Note that the number of the thinning points of the pulse waveform for controlling the shielding ability by the shield control unit 64a is not limited to 64. The configuration may allow the user to change the number of the thinning points by using the display unit illustrated in FIG. 37.

As described above, according to the information processing system 100 of the above-described exemplary embodiment, by providing a shield capable of changing the driving capability around the electrode disposed on the upper side surface of the controller, the biopotential and the pulse wave having high signal quality can be simultaneously measured with low power consumption without being influenced by a variation of the potential caused by the pulse wave signal.

In addition, in the electronic device, the first electrode and the first interconnect wire are shielded by the shield member driven by the second buffer circuit having a relatively large drive current when the pulse wave is measured. Thus, noise coupled into the cardiac potential acquired by the electrode due to the pulse wave signal can be blocked. This is because since the amplitude of the pulse wave signal is larger than the amplitude of the cardiac potential and, in addition, the cardiac potential and the pulse wave signal differ from each other in phase, the first electrode and the first interconnect wire can be shielded by using the output line of a buffer having a relatively large drive current (for example, 1 mA). In this way, according to the electronic device, deterioration of the quality of the cardiac potential signal in simultaneous measurement of the pulse wave and the cardiac potential can be prevented. Furthermore, the electronic device can acquire a signal for electrocardiogram measurement and a signal for pulse wave measurement from one of the fingers of a person. In this manner, deterioration of the quality of the cardiac potential signal can be prevented in simultaneous measurement of the pulse wave and the cardiac potential. In addition, by reducing the number of measurement points, the usability of the electronic device can be increased.

In addition, in the electronic device, the first electrode and the first interconnect wire are shielded by a shield member driven by a second buffer circuit having a relatively large drive current at a time when the light emitting unit emits light. When the pulse wave sensor measures the pulse wave, the light emitting unit emits light. In this manner, the electronic device can easily obtain the measurement time of the pulse wave by using the time of light emission by the light emitting unit and can prevent deterioration of the quality of the cardiac potential signal in simultaneous measurement of the pulse wave and the cardiac potential.

In addition, at a time when a new pulse wave peak should be detected, the first electrode and the first interconnect wire are shielded by a shield member driven by a second buffer circuit having a relatively large drive current. The pulse wave measured by the pulse wave sensor has a periodic pattern. Accordingly, when the pulse wave is continuously measured, the time point at which a new pulse wave peak is measured can be predicted to some extent. As a result, the electronic device can easily obtain the time point at which the pulse wave is measured by using the time point at which a new pulse wave peak is to be measured and, thus, deterioration of the quality of the cardiac potential signal in simultaneous measurement of the pulse wave and the cardiac potential can be prevented.

In addition, when a person grips an electronic device naturally, that is, as usual, the finger of the person touches both the electrode and the pulse wave sensor, and simultaneous measurement of the pulse wave and the cardiac potential is appropriately performed.

In addition, the electronic device can be made compact while maintaining the shielding effect of the electrode by the shield member. As a result, when a person grips the electronic device naturally, the finger of the person touches both the electrode and the pulse wave sensor more easily and, thus, simultaneous measurement of the pulse wave and the cardiac potential is appropriately performed.

In addition, the electronic device can control the shielding effect by the shield member on the basis of an instruction from the user. As a result, simultaneous measurement of the pulse wave and cardiac potential can be performed at a time point according to the intention of the user.

In addition, the electronic device can measure the cardiac potential with higher accuracy by using an active electrode.

In addition, by using the buffer circuit, the electronic device further drives the shield member of the interconnect wire through which the signal amplified by the first amplifying unit is sent. As a result, noise coupled into the cardiac potential acquired by the electrode due to the pulse wave signal can be reduced more.

In addition, the electronic device can control whether the shield member for the interconnect wire through which the signal amplified by the first amplifying unit is transmitted is driven by the buffer circuit. Thus, control can be performed such that the driving is performed when necessary. By performing driving when necessary, power consumption can be reduced.

Furthermore, in the electronic device, in addition to the first electrode and the first interconnect wire, the second electrode and the third interconnect wire are shielded by a shield member driven by a second buffer circuit having a relatively large drive current. As a result, noise coupled into the cardiac potential acquired by the electrode due to the pulse wave signal can be reduced more.

In the above-described exemplary embodiments, each of the constituent elements may be configured by using dedicated hardware or execution of a software program suitable for the constituent element. Each of the constituent elements may be realized by a program execution unit, such as a central processing unit (CPU) or a processor, reading out and executing a software program recorded on a recording medium, such as a hard disk or a semiconductor memory. Here, the software for achieving the electronic device and the like according to the above-described exemplary embodiments is the following program.

That is, a program that causes a computer to perform a method for controlling an electronic device is provided. The electronic device includes a first electrode and a second electrode used to measure a cardiac potential, a pulse wave sensor disposed closer to the first electrode than to the second electrode, where the pulse wave sensor detects a pulse wave, a first amplifying unit that amplifies a signal acquired by the first electrode, a first interconnect wire that electrically connects the first electrode to a terminal of the first amplifying unit, where the first interconnect wire transmits the signal, a first shield member that shields the first electrode and the first interconnect wire, and a shield potential controller including a first buffer circuit and a second buffer circuit having a drive current that is larger than a drive current of the first buffer circuit. The method includes obtaining a predetermined time point when the pulse wave sensor measures the pulse wave, starting applying, to the first shield member, a first generation signal generated by the first buffer circuit on a basis of the signal before the predetermined time point; and starting applying, to the first shield member, a second generation signal generated by the second buffer circuit on a basis of the signal at the predetermined time point.

While the information processing system (the electronic device) and the like according to one or more aspects have been described with reference to the exemplary embodiments above, the present disclosure is not limited to the exemplary embodiments. A variety of modifications of the present embodiments that are conceivable by those skilled in the art and an embodiment configured by combining constituent elements of different embodiments may be encompassed in the scope of one or a plurality of aspects of the present disclosure without departing from the spirit and scope of the present disclosure.

The information processing system according to the present disclosure includes a biopotential measurement device and a pulse wave signal measurement device and is useful as a health monitoring device or the like. In addition, the information processing system can be applied to games.

What is claimed is:
1. An electronic device comprising:
a first electrode and a second electrode used to measure a cardiac potential;
a pulse wave sensor disposed closer to the first electrode than to the second electrode, the pulse wave sensor measuring a pulse wave;
a first amplifier that amplifies a signal acquired by the first electrode, the first amplifier having a terminal;
a first interconnect wire that electrically connects the first electrode to the terminal, the first interconnect wire transmitting the signal;
a first shield member that shields the first electrode and the first interconnect wire; and
a shield potential controller including a first buffer circuit and a second buffer circuit, a drive current of the second buffer circuit being larger than a drive current of the first buffer circuit,
wherein before a predetermined time point when the pulse wave sensor measures the pulse wave, the shield potential controller starts applying, to the first shield member, a first generation signal generated by the first buffer circuit on a basis of the signal,
wherein at the predetermined time point, the shield potential controller starts applying, to the first shield member, a second generation signal generated by the second buffer circuit on a basis of the signal, and
wherein the shield potential controller includes a first switch that switches whether the first generation signal is applied to the first shield member and a second switch that switches whether the second generation signal is applied to the first shield member.

2. The electronic device according to claim 1, wherein the first electrode is configured to contact with one of the fingers of a person to acquire the signal, and the pulse wave sensor detects the pulse wave from the finger.

3. The electronic device according to claim 1, wherein the pulse wave sensor includes a light emitter and a light emission control circuit that generates a light emission control signal used to control light emission of the light emitter, and
wherein the shield potential controller acquires the light emission control signal and defines a time point when the acquired light emission control signal causes the light emitter to emit light as the predetermined time point.

4. The electronic device according to claim 1, wherein the shield potential controller defines, as the predetermined time point, a time point when a new pulse wave peak is to be detected, and
wherein the time point is predicted on a basis of the pulse wave detected by the pulse wave sensor.

5. The electronic device according to claim 1, further comprising:
a casing configured to be gripped by the fingers of a person,
wherein the first electrode and the pulse wave sensor are disposed side by side in a first direction so as to be exposed to the outside of the casing,
wherein the first electrode is circular in plan view, and
wherein the following expression is satisfied:

$$F \geq X + D + Y$$

where in plan view, X represents a diameter of the first electrode, Y represents a length of the pulse wave sensor in the first direction, D represents a minimum distance to be maintained between the first electrode and the pulse wave sensor, and F represents a diameter of a normal substantially circular contact area between the finger and the casing.

6. The electronic device according to claim 1, wherein the first shield member has an annular shape concentric with the first electrode in plan view,
wherein a distance between the first electrode and the first shield member is greater than or equal to twice a minimum value of a wiring interval on a substrate, and
wherein a width of the first shield member in a diameter direction in plan view is greater than or equal to three times the minimum value of the wiring interval on the substrate.

7. The electronic device according to claim 1, further comprising:
a reception unit that receives one of a first instruction and a second instruction,
where the first instruction instructs the shield potential controller to apply the first generation signal to the first shield member without applying the second generation signal to the first shield member, and the second instruction instructs the shield potential controller to apply the first generation signal to the first shield member and further apply the second generation signal to the first shield member.

8. The electronic device according to claim 1, wherein each of the first electrode and the second electrode is an active electrode.

9. The electronic device according to claim 1, further comprising:
a signal receiver connected to the first amplifier by using a second interconnect wire, the signal receiver receiving a signal amplified by the first amplifier,
wherein the shield potential controller further applies at least one of the first generation signal and the second generation signal to a second shield member that shields the second interconnect wire.

10. The electronic device according to claim 9, wherein the shield potential controller includes a switcher, and the switcher includes a third switch that switches whether the first generation signal is applied to the second shield member and a fourth switch that switches whether the second generation signal is applied to the second shield member.

11. The electronic device according to claim 1, wherein the shield potential controller further includes a second amplifier that amplifies a second signal acquired by the second electrode, a third interconnect wire that electrically connects the second electrode to a terminal of the second amplifier and transmits the second signal, and a third shield member that shields the second electrode and the third interconnect wire,
wherein the shield potential controller further includes a third buffer circuit and a fourth buffer circuit having a drive current that is larger than a drive current of the third buffer circuit, and
wherein the shield potential controller applies, to the third shield member, a third generation signal generated by the third buffer circuit on a basis of the second signal, and/or the shield potential controller applies, to the third shield member, a fourth generation signal generated by the fourth buffer circuit on a basis of the second signal at the predetermined time point.

12. A method for controlling an electronic device, the electronic device including a first electrode and a second electrode used to measure a cardiac potential, a pulse wave sensor disposed closer to the first electrode than to the second electrode, where the pulse wave sensor measures a pulse wave, a first amplifier that amplifies a signal acquired by the first electrode, a first interconnect wire that electrically connects the first electrode to a terminal of the first amplifier, where the first interconnect wire transmits the signal, a first shield member that shields the first electrode and the first interconnect wire, and a shield potential controller including a first buffer circuit and a second buffer circuit, where a drive current of the second buffer circuit is larger than a drive current of the first buffer circuit, the method comprising:
obtaining a predetermined time point when the pulse wave sensor measures the pulse wave;
starting applying, to the first shield member, a first generation signal generated by the first buffer circuit on a basis of the signal before the predetermined time point; and
starting applying, to the first shield member, a second generation signal generated by the second buffer circuit on a basis of the signal at the predetermined time point,
wherein the shield potential controller includes a first switch that switches whether the first generation signal is applied to the first shield member and a second switch that switches whether the second generation signal is applied to the first shield member.

13. A non-transitory computer-readable recording medium storing a program that causes a computer to perform a method for controlling an electronic device, the electronic device including a first electrode and a second electrode used to measure a cardiac potential, a pulse wave sensor disposed closer to the first electrode than to the second electrode, where the pulse wave sensor measures a pulse wave, a first amplifier that amplifies a signal acquired by the first electrode, a first interconnect wire that electrically connects the first electrode to a terminal of the first amplifier, where the first interconnect wire transmits the signal, a first shield member that shields the first electrode and the first interconnect wire, and a shield potential controller including a first buffer circuit and a second buffer circuit, where drive current of the second buffer circuit is larger than a drive current of the first buffer circuit, the method comprising:
obtaining a predetermined time point when the pulse wave sensor measures the pulse wave;
starting applying, to the first shield member, a first generation signal generated by the first buffer circuit on a basis of the signal before the predetermined time point; and
starting applying, to the first shield member, a second generation signal generated by the second buffer circuit on a basis of the signal at the predetermined time point,
wherein the shield potential controller includes a first switch that switches whether the first generation signal is applied to the first shield member and a second switch that switches whether the second generation signal is applied to the first shield member.

14. An electronic device comprising:
a first electrode and a second electrode used to measure a cardiac potential;
a pulse wave sensor disposed closer to the first electrode than to the second electrode, the pulse wave sensor measuring a pulse wave;
a first amplifier that amplifies a signal acquired by the first electrode, the first amplifier having a terminal;
a first interconnect wire that electrically connects the first electrode to the terminal, the first interconnect wire transmitting the signal;

a first shield member that shields the first electrode and the first interconnect wire; and a shield potential controller including a first buffer circuit and a second buffer circuit, a drive current of the second buffer circuit being larger than a drive current of the first buffer circuit, wherein the shield potential controller includes a first switch that switches whether a first generation signal generated by the first buffer circuit on a basis of the signal is applied to the first shield member and a second switch that switches whether a second generation signal generated by the second buffer circuit on a basis of the signal is applied to the first shield member.

* * * * *